(12) United States Patent  (10) Patent No.: US 8,334,288 B2
Epple et al.  (45) Date of Patent: Dec. 18, 2012

(54) 4-PHENOXYMETHYLPIPERIDINES AS MODULATORS OF GPR119 ACTIVITY

(75) Inventors: Robert Epple, San Diego, CA (US); Gerald Lelais, San Diego, CA (US); Victor Nikulin, Carlsbad, CA (US); Lucas Westcott-Baker, Goleta, CA (US)

(73) Assignee: IRM LLC, Hamilton (BM)

( * ) Notice: Subject to any disclaimer, the term of this patent is extended or adjusted under 35 U.S.C. 154(b) by 87 days.

(21) Appl. No.: 13/003,558

(22) PCT Filed: Jul. 9, 2009

(86) PCT No.: PCT/US2009/050139
§ 371 (c)(1),
(2), (4) Date: Apr. 1, 2011

(87) PCT Pub. No.: WO2010/006191
PCT Pub. Date: Jan. 14, 2010

(65) Prior Publication Data
US 2011/0190298 A1    Aug. 4, 2011

Related U.S. Application Data

(60) Provisional application No. 61/080,096, filed on Jul. 11, 2008.

(51) Int. Cl.
*A61K 31/496* (2006.01)
*C07D 241/02* (2006.01)
*C07D 401/00* (2006.01)

(52) U.S. Cl. ............... 514/252.11; 514/253.01; 544/357; 544/360; 544/405

(58) Field of Classification Search ............ 514/252.11, 514/253.01; 544/357, 360, 405
See application file for complete search history.

(56) References Cited

U.S. PATENT DOCUMENTS
2009/0270409 A1 * 10/2009 Alper et al. .............. 514/252.11

FOREIGN PATENT DOCUMENTS
WO  WO2007003960  1/2007
WO  WO2007003962  1/2007
WO  WO2008081205  7/2008
WO  WO2009038974  3/2009

OTHER PUBLICATIONS

Hubschwerlen, et al., "Structure-activity relationship in the oxazolidinon-quinolone hybrid series: Influence of the central spacer on the antibacterial activity and the mode of action", Bioorganic and Medicinal Chemistry Letters, Dec. 1, 2003, pp. 4229-4233, vol. 13, No. 23, Elsevier Science, GB.

* cited by examiner

*Primary Examiner* — Susannah Chung
(74) *Attorney, Agent, or Firm* — Chihang Amy Smith; Genomics Institute of the Novartis Research Foundation

(57) ABSTRACT

The present invention provides compounds of Formula I, pharmaceutical compositions comprising such compounds and methods of using such compounds to treat or prevent; diseases or disorders associated with the activity of GPR119.

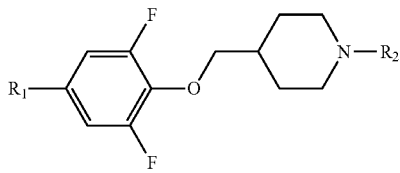

7 Claims, No Drawings

4-PHENOXYMETHYLPIPERIDINES AS MODULATORS OF GPR119 ACTIVITY

CROSS-REFERENCE TO RELATED APPLICATIONS

This application is a 371 U.S. national phase application of international application number PCT/US2009/050139 filed 9 Jul. 2009, which claims priority to U.S. provisional patent application No. 61/080,096, filed 11 Jul. 2008. The full disclosure of these applications is incorporated herein by reference in its entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of GPR119.

2. Background

GPR119 is a G-protein coupled receptor (GPCR) that is mainly expressed in the pancreas, small intestine, colon and adipose tissue. The expression profile of the human GPR119 receptor indicates its potential utility as a target for the treatment of obesity and diabetes. The novel compounds of this invention modulate the activity of GPR119 and are, therefore, expected to be useful in the treatment of GPR119-associated diseases or disorders such as, but not limited to, diabetes, obesity and associated metabolic disorders.

SUMMARY OF THE INVENTION

In one aspect, the present invention provides a compound of Formula I:

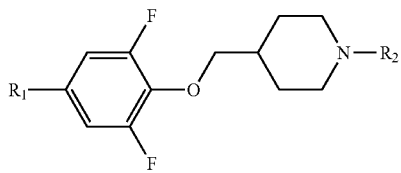

in which:

$R_1$ is selected from phenyl, pyridin-2-yl, pyridin-3-yl, pyridin-4-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl and 2-oxo-2,3-dihydrooxazolo[4,5-b]pyridin-6-yl; wherein said phenyl, pyridin-2-yl, pyridin-3-yl, pyridin-4-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl or 2-oxo-2,3-dihydrooxazolo[4,5-b]pyridin-6-yl of $R_1$ is optionally substituted with 1 to 3 radicals independently selected from halo, —$X_1R_4$, —$X_{10}R_4$, —$X_1C(O)R_4$, —$X_1C(O)OR_4$, —$X_2NR_4C(O)R_4$, —$X_1S(O)_2R_4$, —$X_1NR_4S(O)_2R_4$, —$X_1C(O)NR_4R_5$, —$X_1C(O)NR_4X_2OR_5$, —$X_1C(O)NR_4X_2NR_4R_5$, —$X_1C(O)NR_4X_2C(O)OR_5$, —$X_1S(O)_{0-2}X_2R_4$, —$X_1S(O)_{0-2}X_2OR_4$, —$X_2CN$, —$X_1OX_2R_4$, —$X_1NR_5X_2R_4$, —$X_2NR_4R_5$, —$X_1S(O)_{0-2}X_2C(O)R_4$, —$X_1S(O)_{0-2}X_2C(O)OR_4$ and —$X_1S(O)_{0-2}NR_4R_5$; wherein $X_1$ is selected from a bond, O, $NR_6$ and $C_{1-4}$alkylene; $R_5$ is selected from hydrogen and $C_{1-6}$alkyl; each $X_2$ is independently selected from a bond and $C_{1-4}$alkylene; each $R_4$ is independently selected from hydrogen, $C_{1-6}$alkyl, $C_{6-10}$aryl, $C_{1-10}$heteroaryl, $C_{3-8}$heterocycloalkyl, $C_{3-8}$cycloalkyl and —$X_3C(O)OR_7$, —$X_3R_7$, —$X_3OR_7$, —$X_3NR_7R_8$; wherein said alkyl, aryl, heteroaryl, cycloalkyl and heterocycloalkyl of $R_4$ is optionally substituted with 1 to 3 radicals independently selected from hydroxy, halo, amino, cyano, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, $C_{6-10}$aryl-$C_{1-4}$alkoxy and —$NR_7C(O)R_8$; $X_3$ is $C_{1-3}$alkylene; and $R_7$ is selected from hydrogen, $C_{1-6}$alkyl and $C_{3-8}$heterocycloalkyl optionally substituted with $C_{1-6}$alkyl; $R_8$ are independently selected from hydrogen and $C_{1-6}$alkyl; and $R_2$ is selected from $R_9$ and —$C(O)OR_9$; wherein $R_9$ is selected from $C_{1-6}$alkyl, $C_{6-10}$ aryl, $C_{1-10}$heteroaryl, $C_{3-8}$cycloalkyl and $C_{3-8}$heterocycloalkyl; wherein said alkyl, aryl, heteroaryl, cycloalkyl or heterocycloalkyl of $R_9$ is optionally substituted with 1 to 3 radicals independently selected from halo, $C_{1-6}$alkyl, $C_{3-12}$cycloalkyl, $C_{3-8}$heterocycloalkyl, halo-substituted-$C_{1-6}$alkyl, hydroxy-substituted-$C_{1-6}$alkyl, $C_{1-6}$alkoxy and halo-substituted-$C_{1-6}$alkoxy; or the pharmaceutically acceptable salts thereof.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of GPR119 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which GPR119 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be straight-chained, branched, cyclic or spiro. $C_{1-6}$alkoxy includes methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example, $C_{1-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, 1H-pyridin-2-onyl, 6-oxo-1,6-dihydro-pyridin-3-yl, etc. Heteroaryl also includes the N-oxide derivatives, for example, pyridine N-oxide derivatives with the following structure:

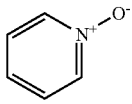

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 2-oxo-pyrrolidin-1-yl, 2-oxo-piperidin-1-yl, etc.

GPR119 means G protein-coupled receptor 119 (GenBank® Accession No. AAP72125) is also referred to in the literature as RUP3 and GPR116. The term GPR119 as used herein includes the human sequences found in GeneBank accession number AY288416, naturally-occurring allelic variants, mammalian orthologs, and recombinant mutants thereof.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of GPR119 activity can prevent, inhibit or ameliorate the pathology and/or symptomology of the diseases, which method comprises administering to the animal a therapeutically effective amount of a compound of Formula I.

In one embodiment, with reference to compounds of Formula I, $R_2$ is selected from 5-ethylpyrimidin-2-yl, tert-butoxycarbonyl and (1-methylcyclopropoxy)carbonyl.

In a further embodiment, $R_1$ is selected from phenyl, pyridin-2-yl, pyridin-3-yl, pyridin-4-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl and 2-oxo-2,3-dihydrooxazolo[4,5-b]pyridin-6-yl; wherein said phenyl, pyridin-2-yl, pyridin-3-yl, pyridin-4-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl or 2-oxo-2,3-dihydrooxazolo[4,5-b]pyridin-6-yl of $R_1$ is optionally substituted with 1 to 2 radicals independently selected from methyl-sulfonyl, 3-methyloxetan-3-yl)methylsulfonyl, isobutyl-sulfonyl, propyl-sulfonyl, isopropyl-sulfonyl, cyano, cyano-methyl, hydroxy-methyl, pyrrolidin-1-yl, methoxy, chloro, methyl, acetyl-amino, methyl-sulfonyl-amino, benzyl-oxy, amino-carbonyl, carboxyl, 2-hydroxypropan-2-yl, 1-aminocyclopropyl, 2H-tetrazol-5-yl, 2H-tetrazol-5-yl-methyl, 1H-tetrazol-5-yl, 1-methyl-1H-tetrazol-5-yl, 2-methyl-2H-tetrazol-5-yl-methyl, 1H-1,2,4-triazol-1-yl, oxazol-5-yl, 1H-pyrazol-3-yl, methylamino-methyl, t-butoxy-amino-methyl, morpholino-methyl, 1H-imidazol-1-yl-methyl, 2H-tetrazol-2-yl-methyl, 1H-tetrazol-1-yl-methyl, methyl-amino-carbonyl, dimethyl-amino-carbonyl, methyl-piperazinyl, piperazinyl-carbonyl, morpholino-carbonyl, 2-methoxyethylcarbamoyl, 2-hydroxyethylcarbamoyl and 2-hydroxypropylcarbamoyl.

In a further embodiment, are compounds selected from: 2-(4-((2,6-difluoro-4-(5-(methylsulfonyl)pyridin-2-yl)phenoxy)methyl)piperidin-1-yl)-5-ethylpyrimidine; tert-butyl 4-((3,5-difluoro-4'-(methylsulfonyl)biphenyl-4-yloxy)methyl)piperidine-1-carboxylate; 2-(4-((3,5-difluoro-4'-(3-methyloxetan-3-yl)methylsulfonyl)biphenyl-4-yloxy)methyl) piperidin-1-yl)-5-ethylpyrimidine; 2-(4-((3,5-difluoro-4'-(isobutylsulfonyl)biphenyl-4-yloxy)methyl)piperidin-1-yl)-5-ethylpyrimidine; 2-(4-((3,5-difluoro-4'-(propylsulfonyl)biphenyl-4-yloxy)methyl)piperidin-1-yl)-5-ethylpyrimidine; 2-(4-((3,5-difluoro-4'-(methylsulfonyl)biphenyl-4-yloxy)methyl)piperidin-1-yl)-5-ethylpyrimidine; 2-(4-((3,5-difluoro-4'-(isopropylsulfonyl)biphenyl-4-yloxy)methyl)piperidin-1-yl)-5-ethylpyrimidine; 4'-((1-(5-ethylpyrimidin-2-yl)piperidin-4-yl)methoxy)-3',5'-difluorobiphenyl-4-carbonitrile; 4'-((1-(5-ethylpyrimidin-2-yl)piperidin-4-yl)methoxy)-3',5'-difluorobiphenyl-3-carbonitrile; 2-(4'-((1-(5-ethylpyrimidin-2-yl)piperidin-4-yl)methoxy)-3',5'-difluorobiphenyl-3-yl) acetonitrile; (4'-((1-(5-ethylpyrimidin-2-yl)piperidin-4-yl) methoxy)-3',5'-difluorobiphenyl-3-yl)methanol; 2-(4-((3,5-difluoro-3'-(methylsulfonyl)biphenyl-4-yloxy)methyl) piperidin-1-yl)-5-ethylpyrimidine; 2-(4'-((1-(5-ethylpyrimidin-2-yl)piperidin-4-yl)methoxy)-3',5'-difluorobiphenyl-4-yl)acetonitrile; (4'-((1-(5-ethylpyrimidin-2-yl)piperidin-4-yl)methoxy)-3',5'-difluorobiphenyl-4-yl)methanol; 2-(4-((2,6-difluoro-4-(2-(pyrrolidin-1-yl)pyrimidin-5-yl)phenoxy)methyl)piperidin-1-yl)-5-ethylpyrimidine; 2-(4-((2,6-difluoro-4-(pyrimidin-5-yl)phenoxy)methyl)piperidin-1-yl)-5-ethylpyrimidine; 2-(4-((3,5-difluorobiphenyl-4-yloxy)methyl)piperidin-1-yl)-5-ethylpyrimidine; 2-(4-((2,6-difluoro-4-(pyridin-4-yl)phenoxy)methyl)piperidin-1-yl)-5-ethylpyrimidine; tert-butyl 4-((2,6-difluoro-4-(2-methoxypyridin-4-yl)phenoxy)methyl)piperidine-1-carboxylate; tert-butyl 4-((2,6-difluoro-4-(pyridin-4-yl)phenoxy)methyl)piperidine-1-carboxylate; 2-(4-((2,6-difluoro-4-(6-(methylsulfonyl)pyridin-3-yl)phenoxy)methyl)piperidin-1-yl)-5-ethylpyrimidine; 2-(4-((4-(6-chloro-2-methylpyridin-3-yl)-2,6-difluorophenoxy)methyl) piperidin-1-yl)-5-ethylpyrimidine; 2-(4-((2,6-difluoro-4-(1-methyl-1H-pyrazol-4-yl)phenoxy)methyl)piperidin-1-yl)-5-ethylpyrimidine; 2-(4-((2,6-difluoro-4-(1H-pyrazol-4-yl) phenoxy)methyl)piperidin-1-yl)-5-ethylpyrimidine; 5-(4-((1-(5-ethylpyrimidin-2-yl)piperidin-4-yl)methoxy)-3,5-difluorophenyl)picolinonitrile; 2-(4-((2,6-difluoro-4-(3-methoxypyridin-4-yl)phenoxy)methyl)piperidin-1-yl)-5-ethylpyrimidine; N-(4'-((1-(5-ethylpyrimidin-2-yl) piperidin-4-yl)methoxy)-3',5'-difluorobiphenyl-4-yl) acetamide; N-(4'-((1-(5-ethylpyrimidin-2-yl)piperidin-4-yl)methoxy)-3',5'-difluorobiphenyl-4-yl)methanesulfonamide; 2-(4-((4-(6-(benzyloxy)pyridin-3-yl)-2,6-difluorophenoxy) methyl)piperidin-1-yl)-5-ethylpyrimidine; 5-(4-((1-(5-ethylpyrimidin-2-yl)piperidin-4-yl)methoxy)-3,5-difluorophenyl)pyridin-2(1H)-one; 2-(4-((2,6-difluoro-4-(2-methoxypyrimidin-5-yl)phenoxy)methyl)piperidin-1-yl)-5-ethylpyrimidine; 5-(4-((1-(5-ethylpyrimidin-2-yl)piperidin-4-yl)methoxy)-3,5-difluorophenyl)pyrimidin-2(1H)-one; 5-(4-((1-(5-ethylpyrimidin-2-yl)piperidin-4-yl)methoxy)-3,5-difluorophenyl)pyrimidine-2-carboxamide; tert-butyl 4-((2,6-difluoro-4-(pyridin-3-yl)phenoxy)methyl)piperidine-1-carboxylate; 5-(4-((1-(5-ethylpyrimidin-2-yl)piperidin-4-yl)methoxy)-3,5-difluorophenyl)pyrimidine-2-carboxylic acid; 2-(5-(4-((1-(5-ethylpyrimidin-2-yl)piperidin-4-yl)methoxy)-3,5-difluorophenyl)pyridin-2-yl)propan-2-ol; 2-(4-((3,5-difluoro-4'-(1H-tetrazol-5-yloxy)methyl)piperidin-1-yl)-5-ethylpyrimidine; 2-(4-((3,5-difluoro-3'-(2H-tetrazol-5-yl)biphenyl-4-yloxy)methyl)piperidin-1-yl)-5-ethylpyrimidine; 2-(4-((3'-((2H-tetrazol-5-yl)methyl)-3,5-difluorobiphenyl-4-yloxy)methyl)piperidin-1-yl)-5-ethylpyrimidine; 2-(4-((4'-((2H-tetrazol-5-yl)methyl)-3,5-difluorobiphenyl-4-yloxy)methyl)piperidin-1-yl)-5-ethylpyrimidine; 2-(4-((4-(6-(2H-tetrazol-5-yl)pyridin-3-yl)-2,6-difluorophenoxy)methyl)piperidin-1-yl)-5-ethylpyrimidine; 2-(4-((3,5-difluoro-4'-(2-methyl-2H-tetrazol-5-yl)biphenyl-4-yloxy)methyl)piperidin-1-yl)-5-ethylpyrimidine; 2-(4-((3,5-difluoro-4'-(1-methyl-1H-tetrazol-5-yl)biphenyl-4-yloxy)methyl)piperidin-1-yl)-5-ethylpyrimidine; 2-(4-((3,5-difluoro-3'-(2-methyl-2H-tetrazol-5-yl)biphenyl-4-yloxy)methyl)piperidin-1-yl)-5-ethylpyrimidine; 2-(4-((3,5-difluoro-3'-(1-methyl-1H-tetrazol-5-yl)biphenyl-4-yloxy)methyl)piperidin-1-yl)-5-ethylpyrimidine; 2-(4-((3,5-difluoro-3'-((2-methyl-2H-tetrazol-5-yl)methyl)biphenyl-4-yloxy)methyl)piperidin-1-yl)-5-ethylpyrimidine; 2-(4-((3,5-difluoro-3'-((1-methyl-1H-tetrazol-5-yl)methyl)biphenyl-4-yloxy)methyl)piperidin-1-yl)-5-ethylpyrimidine; 2-(4(3,5-difluoro-4'-((2-methyl-2H-tetrazol-5-yl)methyl)biphenyl-4-yloxy)methyl)piperidin-1-yl)-5-ethylpyrimidine; 2-(4-((3,5-difluoro-4'-((1-methyl-1H-tetrazol-5-yl)methyl)biphenyl-4-yloxy)methyl)piperidin-1-yl)-5-ethylpyrimidine; 2-(4-((2,6-difluoro-4-(6-(2-methyl-2H-tetrazol-5-yl)pyridin-3-yl)phenoxy)methyl)piperidin-1-yl)-5-ethylpyrimidine; 2-(4-((2,6-difluoro-4-(6-(1-methyl-1H-tetrazol-5-yl)pyridin-3-yl)phenoxy)methyl)piperidin-1-yl)-5-ethylpyrimidine; 1-methylcyclopropyl 4-((3,5-difluoro-4'-(methylsulfonyl)biphenyl-4-yloxy)methyl)piperidine-1-carboxylate; 4-(4-((1-(tert-butoxycarbonyl)piperidin-4-yl)methoxy)-3,5-difluorophenyl)pyridine 1-oxide; tert-butyl 4-((2,6-difluoro-4-(2-oxo-1,2-dihydropyridin-4-yl)phenoxy)methyl)piperidine-1-carboxylate; tert-butyl 4-((2,6-difluoro-4-(1-methyl-2-oxo-1,2-dihydropyridin-4-yl)phenoxy)methyl)piperidine-1-carboxylate; 2-(4-((2,6-difluoro-4-(2-methyl-6-(1H-1,2,4-triazol-1-yl)pyridin-3-yl)phenoxy)methyl)piperidin-1-yl)-5-ethylpyrimidine; 2-(4-((2,6-difluoro-4-(2-methyl-6-(methylsulfonyl)pyridin-3-yl)phenoxy)methyl)piperidin-1-yl)-5-ethylpyrimidine; 5-(4'-((1-(5-ethylpyrimidin-2-yl)piperidin-4-yl)methoxy)-3',5'-difluorobiphenyl-4-yl)oxazole; 2-(4-((3,5-difluoro-4'-(1H-pyrazol-3-yl)biphenyl-4-yloxy)methyl)piperidin-1-yl)-5-ethylpyrimidine; 1-(4'-((1-(5-ethylpyrimidin-2-yl)piperidin-4-yl)methoxy)-3',5'-difluorobiphenyl-4-yl)-N-methylmethanamine; N-((4'-((1-(5-ethylpyrimidin-2-yl)piperidin-4-yl)methoxy)-3',5'-difluorobiphenyl-4-yl)methyl)-2-methylpropan-2-amine; 4-((4'-((1-(5-ethylpyrimidin-2-yl)piperidin-4-yl)methoxy)-3',5'-difluorobiphenyl-4-yl)methyl)morpholino; 2-(4-((4'-((1H-imidazol-1-yl)methyl)-3,5-difluorobiphenyl-4-yloxy)methyl)piperidin-1-yl)-5-ethylpyrimidine; 2-(4-((4'-((2H-tetrazol-2-yl)methyl)-3,5-difluorobiphenyl-4-yloxy)methyl)piperidin-1-yl)-5-ethylpyrimidine; 2-(4-((4'-((1H-tetrazol-1-yl)methyl)-3,5-difluorobiphenyl-4-yloxy)methyl)piperidin-1-yl)-5-ethylpyrimidine; 5-(4-((1-(5-ethylpyrimidin-2-yl)piperidin-4-yl)methoxy)-3,5-difluorophenyl)picolinamide; 5-(4-((1-(5-ethylpyrimidin-2-yl)piperidin-4-yl)methoxy)-3,5-difluorophenyl)-N-methylpicolinamide; 5-(4-((1-(5-ethylpyrimidin-2-yl)piperidin-4-yl)methoxy)-3,5-difluorophenyl)-N,N-dimethylpicolinamide; 1-methylcyclopropyl 4-((2,6-difluoro-4-(2-(piperazine-1-carbonyl)pyrimidin-5-yl)phenoxy)methyl)piperidine-1-carboxylate; 1-methylcyclopropyl 4-(4-(2-(dimethylcarbamoyl)pyrimidin-5-yl)-2,6-difluorophenoxy)methyl)piperidine-1-carboxylate; 1-methylcyclopropyl 4-((2,6-difluoro-4-(2-(morpholine-4-carbonyl)pyrimidin-5-yl)phenoxy)methyl)piperidine-1-carboxylate; 1-methylcyclopropyl 4-((2,6-difluoro-4-(2-(2-methoxyethylcarbamoyl)pyrimidin-5-yl)phenoxy)methyl)piperidine-1-carboxylate; 1-methylcyclopropyl 4-((2,6-difluoro-4-(2-oxo-2,3-dihydrooxazolo[4,5-b]pyridin-6-yl)phenoxy)methyl)piperidine-1-carboxylate; 1-methylcyclopropyl 4-((2,6-difluoro-4-(2-(2-hydroxyethylcarbamoyl)pyrimidin-5-yl)phenoxy)methyl)piperidine-1-carboxylate; and 1-methylcyclopropyl 4-((2,6-difluoro-4-(2-(3-hydroxypropylcarbamoyl)pyrimidin-5-yl)phenoxy)methyl)piperidine-1-carboxylate.

In another embodiment, $R_1$ is selected from phenyl, pyridin-2-yl, pyridin-3-yl, pyridin-4-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl and 2-oxo-2,3-dihydrooxazolo[4,5-b]pyridin-6-yl; wherein said phenyl, pyridin-2-yl, pyridin-3-yl, pyridin-4-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl or 2-oxo-2,3-dihydrooxazolo[4,5-b]pyridin-6-yl of $R_1$ is optionally substituted with 1 to 2 radicals independently selected from (S)-3-hydroxypyrrolidine-1-carbonyl, 4-hydroxypiperidine-1-carbonyl, bis(2-hydroxyethyl)carbamoyl, morpholino-ethyl-amino, 4-methylpiperazin-1-yl, 1-acetamidocyclopropyl, 2-((3-methyloxetan-3-yl)methyl)-2H-tetrazol-5-yl, (2-hydroxyethyl)(methyl)carbamoyl, (2-hydroxyethyl)(ethyl)carbamoyl, 2-carboxyethylcarbamoyl, 3-ethoxy-3-oxopropylcarbamoyl, carboxymethylcarbamoyl, 2-tert-butoxy-2-oxoethylcarbamoyl, 4-methylpiperazine-1-carbonyl, (2-(dimethylamino)ethyl)(methyl)carbamoyl and 3,4-dihydroxypyrrolidine-1-carbonyl.

In another embodiment are compounds selected from: 5-(4-((1-(5-ethylpyrimidin-2-yl)piperidin-4-yl)methoxy)-3,5-difluorophenyl)-N-(2-morpholinoethyl)pyridin-2-amine; 2-(4-((2,6-difluoro-4-(6-(4-methylpiperazin-1-yl)pyridin-3-yl)phenoxy)methyl)piperidin-1-yl)-5-ethylpyrimidine; 1-methylcyclopropyl 4-((4-(6-(1-aminocyclopropyl)pyridin-3-yl)-2,6-difluorophenoxy)methyl)piperidine-1-carboxylate; 1-methylcyclopropyl 4-((4-(6-(1-acetamidocyclopropyl)pyridin-3-yl)-2,6-difluorophenoxy)methyl)piperidine-1-carboxylate; 2-(4-((3,5-difluoro-4'-(2-((3-methyloxetan-3-yl)methyl)-2H-tetrazol-5-yl)biphenyl-4-yloxy)methyl)piperidin-1-yl)-5-ethylpyrimidine; 1-methylcyclopropyl 4-((4-(2-((3R,4R)-3,4-dihydroxypyrrolidine-1-carbonyl)pyrimidin-5-yl)-2,6-difluorophenoxy)methyl)piperidine-1-carboxylate; 1-methylcyclopropyl 4-((4-(2-((2-(dimethylamino)ethyl)(methyl)carbamoyl)pyrimidin-5-yl)-2,6-difluorophenoxy)methyl)piperidine-1-carboxylate; 1-methylcyclopropyl 4-((2,6-difluoro-4-(2-(4-methylpiperazine-1-carbonyl)pyrimidin-5-yl)phenoxy)methyl)piperidine-1-carboxylate; 1-methylcyclopropyl 4-((2,6-difluoro-4-(2-((2-hydroxyethyl)(methyl)carbamoyl)pyrimidin-5-yl)phenoxy)methyl)piperidine-1-carboxylate; 1-methylcyclopropyl 4-(4-(2-(ethyl(2-hydroxyethyl)carbamoyl)pyrimidin-5-yl)-2,6-difluorophenoxy)methyl)piperidine-1-carboxylate; 3-(5-(3,5-difluoro-4-((1-((1-methylcyclopropoxy)carbonyl)piperidin-4-yl)methoxy)phenyl)pyrimidine-2-carboxamido)propanoic acid; 1-methylcyclopropyl 4-((4-(2-(3-ethoxy-3-oxopropylcarbamoyl)pyrimidin-5-yl)-2,6-difluorophenoxy)methyl)piperidine-1-carboxylate; 2-(5-(3,5-difluoro-4-((1-((1-methylcyclopropoxy)carbonyl)piperidin-4-yl)methoxy)phenyl)pyrimidine-2-carboxamido)acetic acid; 1-methylcyclopropyl 4-((4-(2-(2-tert-butoxy-2-oxoethylcarbamoyl)pyrimidin-5-yl)-2,6-difluorophenoxy)methyl)piperidine-1-carboxylate; 1-methylcyclopropyl 4-((4-(2-(bis(2-hydroxyethyl)carbamoyl)pyrimidin-5-yl)-2,6-difluorophenoxy)methyl)piperidine-1-carboxylate; 1-methylcyclopropyl 4-((2,6-difluoro-4-(2-(4-hydroxypiperidine-1-carbonyl)pyrimidin-5-yl)phenoxy)methyl)piperidine-1-carboxylate; and (S)-1-methylcyclopropyl 4-((2,6-difluoro-4-(2-(3-hydroxypyrrolidine-1-carbonyl)pyrimidin-5-yl)phenoxy)methyl)piperidine-1-carboxylate.

Further compounds of the invention are detailed in the Examples and Table I, infra.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^{3}H$ or $^{14}C$ is incorporated, are useful in drug and/or substrate tissue distribution studies. In particular examples, $^{3}H$ and $^{14}C$ isotopes may be used for their ease of preparation and detectability. In other examples, substitution with isotopes such as $^{2}H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. For example, the following three examples can be deuterated as shown:

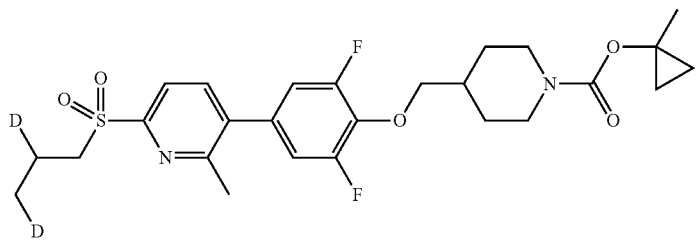

deuterated Example F4

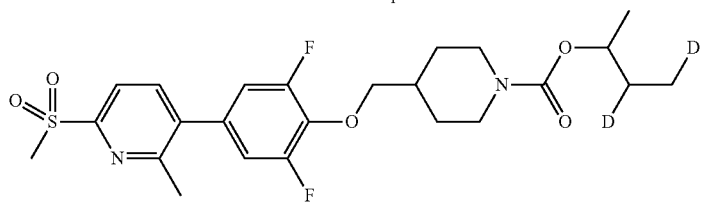

deuterated Example F5

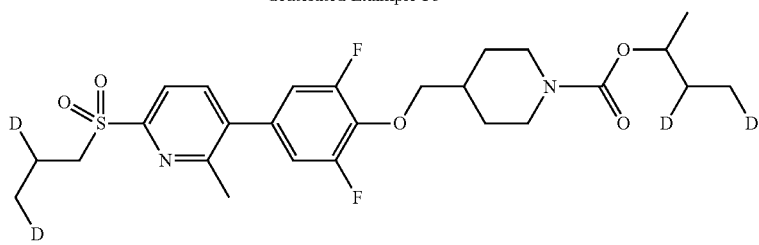

deuterated Example F6

Pharmacology and Utility

Compounds of the invention modulate the activity of GPR119 and, as such, are useful for treating diseases or disorders in which the activity of GPR119 contributes to the pathology and/or symptomology of the disease. This invention further provides compounds of this invention for use in the preparation of medicaments for the treatment of diseases or disorders in which GPR119 activity contributes to the pathology and/or symptomology of the disease.

The resultant pathologies of Type II diabetes are impaired insulin signaling at its target tissues and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling. Physiological signaling systems which function in this manner are well-characterized and include the gut peptides GLP-1, GIP and PACAP. These hormones act via their cognate G-protein coupled receptor to stimulate the production of cAMP in pancreatic β-cells. The increased cAMP does not appear to result in stimulation of insulin release during the fasting or pre-prandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including GPR119, would also stimulate the release of endogenous insulin and consequently promote normoglycemia in Type II diabetes. It is also established that increased cAMP, for example as a result of GLP-1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

Some β-cell GPCRs, including GPR119, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In an embodiment of the invention is a method for treatment of a metabolic disease and/or a metabolic-related disorder in an individual comprising administering to the individual in need of such treatment a therapeutically effective amount of a compound of the invention or a pharmaceutical composition thereof. The metabolic diseases and metabolic-related disorders are selected from, but not limited to, hyperlipidemia, type 1 diabetes, type 2 diabetes mellitus, idiopathic type 1 diabetes (Type Ib), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertryglyceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

In an embodiment of the invention are therapeutic benefits of GPR119 activity modulators derived from increasing levels of GIP and PPY. For example, neuroprotection, learning and memory, seizures and peripheral neuropathy.

GLP-1 and GLP-1 receptor agonists have been shown to be effective for treatment of neurodegenerative diseases and other neurological disorders. GLP-1 and exendin-4 have been shown to stimulate neurite outgrowth and enhance cell survival after growth factor withdrawal in PC12 cells. In a rodent model of neurodegeneration, GLP-1 and exendin-4 restore cholinergic marker activity in the basal forebrain. Central infusion of GLP-1 and exendin-4 also reduce the levels of amyloid-β peptide in mice and decrease amyloid precursor protein amount in cultured PC12 cells. GLP-1 receptor agonists have been shown to enhance learning in rats and the GLP-1 receptor knockout mice show deficiencies in learning behavior. The knockout mice also exhibit increased susceptibility to kainate-induced seizures which can be prevented by administration of GLP-1 receptor agonists. GLP-1 and exendin-4 has also been shown to be effective in treating pyridoxine-induced peripheral nerve degeneration, an experimental model of peripheral sensory neuropathy.

Glucose-dependent insulinotropic polypeptide (GIP) has also been shown to have effects on proliferation of hippocampal progenitor cells and in enhancing sensorimotor coordination and memory recognition.

In an embodiment of the invention are therapeutic benefits of GPR119 activity modulators. For example, GLP-2 and short bowel syndrome (SBS). Several studies in animals and from clinical trials have shown that GLP-2 is a trophic hormone that plays an important role in intestinal adaptation. Its role in regulation of cell proliferation, apoptosis, and nutrient absorption has been well documented. Short bowel syndrome is characterized by malabsorption of nutrients, water and vitamins as a result of disease or surgical removal of parts of the small intestine (eg. Crohn's disease). Therapies that improve intestinal adaptation are thought to be beneficial in treatment of this disease. In fact, phase II studies in SBS patients have shown that teduglutide, a GLP-2 analog, modestly increased fluid and nutrient absorption.

In an embodiment of the invention are therapeutic benefits of GPR119 activity modulators derived from increasing levels of GIP and PPY. For example, GLP-1, GIP and osteoporosis. GLP-1 has been shown to increase calcitonin and calcitonin related gene peptide (CGRP) secretion and expression in a murine C-cell line (CA-77). Calcitonin inhibits bone resorption by osteoclasts and promotes mineralization of skeletal bone. Osteoporosis is a disease that is characterized by reduced bone mineral density and thus GLP-1 induced increase in calcitonin might be therapeutically beneficial.

GIP has been reported to be involved in upregulation of markers of new bone formation in osetoblasts including collagen type I mRNA and in increasing bone mineral density. Like GLP-1, GIP has also been shown to inhibit bone resorption.

In an embodiment of the invention are therapeutic benefits of GPR119 activity modulators derived from increasing levels of GIP and PPY. For example, PPY and gastric emptying. GPR119 located on the pancreatic polypeptide (PP) cells of the islets has been implicated in the secretion of PPY. PPY has been reported to have profound effects on various physiological processes including modulation of gastric emptying and gastrointestinal motility. These effects slow down the digestive process and nutrient uptake and thereby prevent the postprandial elevation of blood glucose. PPY can suppress food intake by changing the expression of hypothalamic feeding-regulatory peptides. PP-overexpressing mice exhibited the thin phenotype with decreased food intake and gastric emptying rate.

In accordance with the foregoing, the present invention further provides a method for preventing or ameliorating the symptamology of any of the diseases or disorders described above in a subject in need thereof, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations).

For example, synergistic effects can occur with other anti-obesity agents, anorectic agents, appetite suppressant and related agents. Diet and/or exercise can also have synergistic effects. Anti-obesity agents include, but are not limited to, apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, compounds described in WO2006/047516), melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Where compounds of the invention are administered in conjunction with other therapies, dosages of the co-administered compounds will of course vary depending on the type of co-drug employed, on the specific drug employed, on the condition being treated and so forth.

A combined preparation or pharmaceutical composition can comprise a compound of the invention as defined above or a pharmaceutical acceptable salt thereof and at least one active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. G1-262570; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as a CB1 activity modulator, melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5, 491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389.

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-$HT_3$ receptor and/or an agent interacting with 5-$HT_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfuram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention.

Reaction Scheme I

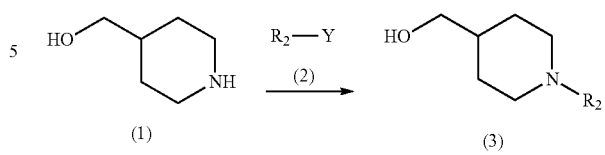

wherein $R_2$ is as described in the Summary of the Invention. A compound of formula 3 can be prepared as in reaction scheme I by reacting a compound of formula 1 with a compound of the formula 2 (where Y is a leaving group and refers to a chloride, bromide, iodide, triflate, nonaflate, carbonate or other appropriate leaving groups familiar to one skilled in the art) in a suitable solvent such as DMF, DMA, $CH_3CN$, $CH_2Cl_2$ and the like in the presence of a suitable base such as $Cs_2CO_3$, $NEt_3$ or the like. The reaction proceeds at a temperature of about −20° C. to about 140° C. and can take up to 24 hours to complete. In this scheme, it is understood that the groups designated $R_2$ may be protected versions of the radicals defined in the Summary of the Invention which may be deprotected and manipulated to the final compound after completion of this scheme or in the middle of the scheme.

Reaction Scheme II

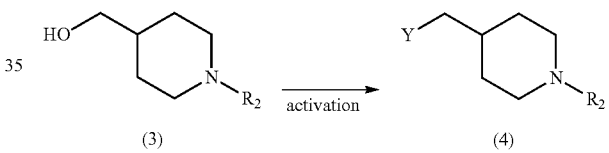

wherein Y refers to a leaving group such as an alkylsulfonate ester, halide or other appropriate group familiar to one skilled in the art and $R_2$ is as defined in the Summary of the Invention. A compound of the formula 4 can be prepared as in reaction scheme II by reacting a compound of formula 3 with methanesulfonyl chloride, $SOCl_2$ or the like in the presence or absence of a base such as $NEt_3$, $EtNiPr_2$ or the like in a solvent such as $CH_2Cl_2$, $CHCl_3$, AcOEt or the like. The reaction proceeds at a temperature of about −20° C. to about 40° C. and can take up to 24 h to complete.

Reaction Scheme III

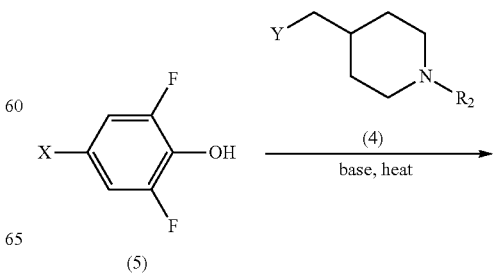

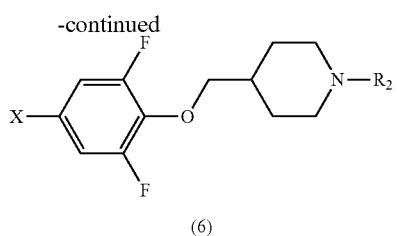

(6)

A compound of formula 6 can be prepared as in reaction scheme III by reacting a compound of formula 5 (where X refers to a chloride, bromide, iodide, triflate, nonaflate and the like) with a compound of the formula 4 (where Y refers to a leaving group such as an alkylsulfonate ester, halide or other appropriate group familiar to one skilled in the art) in a suitable solvent such as DMF, THF, $CH_3CN$ and the like in the presence of a suitable base such as $Cs_2CO_3$, NaH or the like. The reaction proceeds at a temperature of about 50° C. to about 140° C. and can take up to 24 h to complete.

Reaction Scheme IV

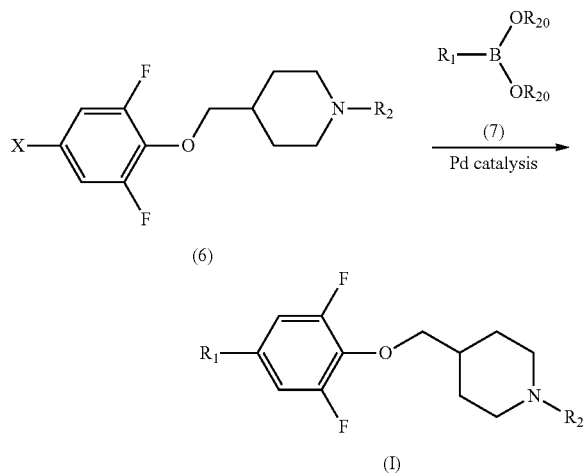

A compound of the Formula I can be prepared as in reaction scheme IV by reacting a compound of formula 6 (where X refers to a chloride, bromide, iodide, triflate, nonaflate and the like) with a compound of formula 7 (where $R_1$ is as described in the Summary of the Invention and $B(OR_{20})_2$ refers to a boronic acid or boronic ester such as boronic acid pinacol ester and the like) using the Pd methodology known in the art. The reaction proceeds at a temperature of about −78° C. to about 100° C. and can take up to 24 h to complete.

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
(a) that of reaction schemes I, II, III & IV; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following Examples that illustrate the preparation of compounds of the invention.

Example A1

2-(4-((2,6-difluoro-4-(5-(methylsulfonyl)pyridin-2-yl)phenoxy)methyl)piperidin-1-yl)-5-ethylpyrimidine

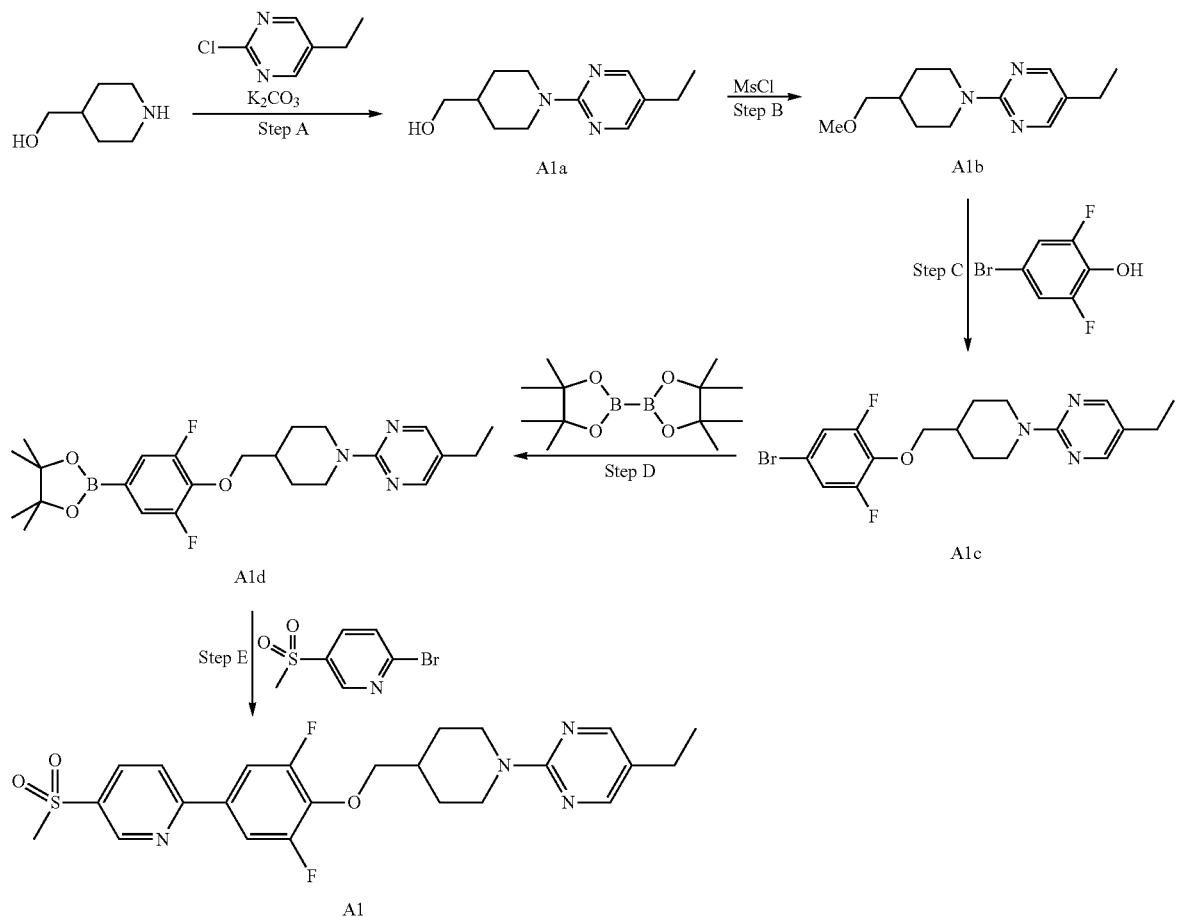

Step A: Piperidinemethanol (10.7 g, 93 mmol) is dissolved in DMA (60 mL), treated with 2-chloro-5-ethylpyrimidine (14.57 g, 102 mmol) and $K_2CO_3$ (19.3 g, 140 mmol) and heated to 130° C. overnight. The solid is filtered, washed with DMA and discarded. The filtrate is evaporated and the crude purified by flash chromatography (EtOAc/hexanes gradient) to afford (1-(5-ethylpyrimidin-2-yl)piperidin-4-yl)methanol A1a as yellow oil: $^1$H-NMR (400 MHz, CDCl$_3$) δ=8.16 (s, 2H), 4.75-4.72 (m, 2H), 3.53 (d, J=6.0 Hz, 2H), 2.91-2.83 (m, 2H), 2.45 (q, J=7.6 Hz, 2H), 1.84-1.73 (m, 3H), 1.27-1.20 (m, 2H), 1.18 (t, J=7.6 Hz, 3H); MS calcd. for [M+H]$^+$ $C_{12}H_{20}N_3O$: 222.1. found: 222.1.

Step B: Intermediate A1a (10 g, 45.2 mmol) is dissolved in $CH_2Cl_2$ (70 mL), treated with NEt$_3$ (12.6 mL, 90.4 mmol) and cooled to 0° C. Methanesulfonylchloride (3.9 mL, 50 mmol) is added dropwise and the mixture stirred at rt for 2.5 h. The mixture is then poured into 1M HCl and extracted with CH₂Cl₂ (3×). The org. phase is washed with brine, dried (Na₂SO₄) and concentrated in vacuo. The crude product is recrystallized from EtOAc/hexane to afford (1-(5-ethylpyrimidin-2-yl)piperidin-4-yl)methyl methanesulfonate A1b as a white solid: ¹H-NMR (400 MHz, CDCl₃) δ=8.39 (s, 2H), 5.03-4.99 (m, 2H), 4.11 (d, J=6.0 Hz, 2H), 3.20-3.12 (m, 2H), 3.03 (s, 3H), 2.59 (q, J=7.6 Hz, 2H), 2.21-2.10 (m, 1H), 2.03-2.00 (m, 2H), 1.48-1.37 (m, 2H), 1.25 (t, J=7.6 Hz, 3H); MS calcd. for [M+H]⁺ C₁₃H₂₂N₃O₃S: 300.1. found: 300.1.

Step C: To a solution of 4-bromo-2,6-difluorophenol (1.15 g, 5.5 mmol) and Intermediate A1b (1.50 g, 5.0 mmol) in DMF (20 mL) is added Cs₂CO₃ (2.50 g, 7.7 mmol). The resulting suspension is heated to 90° C. for 2 h, cooled to rt, and diluted with H₂O (100 mL). The mixture is extracted with EtOAc (3×40 mL), and the combined organics washed with brine, dried over MgSO₄, and concentrated in vacuo. Purification by flash chromatography (EtOAc/hexanes gradient) affords 2-(4-((4-bromo-2,6-difluorophenoxy)methyl)piperidin-1-yl)-5-ethylpyrimidine A1c as a colorless oil that solidifies upon standing: ¹H-NMR (400 MHz, CDCl₃) δ=8.19 (s, 2H), 7.10 (d, J=7.7 Hz, 2H), 4.77 (br d, J=13.2 Hz, 2H), 3.98 (d, J=6.8 Hz, 2H), 2.92 (td, J=14.4, 2.8 Hz, 2H), 2.47 (q, J=7.6 Hz, 2H), 2.09 (m, 1H), 1.95 (br d, J=14.4 Hz, 2H), 1.35 (qd, J=14.4, 4.4 Hz, 2H), 1.21 (t, J=7.6 Hz, 3H); ¹⁹F-NMR (376.5 MHz, CDCl₃) δ=−126.00; MS calcd. for [M+H]⁺ C₁₈H₂₁BrF₂N₃O: 412.1. found: 412.1.

Step D: To a solution of Intermediate A1c (1.03 g, 2.5 mmol) in DMSO (20 mL) are added bis(pinacolato)diboron (706 mg, 2.8 mmol), potassium acetate (740 mg, 7.5 mmol), and dichloro[1,1'-bis(diphenylphosphino)ferrocene]palladium(II) (95 mg, 5 mol %). The mixture is heated to 80° C. for 2.5 h. The solution is then cooled to rt, diluted with H₂O (100 mL), and extracted with EtOAc (3×30 mL). The organic layer is dried over MgSO₄ and concentrated in vacuo. Purification by flash chromatography (EtOAc/hexanes gradient) affords 2-(4-((2,6-difluoro-4-(4,4,5,5-tetramethyl-1,3,2-dioxaborolan-2-yl)phenoxy)methyl)piperidin-1-yl)-5-ethylpyrimidine A1d as a colorless oil: ¹H-NMR (400 MHz, CDCl₃) δ=8.16 (s, 2H), 7.30 (d, J=8.5 Hz, 2H), 4.75 (d, J=13.2 Hz, 2H), 4.03 (d, J=6.4 Hz, 2H), 2.90 (td, J=12.8, 2.8 Hz, 2H), 2.45 (q, J=7.6 Hz, 2H), 2.07 (m, 1H), 1.93 (d, J=12.8 Hz, 2H), 1.32 (s, 12H), 1.18 (t, J=7.6 Hz, 3H); ¹⁹F-NMR (376.5 MHz, CDCl₃) δ=−129.18; MS calcd. for [M+H]⁺ C₂₄H₃₃BF₂N₃O₃: 460.3. found: 460.3.

Step E: A vial is charged with Intermediate A1d (344 mg, 0.75 mmol), 2-bromo-5-(methylsulfonyl)pyridine (199 mg, 0.84 mmol), dichloro[1,1'-bis(diphenylphosphino)ferrocene]palladium(II) (38 mg, 6 mol %), and dry dioxane (1.5 mL). To the solution is added 1M aqueous Cs₂CO₃ (1 mL, 1.0 mmol), and the biphasic mixture is subjected to microwave irradiation (120° C., 15 min). The mixture is diluted with H₂O (20 mL) and extracted with EtOAc (3×25 mL). The organic phase is washed with brine (10 mL), dried over MgSO₄, and concentrated in vacuo. Purification by flash chromatography (EtOAc/hexanes gradient) affords the title compound (Example A1) as a white crystalline powder: ¹H-NMR (400 MHz, CDCl₃) δ=9.16 (dd, J=2.4, 0.8 Hz, 1H), 8.27 (dd, J=8.4, 2.4 Hz, 1H), 8.17 (s, 2H), 7.82 (dd, J=8.4, 0.8 Hz, 1H), 7.67 (d, J=9.2 Hz, 2H), 4.78 (d, J=13.2 Hz, 2H), 4.10 (d, J=6.4 Hz, 2H), 3.14 (s, 3H), 2.92 (td, J=12.8, 2.4 Hz, 2H), 2.46 (q, J=7.6 Hz, 2H), 2.11 (m, 1H), 1.96 (d, J=13.2 Hz, 2H), 1.36 (qd, J=12.4, 4.0 Hz, 2H), 1.19 (t, J=7.6 Hz, 3H); ¹⁹F-NMR (376.5 MHz, CDCl₃) δ=−126.56; MS calcd. for [M+H]⁺ C₂₄H₂₇F₂N₄O₃S: 489.2. found: 489.2.

Example A2 tert-butyl 4-((3,5-difluoro-4'-(methylsulfonyl)biphenyl-4-yloxy)methyl)piperidine-1-carboxylate

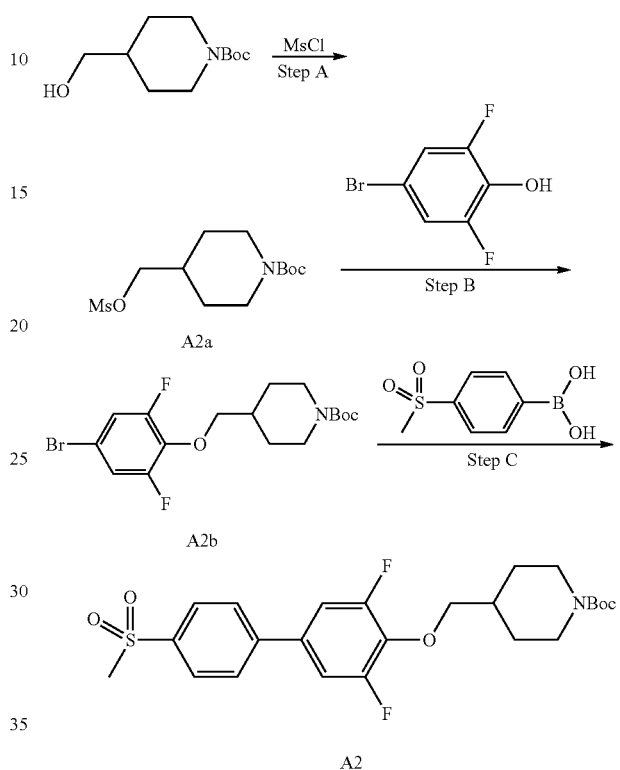

Step A: Tert-butyl 4-((methylsulfonyloxy)methyl)piperidine-1-carboxylate A2a is prepared from tert-butyl 4-(hydroxymethyl)piperidine-1-carboxylate (30 g, 139 mmol) according to the same procedure described for the preparation of Intermediate A1b. MS calcd. for [M-Boc+21-1]⁺ C₈H₁₆NO₅S: 238.3. found: 238.0. The product is used without purification.

Step B: Tert-butyl 4-((4-bromo-2,6-difluorophenoxy)methyl)piperidine-1-carboxylate A2b is prepared from 4-bromo-2,6-difluorophenol (1.67 g, 8 mmol) and Intermediate A2a (2.35 g, 8 mmol) according to the same procedure described for the preparation of Intermediate A1c. MS calcd. for [M+Na]⁺C₁₇H₂₂BrF₂NNaO₃: 428.1. found: 428.2. The product is used without purification.

Step C: A mixture of Intermediate A2b (20.3 mg, 0.05 mmol), 4-(methanesulfonyl)benzeneboronic acid (12.0 mg, 0.06 mmol), Na₂CO₃ (15.9 mg, 0.15 mmol) and Pd(PPh₃)₄ (1.7 mg, 0.0015 mmol) in H₂O (0.24 mL), EtOH (0.18 mL) and DME (0.72 mL) is subjected to microwave irradiation (180° C., 10 min) under nitrogen atmosphere. After cooling, the mixture is diluted with MeCN and filtered. The filtrate is purified by reverse-phase HPLC to yield the title compound (Example A2): ¹H-NMR (400 MHz, CDCl₃) δ=8.01 (m, 2H), 7.69 (m, 2H), 7.16 (m, 2H), 4.16 (m, 2H), 4.04 (d, J=6.4 Hz, 2H), 3.09 (s, 3H), 2.76 (t, J=12.4 Hz, 2H), 1.98 (m, 1H), 1.86 (m, 2H), 1.47 (s, 9H), 1.28 (m, 2H); ¹⁹F-NMR (376.5 MHz, CDCl₃) δ=−126.74; MS calcd. for [M+Na]+ C₂₄H₂₉F₂NNaO₅S: 504.2. found: 504.1.

Example A3

2-(4-((3,5-difluoro-4'-((3-methyloxetan-3-yl)methyl-sulfonyl)biphenyl-4-yloxy)methyl)piperidin-1-yl)-5-ethylpyrimidine

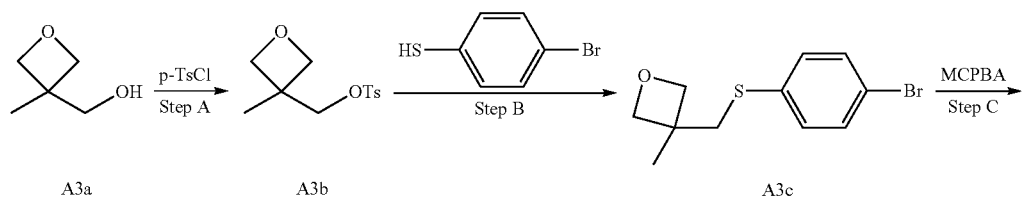

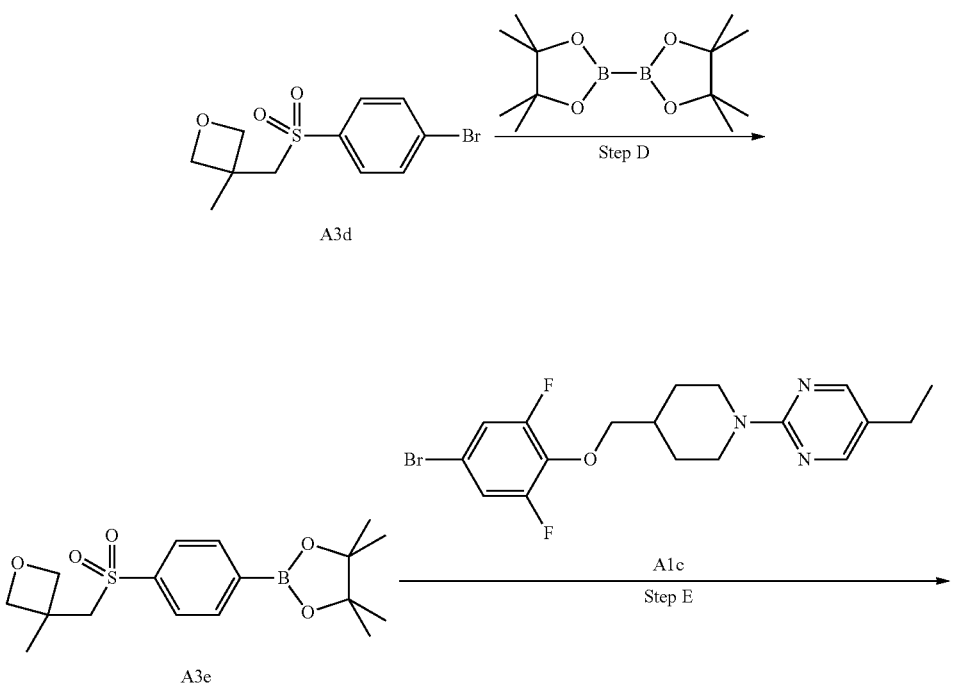

Step A: To a solution of p-toluenesulfonyl chloride (14.3 g, 75 mmol) in pyridine (60 mL) is slowly added 3-methyl-3-oxetanemethanol A3a (5.1 g, 50 mmol) over 10 min. The resulting suspension is stirred at rt for 1.5 h and poured into vigorously stirred ice water (300 mL). The slurry is stirred for 45 min. The solid is collected by filtration, washed with ice-cold H$_2$O (100 mL), and dried under high vacuum to afford (3-methyloxetan-3-yl)methyl 4-methylbenzene-sulfonate A3b as a white powder. The compound is used in the next step without further purification. $^1$H-NMR (400 MHz, CDCl$_3$) δ=7.83 (d, J=8.4 Hz, 2H), 7.39 (d, J=8.4 Hz, 2H), 4.39 (d, J=6.4 Hz, 2H), 4.36 (d, J=6.4 Hz, 2H), 4.13 (s, 2H), 2.49 (s, 3H), 1.33 (s, 3H).

Step B: Intermediate A3b (1.75 g, 6.8 mmol), 4-bromobenzenethiol (1.25 g, 6.6 mmol), and Cs$_2$CO$_3$ (3.25 g, 10 mmol) are suspended in dry DMF (12 mL) and heated to 80° C. for 1.5 h. The mixture is cooled, diluted with H$_2$O (50 mL), and extracted with Et$_2$O (3×30 mL). The combined organics are washed with 2M Na$_2$CO$_3$ (15 mL), dried over MgSO$_4$, and concentrated in vacuo to afford crude 3-((4-bromophenylthio)methyl)-3-methyloxetane A3c as a yellow oil. The compound is used in the next step without further purification. $^1$H-NMR (400 MHz, CDCl$_3$) δ=7.34 (d, J=8.4 Hz, 2H), 7.17 (d, J=8.4 Hz, 2H), 4.40 (d, J=6.0 Hz, 2H), 4.31 (d, J=6.0 Hz, 2H), 3.19 (s, 2H), 1.33 (s, 3H); MS calcd. for [M+H]$^+$ C$_{11}$H$_{14}$BrOS: 273.0. found: 273.0.

Step C: To a solution of Intermediate A3c (1.8 g, 6.6 mmol) in CH$_2$Cl$_2$ (30 mL) is added m-chloroperoxybenzoic acid (max. 77%, 3.5 g, approx. 15.6 mmol) in small portions until complete conversion to the sulfone (LC-MS). The mixture is stirred for an additional 4 h, then diluted with CH$_2$Cl$_2$ (40 mL), and washed successively with H$_2$O (50 mL), 2M Na$_2$CO$_3$ (30 mL), 10% NaHSO$_3$ (15 mL), and H$_2$O (30 mL). The organics are dried over MgSO$_4$ and the solvent removed in vacuo to afford crude 3-((4-bromophenylsulfonyl)methyl)-3-methyloxetane A3d as a white solid. The compound is used in the next step without further purification. $^1$H-NMR (400 MHz, CDCl$_3$) δ=7.72 (d, J=8.8 Hz, 2H), 7.67 (d, J=8.8 Hz, 2H), 4.54 (d, J=6.4 Hz, 2H), 4.35 (d, J=6.4 Hz, 2H), 3.41 (s, 2H), 1.61 (s, 3H); MS calcd. for [M+H]$^+$ C$_{11}$H$_{14}$BrO$_3$S: 305.0. found: 304.9.

Step D: To a solution of Intermediate A3d (1.94 g, 6.4 mmol) in DMSO (45 mL) are added bis(pinacolato)diboron (1.7 g, 6.7 mmol), potassium acetate (1.9 g, 19 mmol), and dichloro[1,1'-bis(diphenylphosphino)ferrocene]palladium (II) (233 mg, 5 mol %). The mixture is heated to 80° C. for 3 h. Then, the solution is cooled to rt, diluted with H$_2$O (100 mL), and extracted with EtOAc (4×50 mL). The organic layer is washed with H$_2$O (30 mL) and brine (30 mL), dried over MgSO$_4$, and concentrated in vacuo. Purification by flash chromatography (EtOAc/hexanes gradient) affords 4,4,5,5-tetramethyl-2-(4-((3-methyloxetan-3-yl)methylsulfonyl)phenyl)-1,3,2-dioxaborolane A3e as a white crystalline powder: $^1$H-NMR (400 MHz, CDCl$_3$) δ=8.02 (d, J=8.4 Hz, 2H), 7.92 (d, J=8.4 Hz, 2H), 4.60 (d, J=6.4 Hz, 2H), 4.40 (d, J=6.4 Hz, 2H), 3.50 (s, 2H), 1.69 (s, 3H), 1.39 (s, 12H); MS calcd. for [M+H]$^+$ C$_{17}$H$_{26}$BO$_5$S: 353.2. found: 353.2.

Step E: A Smith Process vial is charged with Intermediate A1c (50 mg, 0.12 mmol), Intermediate A3e (46 mg, 0.14 mmol), dichloro[1,1'-bis(diphenylphosphino)ferrocene]palladium(II) (9 mg, 10 mol %), and dry dioxane (1.5 mL). To the solution is added 2M aqueous Cs$_2$CO$_3$ (0.15 mL, 0.3 mmol), and the biphasic mixture subjected to microwave irradiation (120° C., 10 min). The mixture is partitioned between H$_2$O (10 mL) and EtOAc (15 mL), and the organic phase washed with brine (10 mL), dried over MgSO$_4$, and concentrated in vacuo. Purification by flash chromatography (EtOAc/hexanes gradient) affords the title compound (Example A3) as a pale yellow powder: $^1$H-NMR (400 MHz, CDCl$_3$) δ=8.18 (s, 2H), 7.98 (d, J=8.4 Hz, 2H), 7.70 (d, J=8.4 Hz, 2H), 7.17 (d, J=9.0 Hz, 2H), 4.78 (d, J=13.2 Hz, 2H), 4.63 (d, J=6.4 Hz, 2H), 4.43 (d, J=6.4 Hz, 2H), 4.07 (d, J=6.8 Hz, 2H), 3.52 (s, 2H), 2.93 (td, J=12.8, 2.8 Hz, 2H), 2.46 (q, J=7.6 Hz, 2H), 2.12 (m, 1H), 1.95 (d, J=12.8 Hz, 2H), 1.71 (s, 3H), 1.36 (qd, J=12.2, 4.0 Hz, 2H), 1.19 (t, J=7.6 Hz, 3H); $^{19}$F-NMR (376.5 MHz, CDCl$_3$) δ=−126.60; MS calcd. for [M+H]$^+$ C$_{29}$H$_{33}$F$_2$N$_3$O$_4$S: 558.2. found: 558.2.

By repeating the procedures described in the above Examples A1-A3, using appropriate starting materials, the following compounds of Formula I, as identified in Table 1, are obtained:

TABLE 1

| Example # | Structure | NMR and/or ESMS |
|---|---|---|
| A4 | 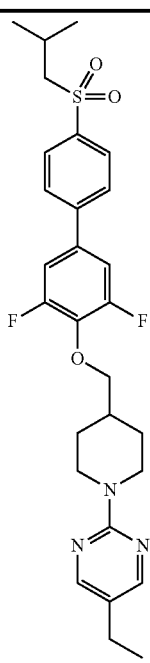 | $^1$H-NMR (400 MHz, CDCl$_3$) δ = 8.20 (s, 2H), 7.99 (d, J = 8.4 Hz, 2H), 7.70 (d, J = 8.4 Hz, 2H), 7.19 (d, J = 8.8 Hz, 2H), 4.79 (d, J = 13.2 Hz, 2H), 4.08 (d, J = 6.4 Hz, 2H), 3.04 (d, J = 6.4 Hz, 2H), 2.94 (td, J = 12.8, 2.4 Hz, 2H), 2.48 (q, J = 7.6 Hz, 2H), 2.28 (septet, J = 6.8 Hz, 1H), 2.14 (m, 1H), 1.99 (d, J = 12.8 Hz, 2H), 1.38 (qd, J = 12.2, 4.0 Hz, 2H), 1.21 (t, J = 7.6 Hz, 3H), 1.10 (d, J = 6.8 Hz, 6H); $^{19}$F-NMR (376.5 MHz, CDCl$_3$) δ = −126.73; MS calcd. for [M + H]$^+$ C$_{28}$H$_{34}$F$_2$N$_3$O$_3$S: 530.2, found: 530.3. |

TABLE 1-continued

| Example # | Structure | NMR and/or ESMS |
|---|---|---|
| A5 | 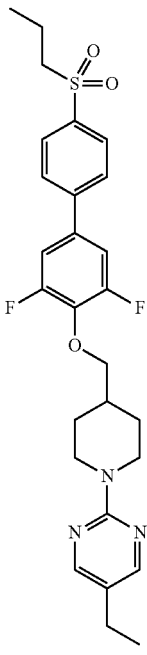 | $^1$H-NMR (400 MHz, CDCl$_3$) δ = 8.19 (s, 2H), 7.98 (d, J = 8.4 Hz, 2H), 7.70 (d, J = 8.4 Hz, 2H), 7.18 (d, J = 9.2 Hz, 2H), 4.79 (d, J = 13.2 Hz, 2H), 4.08 (d, J = 6.4 Hz, 2H), 3.12 (m, 2H), 2.94 (td, J = 12.8, 2.8 Hz, 2H), 2.48 (q, J = 7.6 Hz, 2H), 2.13 (m, 1H), 1.98 (dd, J = 13.2, 2.4 Hz, 2H), 1.80 (m, 2H), 1.38 (qd, J = 12.2, 4.0 Hz, 2H), 1.21 (t, J = 7.6 Hz, 3H), 1.03 (t, J = 7.6 Hz, 3H); $^{19}$F-NMR (376.5 MHz, CDCl$_3$) δ = −126.72; MS calcd. for [M + H]$^+$ C$_{27}$H$_{32}$F$_2$N$_3$O$_3$S: 516.2, found: 516.2. |
| A6 | 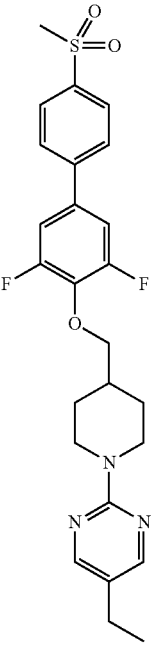 | $^1$H-NMR (400 MHz, CDCl$_3$) δ = 8.11 (s, 2H), 7.94 (d, J = 8.4 Hz, 2H), 7.62 (d, J = 8.4 Hz, 2H), 7.09 (d, J = 9.2 Hz, 2H), 4.71 (d, J = 14.4 Hz, 2H), 4.00 (d, J = 6.4 Hz, 2H), 3.03 (s, 3H), 2.86 (td, J = 12.8, 2.4 Hz, 2H), 2.39 (q, J = 7.6 Hz, 2H), 2.05 (m, 1H), 1.90 (dd, J = 13.2, 2.4 Hz, 2H), 1.29 (qd, J = 12.0, 4.0 Hz, 2H), 1.12 (t, J = 7.6 Hz, 3H); $^{19}$F-NMR (376.5 MHz, CDCl$_3$) δ = −126.68; MS calcd. for [M + H]$^+$ C$_{25}$H$_{28}$F$_2$N$_3$O$_3$S : 488.2, found: 488.2. |

TABLE 1-continued

| Example # | Structure | NMR and/or ESMS |
|---|---|---|
| A7 | 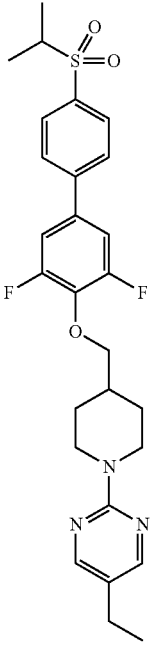 | $^1$H-NMR (400 MHz, CDCl$_3$) δ = 8.11 (s, 2H), 7.87 (d, J = 8.4 Hz, 2H), 7.61 (d, J = 8.4 Hz, 2H), 7.10 (d, J = 9.2 Hz, 2H), 4.71 (d, J = 13.6 Hz, 2H), 4.00 (d, J = 6.4 Hz, 2H), 3.16 (septet, J = 6.8 Hz, 1H), 2.86 (td, J = 12.8, 2.8 Hz, 2H), 2.39 (q, J = 7.6 Hz, 2H), 2.05 (m, 1H), 1.90 (dd, J = 13.6, 2.8 Hz, 2H), 1.29 (qd, J = 12.4, 4.4 Hz, 2H), 1.26 (d, J = 6.8 Hz), 1.12 (t, J = 7.6 Hz, 3H); $^{19}$F-NMR (376.5 MHz, CDCl$_3$) δ = −126.74; MS calcd. for [M + H]$^+$ C$_{27}$H$_{32}$F$_2$N$_3$O$_3$S: 516.2, found: 516.2. |
| A8 | 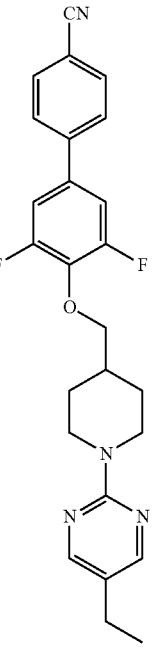 | $^1$H-NMR (400 MHz, CDCl$_3$) δ = 8.11 (s, 2H), 7.66 (d, J = 8.4 Hz, 2H), 7.54 (d, J = 8.4 Hz, 2H), 7.07 (d, J = 9.2 Hz, 2H), 4.70 (d, J = 13.2 Hz, 2H), 3.99 (d, J = 6.4 Hz, 2H), 2.85 (td, J = 12.8, 2.4 Hz, 2H), 2.39 (q, J = 7.6 Hz, 2H), 2.04 (m, 1H), 1.89 (dd, J = 13.2, 2.4 Hz, 2H), 1.29 (qd, J = 12.4, 4.0 Hz, 2H), 1.12 (t, J = 7.6 Hz, 3H); $^{19}$F-NMR (376.5 MHz, CDCl$_3$) δ = −126.68; MS calcd. for [M + H]$^+$ C$_{25}$H$_{25}$F$_2$N$_4$O: 435.2, found: 435.2. |

TABLE 1-continued

| Example # | Structure | NMR and/or ESMS |
|---|---|---|
| A9 | 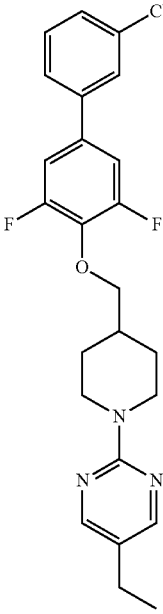 | $^1$H-NMR (400 MHz, CDCl$_3$) δ = 8.18 (s, 2H), 7.78 (t, J = 1.6 Hz, 1H), 7.73 (dt, J = 8.0, 1.6 Hz, 1H), 7.65 (dt, J = 8.0, 1.6 Hz, 1H), 7.55 (t, J = 8.0 Hz, 1H), 7.11 (d, J = 9.2 Hz, 2H), 4.77 (d, J = 13.2 Hz, 2H), 4.05 (d, J = 6.4 Hz, 2H), 2.92 (td, J = 12.8, 2.8 Hz, 2H), 2.46 (q, J = 7.6 Hz, 2H), 2.12 (m, 1H), 1.97 (d, J = 13.2 Hz, 2H), 1.36 (qd, J = 12.4, 4.0 Hz, 2H), 1.19 (t, J = 7.6 Hz, 3H); $^{19}$F-NMR (376.5 MHz, CDCl$_3$) δ = −126.66; MS calcd. for [M + H]$^+$ C$_{25}$H$_{25}$F$_2$N$_4$O: 435.2, found: 435.2. |
| A10 | 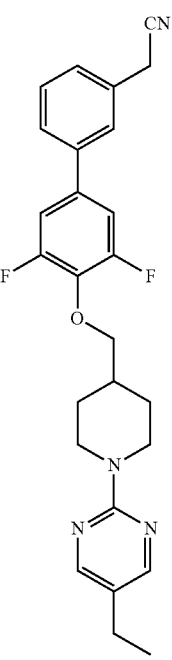 | $^1$H-NMR (400 MHz, CDCl$_3$) δ = 8.17 (s, 2H), 7.46 (m, 3H), 7.33 (m, 1H), 7.12 (d, J = 9.6 Hz, 2H), 4.77 (d, J = 13.2 Hz, 2H), 4.04 (d, J = 6.4 Hz, 2H), 3.82 (s, 2H), 2.92 (td, J = 12.8, 2.8 Hz, 2H), 2.46 (q, J = 7.6 Hz, 2H), 2.11 (m, 1H), 1.97 (d, J = 13.2 Hz, 2H), 1.36 (qd, J = 12.4, 2.4 Hz, 2H), 1.19 (t, J = 7.6 Hz, 3H); $^{19}$F-NMR (376.5 MHz, CDCl$_3$) δ = −127.37; MS calcd. for [M + H]$^+$ C$_{26}$H$_{27}$F$_2$N$_4$O: 449.2, found: 449.2. |

TABLE 1-continued

| Example # | Structure | NMR and/or ESMS |
|---|---|---|
| A11 | 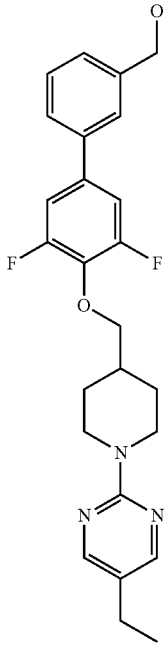 | $^1$H-NMR (400 MHz, CDCl$_3$) δ = 8.17 (s, 2H), 7.52 (s, 1H), 7.43 (m, 2H), 7.37 (m, 1H), 7.14 (d, J = 9.6 Hz, 2H), 4.77 (m, 4H), 4.03 (d, J = 6.4 Hz, 2H), 2.92 (td, J = 12.8, 2.8 Hz, 2H), 2.46 (q, J = 7.6 Hz, 2H), 2.11 (m, 1H), 1.98 (d, J = 13.2 Hz, 2H), 1.73 (t, J = 6.0 Hz, 1H), 1.36 (qd, J = 12.4, 4.4 Hz, 2H), 1.19 (t, J = 7.6 Hz, 3H); $^{19}$F-NMR (376.5 MHz, CDCl$_3$) δ = −127.78; MS calcd. for [M + H]$^+$ C$_{25}$H$_{28}$F$_2$N$_3$O$_2$: 440.2, found: 440.2. |
| A12 | 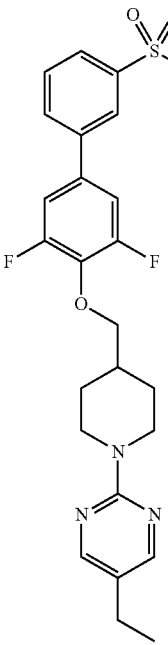 | $^1$H-NMR (400 MHz, CDCl$_3$) δ = 8.17 (s, 2H), 8.07 (t, J = 1.6 Hz, 1H), 7.94 (ddd, J = 7.6, 1.6, 1.2 Hz, 1H), 7.79 (ddd, J = 7.6, 1.6, 1.2 Hz, 1H), 7.65 (t, J = 7.6 Hz, 1H), 7.17 (d, J = 9.2 Hz, 2H), 4.78 (d, J = 13.2 Hz, 2H), 4.06 (d, J = 6.8 Hz, 2H), 3.10 (s, 3H), 2.93 (td, J = 12.8, 2.8 Hz, 2H), 2.46 (q, J = 7.6 Hz, 2H), 2.12 (m, 1H), 1.97 (d, J = 13.2 Hz, 2H), 1.36 (qd, J = 12.4, 4.0 Hz, 2H), 1.19 (t, J = 7.6 Hz, 3H); $^{19}$F-NMR (376.5 MHz, CDCl$_3$) δ = −126.72; MS calcd. for [M + H]$^+$ C$_{25}$H$_{28}$F$_2$N$_3$O$_3$S: 488.2, found: 488.2. |

TABLE 1-continued

| Example # | Structure | NMR and/or ESMS |
|---|---|---|
| A13 | 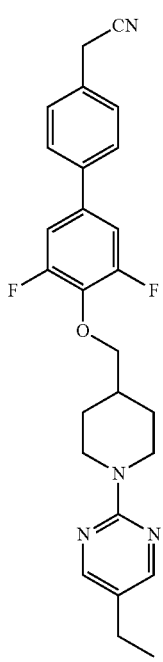 | $^1$H-NMR (400 MHz, CDCl$_3$) δ = 8.17 (s, 2H), 7.52 (d, J = 8.4 Hz, 2H), 7.40 (d, J = 8.4 Hz, 2H), 7.12 (d, J = 9.2 Hz, 2H), 4.77 (d, J = 13.2 Hz, 2H), 4.03 (d, J = 6.4 Hz, 2H), 3.80 (s, 2H), 2.92 (td, J = 12.8, 2.8 Hz, 2H), 2.46 (q, J = 7.6 Hz, 2H), 2.11 (m, 1H), 1.97 (d, J = 13.2 Hz, 2H), 1.36 (qd, J = 12.4, 4.0 Hz, 2H), 1.18 (t, J = 7.6 Hz, 3H); $^{19}$F-NMR (376.5 MHz, CDCl$_3$) δ = −127.47; MS calcd. for [M + H]+ C$_{26}$H$_{27}$F$_2$N$_4$O: 449.2, found: 449.3. |
| A14 | 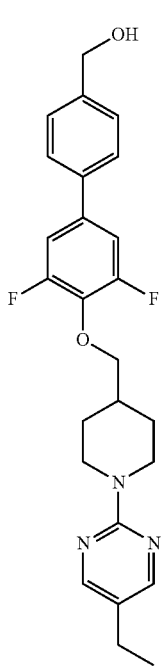 | $^1$H-NMR (400 MHz, CDCl$_3$) δ = 8.17 (s, 2H), 7.51 (d, J = 8.4 Hz, 2H), 7.44 (d, J = 8.4 Hz, 2H), 7.13 (d, J = 9.2 Hz, 2H), 4.77 (d, J = 13.2 Hz, 2H), 4.74 (d, J = 6.0 Hz, 2H), 4.03 (d, J = 6.4 Hz, 2H), 2.92 (td, J = 12.8, 2.8 Hz, 2H), 2.46 (q, J = 7.6 Hz, 2H), 2.11 (m, 1H), 1.97 (d, J = 12.8 Hz, 2H), 1.69 (t, J = 6.0 Hz, 1H), 1.36 (qd, J = 12.4, 4.0 Hz, 2H), 1.18 (t, J = 7.6 Hz, 3H); $^{19}$F-NMR (376.5 MHz, CDCl$_3$) δ = −127.78; MS calcd. for [M + H]$^+$ C$_{25}$H$_{28}$F$_2$N$_3$O$_2$: 440.2, found: 440.3. |

TABLE 1-continued
| Example # | Structure | NMR and/or ESMS |
|---|---|---|
| A15 | 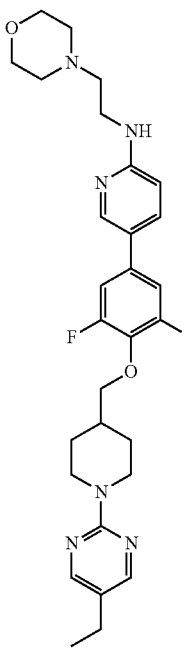 | $^1$H-NMR (400 MHz, DMSO-d6) δ = 8.34 (d, J = 2.8 Hz, 1H), 8.23 (s, 2H), 7.72 (dd, J = 8.8, 2.8 Hz, 1H), 7.39 (m, 2H), 6.67 (t, J = 5.6 Hz, 1H), 6.55 (d, J = 8.8 Hz, 1H), 4.65 (m, 2H), 3.97 (d, J = 6.4 Hz, 2H), 3.58 (t, J = 4.8 Hz, 4H), 3.40 (m, 2H), 2.87 (m, 2H), 2.43 (m, 8H), 2.01 (m, 1H), 1.83 (m, 2H), 1.22 (m, 2H), 1.12 (t, J = 7.6 Hz, 3H); MS calcd. for [M + H]$^+$ C$_{29}$H$_{37}$F$_2$N$_6$O$_2$: 539.3, found: 538.8. |
| A16 | 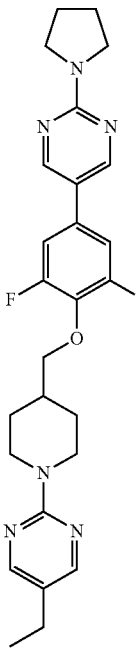 | $^1$H-NMR (400 MHz, DMSO-d6) δ = 8.71 (s, 2H), 8.23 (s, 2H), 7.50 (m, 2H), 4.65 (m, 2H), 3.98 (d, J = 6.4 Hz, 2H), 3.52 (m, 4H), 2.87 (m, 2H), 2.42 (q, J = 7.6 Hz, 2H), 2.01 (m, 1H), 1.94 (m, 4H), 1.83 (m, 2H), 1.22 (m, 2H), 1.12 (t, J = 7.6 Hz, 3H); MS calcd. for [M + H]$^+$ C$_{26}$H$_{31}$F$_2$N$_6$O: 481.2, found: 480.9. |

TABLE 1-continued
| Example # | Structure | NMR and/or ESMS |
|---|---|---|
| A17 | 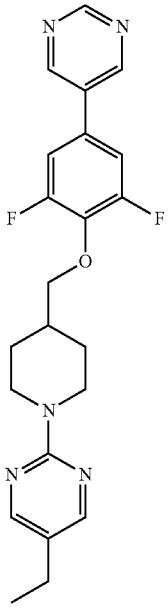 | $^1$H-NMR (400 MHz, DMSO-d6) δ = 9.19 (s, 1H), 9.18 (s, 2H), 8.23 (s, 2H), 7.75 (m, 2H), 4.66 (m, 2H), 4.05 (d, J = 6.3 Hz, 2H), 2.87 (m, 2H), 2.42 (q, J = 7.6 Hz, 2H), 2.03 (m, 1H), 1.83 (m, 2H), 1.23 (m, 2H), 1.12 (t, J = 7.6 Hz, 3H); MS calcd. for [M + H]$^+$ C$_{22}$H$_{24}$F$_2$N$_5$O: 412.2, found: 412.2. |
| A18 | 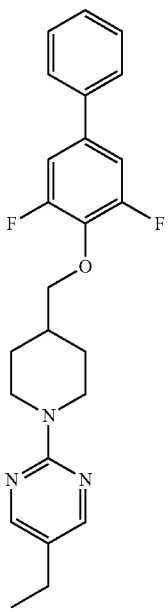 | $^1$H-NMR (400 MHz, DMSO-d6) δ = 8.23 (s, 2H), 7.70 (m, 2H), 7.48 (m, 4H), 7.38 (tt, J = 7.2, 1.2 Hz, 1H), 4.66 (m, 2H), 4.02 (d, J = 6.4 Hz, 2H), 2.88 (m, 2H), 2.42 (q, J = 7.6 Hz, 2H), 2.03 (m, 1H), 1.84 (m, 2H), 1.23 (m, 2H), 1.12 (t, J = 7.6 Hz, 3H); MS calcd. for [M + H]$^+$ C$_{24}$H$_{26}$F$_2$N$_3$O: 410.2, found: 409.9. |

TABLE 1-continued

| Example # | Structure | NMR and/or ESMS |
|---|---|---|
| A19 | 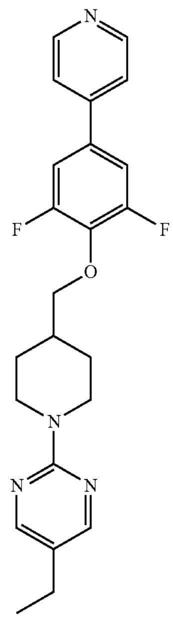 | ¹H-NMR (400 MHz, DMSO-d6) δ = 8.64 (m, 2H), 8.23 (s, 2H), 7.75 (m, 4H), 4.66 (m, 2H), 4.05 (d, J = 6.4 Hz, 2H), 2.87 (m, 2H), 2.41 (q, J = 7.6 Hz, 2H), 2.03 (m, 1H), 1.83 (m, 2H), 1.22 (m, 2H), 1.12 (t, J = 7.6 Hz, 3H); MS calcd. for [M + H]⁺ $C_{23}H_{25}F_2N_4O$: 411.2, found: 411.2. |
| A20 | 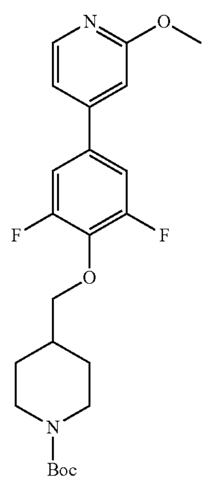 | ¹H-NMR (400 MHz, DMSO-d6) δ = 8.22 (dd, J = 5.6, 0.8 Hz, 1H), 7.69 (m, 2H), 7.36 (dd, J = 5.6, 1.6 Hz, 1H), 7.18 (dd, J = 1.6, 0.8 Hz, 1H), 4.03 (d, J = 6.4 Hz, 2H), 3.97 (m, 2H), 3.89 (s, 3H), 2.73 (m, 2H), 1.90 (m, 1H), 1.75 (m, 2H), 1.39 (s, 9H), 1.16 (m, 2H); MS calcd. for [M + H]⁺ $C_{23}H_{29}F_2N_2O_4$: 435.2, found: 435.2. |
| A21 | 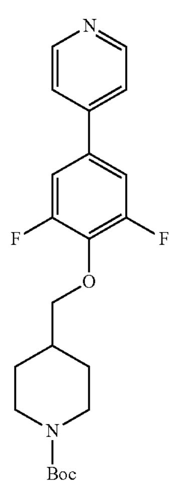 | MS calcd. for [M + H]⁺ $C_{22}H_{27}F_2N_2O_3$: 405.2, found: 405.2. |

TABLE 1-continued

| Example # | Structure | NMR and/or ESMS |
|---|---|---|
| A22 | 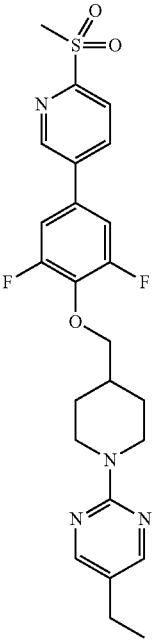 | $^1$H-NMR (400 MHz, CDCl$_3$) δ = 8.86 (dd, J = 2.4, 0.8 Hz, 1H), 8.18 (s, 2H), 8.16 (dd, J = 8.0, 0.8 Hz, 1H), 8.05 (dd, J = 8.0, 2.4 Hz, 1H), 7.17 (d, J = 8.8 Hz, 2H), 4.78 (d, J = 13.2 Hz, 2H), 4.09 (d, J = 6.4 Hz, 2H), 3.27 (s, 3H), 2.93 (td, J = 12.8, 2.8 Hz, 2H), 2.46 (q, J = 7.6 Hz, 2H), 2.12 (m, 1H), 1.96 (d, J = 13.2 Hz, 2H), 1.37 (qd, J = 12.6, 4.0 Hz, 2H), 1.19 (t, J = 7.6 Hz, 3H); $^{19}$F-NMR (376.5 MHz, CDCl$_3$) δ = −125.76; MS calcd. for [M + H]$^+$ C$_{24}$H$_{27}$F$_2$N$_4$O$_3$S: 489.2, found: 489.2. |
| A23 | 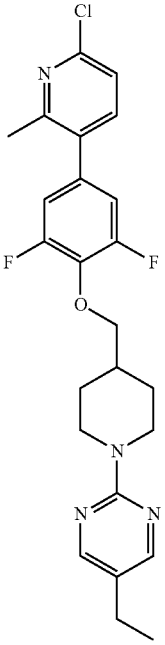 | $^1$H-NMR (400 MHz, CDCl$_3$) δ = 8.20 (s, 2H), 7.46 (d, J = 8.0 Hz, 1H), 7.24 (d, J = 8.0 Hz, 1H), 6.87 (d, J = 8.8 Hz, 2H), 4.80 (d, J = 13.2 Hz, 2H), 4.08 (d, J = 6.8 Hz, 2H), 2.95 (td, J = 12.8, 2.8 Hz, 2H), 2.51 (s, 3H), 2.49 (q, J = 7.6 Hz, 2H), 2.15 (m, 1H), 1.99 (d, J = 13.2 Hz, 2H), 1.58 (s, 3H), 1.39 (qd, J = 12.8, 3.6 Hz, 2H), 1.21 (t, J = 7.6 Hz, 3H); $^{19}$F-NMR (376.5 MHz, CDCl$_3$) δ = −127.15; MS calcd. for [M + H]$^+$ C$_{24}$H$_{26}$ClF$_2$N$_4$O: 459.2, found: 459.2. |

TABLE 1-continued

| Example # | Structure | NMR and/or ESMS |
|---|---|---|
| A24 | 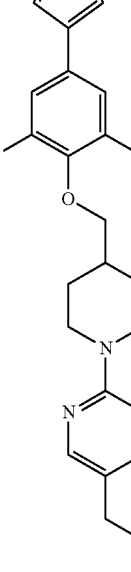 | $^1$H-NMR (400 MHz, CDCl$_3$) δ = 8.10 (s, 2H), 7.60 (s, 1H), 7.47 (s, 1H), 6.90 (d, J = 9.2 Hz, 2H), 4.69 (d, J = 13.2 Hz, 2H), 3.91 (d, J = 6.4 Hz, 2H), 3.87 (s, 3H), 2.85 (td, J = 12.8, 2.8 Hz, 2H), 2.39 (q, J = 7.6 Hz, 2H), 2.02 (m, 1H), 1.89 (d, J = 13.2 Hz, 2H), 1.27 (qd, J = 12.8, 4.0 Hz, 2H), 1.12 (t, J = 7.6 Hz, 3H); $^{19}$F-NMR (376.5 MHz, CDCl$_3$) δ = −128.06; MS calcd. for [M + H]$^+$ C$_{22}$H$_{26}$F$_2$N$_5$O: 414.2, found: 414.2. |
| A25 | 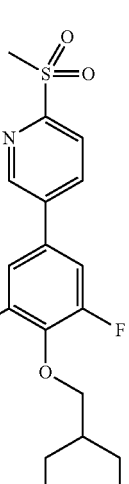 | $^1$H-NMR (400 MHz, CDCl$_3$) δ = 8.79 (dd, J = 2.4, 0.8 Hz, 1H), 8.09 (dd, J = 8.0, 0.8 Hz, 1H), 7.98 (dd, J = 8.0, 2.4 Hz, 1H), 7.10 (d, J = 9.2 Hz, 2H), 4.24-3.97 (br. d, 2H), 3.99 (d, J = 6.4 Hz, 2H), 3.20 (s, 3H), 2.70 (t, J = 12.4 Hz, 2H), 1.95-1.85 (m, 1H), 1.83-1.75 (m, 2H), 1.49 (s, 2H), 1.48 (s, 3H), 1.30-1.16 (m, 2H), 0.82-0.78 (m, 2H), 0.58-0.54 (m, 2H); $^{19}$F-NMR (376.5 MHz, CDCl$_3$) δ = −125.84; MS calcd. for [M + H]$^+$ C$_{23}$H$_{27}$F$_2$N$_2$O$_5$S: 481.2, found: 481.1. |

TABLE 1-continued
| Example # | Structure | NMR and/or ESMS |
|---|---|---|
| A26 | 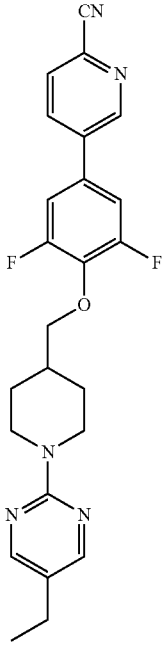 | ¹H-NMR (400 MHz, DMSO-d6) δ = 9.15 (dd, J = 2.4, 0.8 Hz, 1H), 8.41 (dd, J = 8.4, 2.4 Hz, 1H), 8.23 (s, 2H), 8.15 (dd, J = 8.4, 0.8 Hz, 1H), 7.78 (m, 2H), 4.66 (m, 2H), 4.07 (d, J = 6.4 Hz, 2H), 2.87 (m, 2H), 2.42 (q, J = 7.6 Hz, 2H), 2.04 (m, 1H), 1.83 (m, 2H), 1.23 (m, 2H), 1.12 (t, J = 7.6 Hz, 3H); MS calcd. for [M + H]⁺ $C_{24}H_{24}F_2N_5O$: 436.2, found: 436.2. |
| A27 | 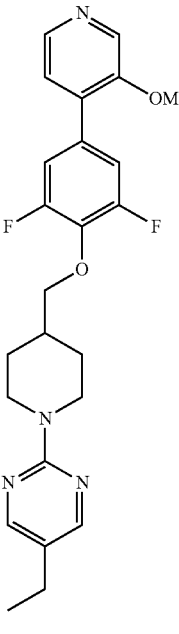 | ¹H-NMR (400 MHz, DMSO-d6) δ = 8.22 (m, 3H), 7.69 (m, 2H), 7.36 (dd, J = 5.6, 1.6 Hz, 1H), 7.18 (dd, J = 1.6, 0.8 Hz, 1H), 4.66 (m, 2H), 4.05 (d, J = 6.4 Hz, 2H), 3.89 (s, 3H), 2.87 (m, 2H), 2.42 (q, J = 7.6 Hz, 2H), 2.03 (m, 1H), 1.83 (m, 2H), 1.23 (m, 2H), 1.12 (t, J = 7.6 Hz, 3H); MS calcd. for [M + H]⁺ $C_{24}H_{27}F_2N_4O_2$: 441.2, found: 441.3. |

TABLE 1-continued
| Example # | Structure | NMR and/or ESMS |
|---|---|---|
| A28 | 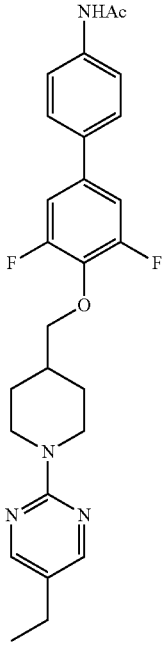 | $^1$H-NMR (400 MHz, DMSO-d6) δ = 10.07 (s, 1H), 8.23 (s, 2H), 7.65 (s, 4H), 7.46 (m, 2H), 4.65 (m, 2H), 4.00 (d, J = 6.4 Hz, 2H), 2.87 (m, 2H), 2.42 (q, J = 7.6 Hz, 2H), 2.06 (s, 3H), 2.02 (m, 1H), 1.83 (m, 2H), 1.23 (m, 2H), 1.12 (t, J = 7.6 Hz, 3H); MS calcd. for [M + H]$^+$ C$_{26}$H$_{29}$F$_2$N$_4$O$_2$: 467.2, found: 467.3. |
| A29 | 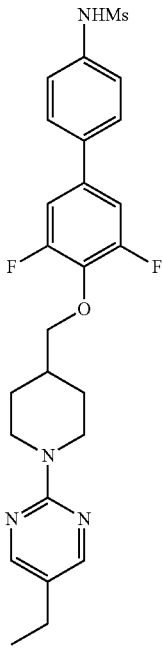 | $^1$H-NMR (400 MHz, DMSO-d6) δ = 9.92 (s, 1H), 8.23 (s, 2H), 7.69 (m, 2H), 7.47 (m, 2H), 7.26 (m, 2H), 4.65 (m, 2H), 4.00 (d, J = 6.3 Hz, 2H), 3.03 (s, 3H), 2.87 (m, 2H), 2.42 (q, J = 7.6 Hz, 2H), 2.03 (m, 1H), 1.83 (m, 2H), 1.22 (m, 2H), 1.12 (t, J = 7.6 Hz, 3H); MS calcd. for [M + H]$^+$ C$_{25}$H$_{29}$F$_2$N$_4$O$_3$S: 503.2, found: 503.3. |

| Example # | Structure | NMR and/or ESMS |
|---|---|---|
| A30 | 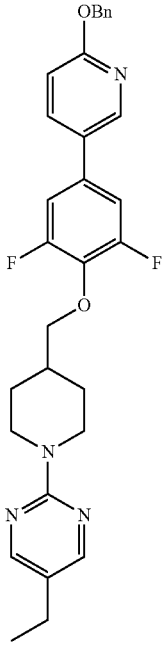 | ¹H-NMR (400 MHz, DMSO-d6) δ = 8.54 (dd, J = 2.8, 0.8 Hz, 1H), 8.23 (s, 2H), 8.08 (dd, J = 8.8, 2.8 Hz, 1H), 7.54 (m, 2H), 7.46 (m, 2H), 7.39 (m, 2H), 7.32 (m, 1H), 6.97 (dd, J = 8.8, 0.8 Hz, 1H), 5.40 (s, 2H), 4.65 (m, 2H), 4.01 (d, J = 6.4 Hz, 2H), 2.87 (m, 2H), 2.42 (q, J = 7.6 Hz, 2H), 2.03 (m, 1H), 1.83 (m, 2H), 1.22 (m, 2H), 1.12 (t, J = 7.6 Hz, 3H); MS calcd. for [M + H]⁺ C₃₀H₃₁F₂N₄O₂: 517.2, found: 517.3. |
| A31 | 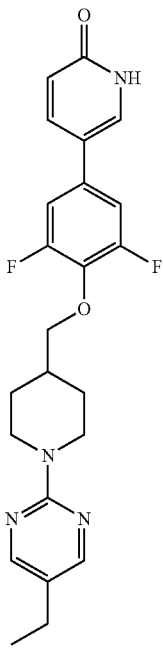 | ¹H-NMR (400 MHz, DMSO-d6) δ = 11.95 (s, 1H), 8.23 (s, 2H), 7.85 (dd, J = 9.6, 2.8 Hz, 1H), 7.81 (d, J = 2.4 Hz, 1H), 7.43 (m, 2H), 6.40 (d, J = 9.6 Hz, 1H), 4.65 (m, 2H), 3.97 (d, J = 6.4 Hz, 2H), 2.87 (m, 2H), 2.41 (q, J = 7.6 Hz, 2H), 2.01 (m, 1H), 1.82 (m, 2H), 1.21 (m, 2H), 1.12 (t, J = 7.6 Hz, 3H); MS calcd. for [M + H]⁺ C₂₃H₂₅F₂N₄O₂: 427.2, found: 427.1. |

TABLE 1-continued
| Example # | Structure | NMR and/or ESMS |
|---|---|---|
| A32 | 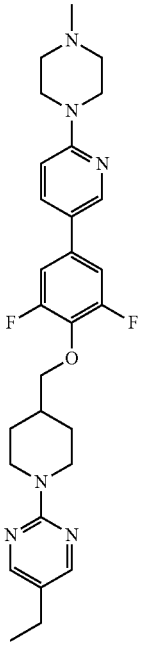 | $^1$H-NMR (400 MHz, DMSO-d6) δ = 8.47 (d, J = 2.4 Hz, 1H), 8.23 (s, 2H), 7.88 (dd, J = 9.2, 2.8 Hz, 1H), 7.46 (m, 2H), 6.89 (d, J = 9.2 Hz, 1H), 4.65 (m, 2H), 3.98 (d, J = 6.4 Hz, 2H), 3.54 (m, 4H), 2.87 (m, 2H), ), 2.41 (m, 6H), 2.21 (s, 3H), 2.02 (m, 1H), 1.83 (m, 2H), 1.23 (m, 2H), 1.12 (t, J = 7.6 Hz, 3H); MS calcd. for [M + H]$^+$ $C_{28}H_{35}F_2N_6O$: 509.3, found: 508.9. |
| A33 | 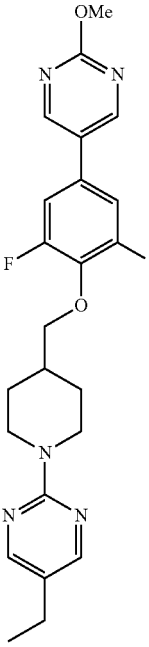 | $^1$H-NMR (400 MHz, DMSO-d6) δ = 8.97 (s, 2H), 8.23 (s, 2H), 7.64 (m, 2H), 4.66 (m, 2H), 4.02 (d, J = 6.4 Hz, 2H), 3.96 (s, 3H), 2.87 (m, 2H), ), 2.42 (q, J = 7.6 Hz, 2H), 2.03 (m, 1H), 1.83 (m, 2H), 1.23 (m, 2H), 1.12 (t, J = 7.6 Hz, 3H); MS calcd. for [M + H]$^+$ $C_{23}H_{26}F_2N_5O_2$: 442.2, found: 442.3. |

TABLE 1-continued

| Example # | Structure | NMR and/or ESMS |
|---|---|---|
| A34 | 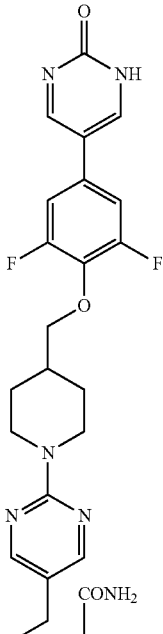 | $^{1}$H-NMR (400 MHz, DMSO-d6) δ = 12.35 (s, 1H), 8.68 (bs, 2H), 8.23 (s, 2H), 7.53 (m, 2H), 4.65 (m, 2H), 3.98 (d, J = 6.4 Hz, 2H), 2.87 (m, 2H), 2.42 (q, J = 7.6 Hz, 2H), 2.01 (m, 1H), 1.83 (m, 2H), 1.22 (m, 2H), 1.12 (t, J = 7.6 Hz, 3H); MS calcd. for [M + H]$^{+}$ C$_{22}$H$_{24}$F$_2$N$_5$O$_2$: 428.2, found: 428.2. |
| A35 | 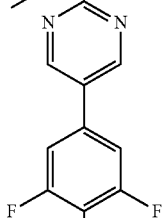 | $^{1}$H-NMR (400 MHz, DMSO-d6) δ = 9.30 (s, 2H), 8.26 (bs, 1H), 8.24 (s, 2H), 7.84 (m, 3H), 4.66 (m, 2H), 4.07 (d, J = 6.4 Hz, 2H), 2.87 (m, 2H), 2.42 (q, J = 7.6 Hz, 2H), 2.04 (m, 1H), 1.84 (m, 2H), 1.24 (m, 2H), 1.12 (t, J = 7.6 Hz, 3H); MS calcd. for [M + H]$^{+}$ C$_{23}$H$_{25}$F$_2$N$_6$O$_2$: 455.2, found: 455.3. |
| A36 | 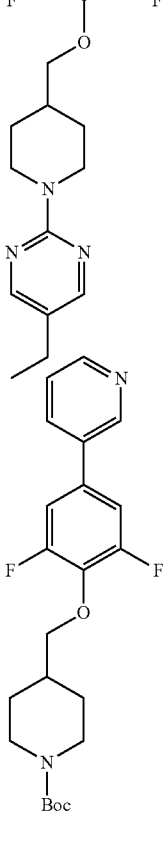 | $^{1}$H-NMR (400 MHz, DMSO-d6) δ = 9.02 (dd, J = 2.4, 0.8 Hz, 1H), 8.67 (dd, J = 5.2, 1.6 Hz, 1H), 8.32 (ddd, J = 8.0, 2.4, 1.6 Hz, 1H), 7.66 (m, 3H), 4.03 (d, J = 6.4 Hz, 2H), 3.97 (m, 2H), 2.74 (m, 2H), 1.91 (m, 1H), 1.75 (m, 2H), 1.39 (s, 9H), 1.17 (m, 2H); MS calcd. for [M + Na]$^{+}$ C$_{22}$H$_{26}$F$_2$N$_2$NaO$_3$: 427.2, found: 427.2. |

TABLE 1-continued
| Example # | Structure | NMR and/or ESMS |
|---|---|---|
| A37 | 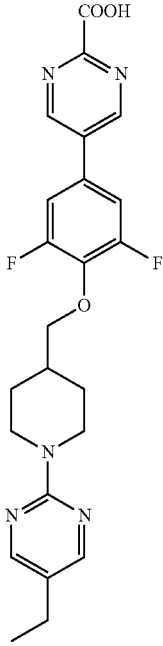 | $^1$H-NMR (400 MHz, DMSO-d6) δ = 9.32 (s 2H), 8.24 (s, 2H), 7.84 (m, 2H), 4.66 (m, 2H), 4.08 (d, J = 6.4 Hz, 2H), 2.88 (m, 2H), 2.42 (q, J = 7.6 Hz, 2H), 2.04 (m, 1H), 1.83 (m, 2H), 1.24 (m, 2H), 1.12 (t, J = 7.6 Hz, 3H); MS calcd. for [M + H]$^+$ C$_{23}$H$_{24}$F$_2$N$_5$O$_3$: 456.2, found: 456.1. |
| A38 | 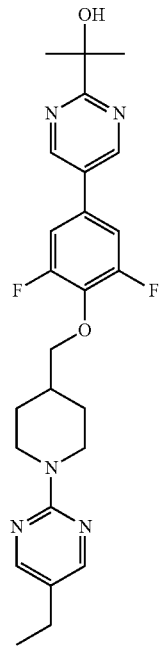 | $^1$H-NMR (400 MHz, DMSO-d6) δ = 8.82 (dd, J = 2.4, 0.8 Hz, 1H), 8.23 (s, 2H), 8.09 (dd, J = 8.4, 2.4 Hz, 1H), 7.71 (dd, J = 8.4, 0.8 Hz, 1H), 7.60 (m, 2H), 5.29 (s, 1H), 4.66 (m, 2H), 4.03 (d, J = 6.4 Hz, 2H), 2.88 (m, 2H), 2.42 (q, J = 7.6 Hz, 2H), 2.03 (m, 1H), 1.84 (m, 2H), 1.46 (s, 6H), 1.23 (m, 2H), 1.12 (t, J = 7.6 Hz, 3H); MS calcd. for [M + H]$^+$ C$_{26}$H$_{31}$F$_2$N$_4$O$_2$: 469.2, found: 469.2. |

TABLE 1-continued
| Example # | Structure | NMR and/or ESMS |
|---|---|---|
| A39 | 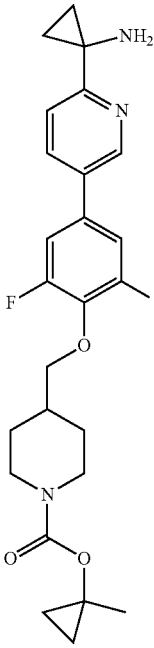 | $^1$H-NMR (400 MHz, DMSO-d6) δ = 8.75 (dd, J = 2.4, 0.8 Hz, 1H), 8.06 (dd, J = 8.4, 2.4 Hz, 1H), 7.82 (dd, J = 8.4, 0.8 Hz, 1H), 7.58 (m, 2H), 4.00 (d, J = 6.4 Hz, 2H), 3.93 (m, 2H), 2.75 (m, 2H), 1.90 (m, 1H), 1.75 (m, 2H), 1.46 (s, 3H), 1.24 (m, 2H), 1.15 (m, 2H), 0.99 (m, 2H), 0.76 (m, 2H), 0.59 (m, 2H); MS calcd. for [M + H]$^+$ C$_{25}$H$_{30}$F$_2$N$_3$O$_3$: 458.2, found: 469.2. |
| A40 | 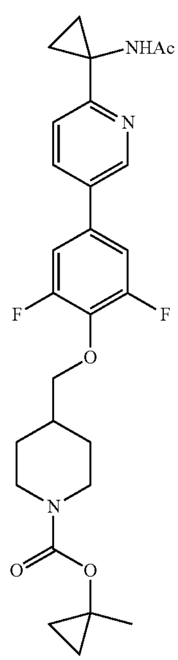 | $^1$H-NMR (400 MHz, DMSO-d6) δ = 8.76 (dd, J = 2.4, 0.8 Hz, 1H), 8.70 (s, 1H), 8.00 (dd, J = 8.4, 2.4 Hz, 1H), 7.56 (m, 2H), 7.36 (d, J = 8.4 Hz, 1H), 4.00 (d, J = 6.4 Hz, 2H), 3.93 (m, 2H), 2.75 (m, 2H), 1.90 (m, 4H), 1.75 (m, 2H), 1.46 (m, 5H), 1.15 (m, 4H), 0.76 (m, 2H), 0.59 (m, 2H); MS calcd. for [M + H]$^+$ C$_{27}$H$_{32}$F$_2$N$_3$O$_4$: 500.2, found: 500.2. |

Example B1
2-(4-((3,5-difluoro-4'-(1H-tetrazol-5-yl)biphenyl-4-yloxy)methyl)piperidin-1-yl)-5-ethylpyrimidine

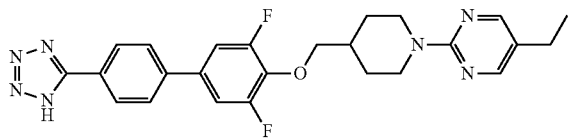

A pressure vessel is charged with Example A8 (73 mg, 0.17 mmol), dibutyltin oxide (7 mg, 15 mol %), azidotrimethylsilane (43 µL, 0.17 mmol), and dry toluene (3 mL). The vessel is sealed and heated to 110° C. for 24 h. The solution is allowed to cool to rt and purified by flash chromatography (CH$_2$Cl$_2$/MeOH gradient) to afford the title compound (Example B1) as an off-white powder: $^1$H-NMR (400 MHz, DMSO-D$_6$) δ=8.28 (s, 2H), 8.16 (d, J=8.4 Hz, 2H), 8.02 (d, J=8.4 Hz, 2H), 7.70 (d, J=9.6 Hz, 2H), 4.71 (d, J=13.0 Hz, 2H), 4.09 (d, J=6.4 Hz, 2H), 2.93 (td, J=12.8, 2.4 Hz, 2H), 2.47 (q, J=7.6 Hz, 2H), 2.09 (m, 1H), 1.89 (dd, J=12.8, 2.4 Hz, 2H), 1.29 (qd, J=12.8, 3.6 Hz, 2H), 1.17 (t, J=7.6 Hz, 3H); $^{19}$F-NMR (376.5 MHz, DMSO-D$_6$) δ=−127.54; MS calcd. for [M+H]$^+$ C$_{25}$H$_{26}$F$_2$N$_7$O: 478.2. found: 478.2.

By repeating the procedure described in the above Example B1, using appropriate starting materials, the following compounds of Formula I, as identified in Table 2, are obtained:

TABLE 2

| Example # | Structure | NMR and/or ESMS |
| --- | --- | --- |
| B2 | 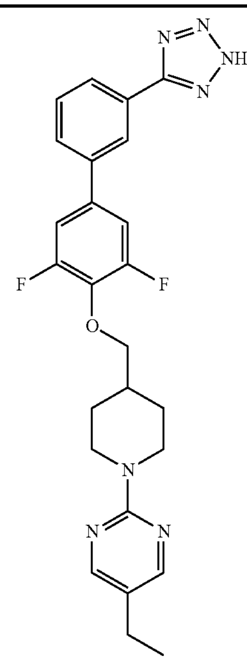 | $^1$H-NMR (400 MHz, DMSO-D$_6$) δ = 8.33 (t, J = 1.6 Hz, H), 8.23 (s, 2H), 8.06 (ddd, J = 7.6, 1.6, 1.2 Hz, 1H), 7.94 (ddd, J = 7.6, 1.6, 1.2 Hz, 1H), 7.70 (t, J = 7.7 Hz, 1H), 7.62 (d, J = 9.6 Hz, 2H), 4.67 (d, J = 13.2 Hz, 2H), 4.05 (d, J = 6.4 Hz, 2H), 2.89 (td, J = 12.8, 2.0 Hz, 2H), 2.42 (q, J = 7.6 Hz, 2H), 2.05 (m, 1H), 1.85 (d, J = 13.2 Hz, 2H), 1.24 (qd, J = 12.4, 3.6 Hz, 2H), 1.13 (t, J = 7.6 Hz, 3H); $^{19}$F-NMR (376.5 MHz, DMSO-D$_6$) δ = −127.49; MS calcd. for [M + H]$^+$ C$_{25}$H$_{26}$F$_2$N$_7$O: 478.2, found: 478.2. |
| B3 | 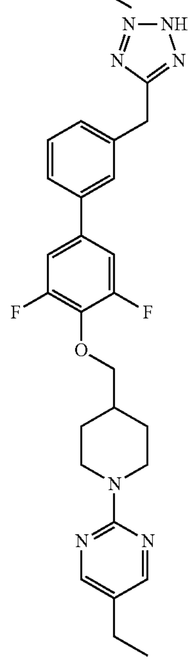 | $^1$H-NMR (400 MHz, DMSO-D$_6$) δ = 8.24 (s, 2H), 7.68 (t, J = 1.6 Hz, 1H), 7.61 (ddd, J = 7.6, 1.6, 1.2 Hz, 1H), 7.50 (d, J = 9.6 Hz, 2H), 7.42 (t, J = 7.6 Hz, 1H), 7.27 (ddd, J = 7.6, 1.6, 1.2 Hz, 1H), 4.66 (d, J = 13.2 Hz, 2H), 4.35 (s, 2H), 4.02 (d, J = 6.4 Hz, 2H), 2.88 (td, J = 12.8, 2.4 Hz, 2H), 2.42 (q, J = 7.6 Hz, 2H), 2.04 (m, 1H), 1.84 (d, J = 13.2 Hz, 2H), 1.25 (qd, J = 11.6, 3.6 Hz, 2H), 1.12 (t, J = 7.6 Hz, 3H); $^{19}$F-NMR (376.5 MHz, DMSO-D$_6$) δ = −127.79; MS calcd. for [M + H]$^+$ C$_{26}$H$_{28}$F$_2$N$_7$O: 492.2, found: 492.2. |

TABLE 2-continued
| Example # | Structure | NMR and/or ESMS |
|---|---|---|
| B4 | 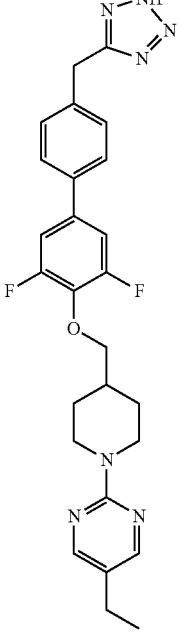 | $^1$H-NMR (400 MHz, DMSO-D$_6$) δ = 8.23 (s, 2H), 7.68 (d, J = 8.4 Hz, 2H), 7.50 (d, J = 10.0 Hz, 2H), 7.35 (d, J = 8.4 Hz, 2H), 4.65 (d, J = 13.2 Hz, 2H), 4.33 (s, 2H), 4.01 (d, J = 6.4 Hz, 2H), 2.87 (td, J = 12.4, 2.4 Hz, 2H), 2.42 (q, J = 7.6 Hz, 2H), 2.03 (m, 1H), 1.83 (d, J = 12.8 Hz, 2H), 1.23 (qd, J = 12.4, 3.8 Hz, 2H), 1.12 (t, J = 7.6 Hz, 3H); $^{19}$F-NMR (376.5 MHz, DMSO-D$_6$) δ = −127.83; MS calcd. for [M + H]$^+$ C$_{26}$H$_{28}$F$_2$N$_7$O: 492.2, found: 492.3. |
| B5 | 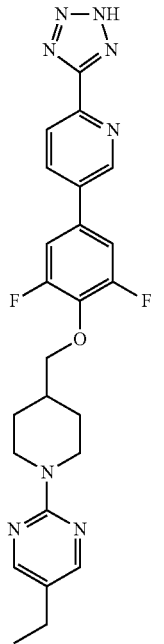 | $^1$H-NMR (400 MHz, DMSO-d6) δ = 9.16 (dd, J = 2.4, 0.8 Hz, 1H), 8.42 (dd, J = 8.4, 2.4 Hz, 1H), 8.28 (dd, J = 8.4, 0.8 Hz, 1H), 8.25 (s, 2H), 7.79 (m, 2H), 4.66 (m, 2H), 4.07 (d, J = 6.4 Hz, 2H), 2.89 (m, 2H), ), 2.42 (q, J = 7.6 Hz, 2H), 2.05 (m, 1H), 1.84 (m, 2H), 1.25 (m, 2H), 1.13 (t, J = 7.6 Hz, 3H); MS calcd. for [M + H]$^+$ C$_{24}$H$_{25}$F$_2$N$_8$O: 479.2, found: 479.3. |

Examples C1 and C2

2-(4-((3,5-difluoro-4'-(2-methyl-2H-tetrazol-5-yl)biphenyl-4-yloxy)methyl)piperidin-1-yl)-5-ethylpyrimidine 2-(4-((3,5-difluoro-4'-(1-methyl-1H-tetrazol-5-yl)biphenyl-4-yloxy)methyl)piperidin-1-yl)-5-ethylpyrimidine

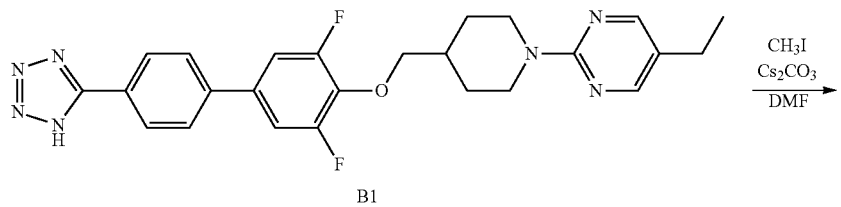

B1

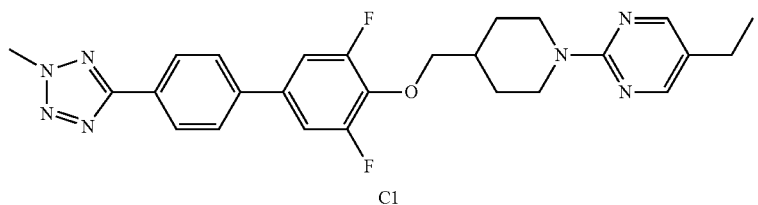

C1

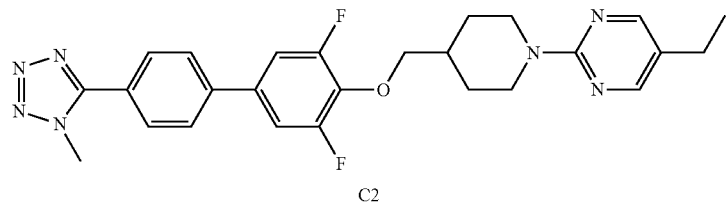

C2

To a solution of Example B1 (20 mg, 0.04 mmol) and methyl iodide (10 μL, 0.16 mmol) in DMF (3 mL) is added $Cs_2CO_3$ (40 mg, 0.12 mmol). The resulting suspension is heated to 80° C. for 1 h, cooled to rt, and diluted with $H_2O$ (20 mL). The mixture is extracted with EtOAc (2×20 mL), and the combined organics are washed with brine, dried over $MgSO_4$, and concentrated in vacuo. Purification by flash chromatography (EtOAc/hexanes gradient) afford the title compounds (Example C1) and (Example C2) as white solids.

C1: $^1$H-NMR (400 MHz, $CDCl_3$) δ=8.13 (d, J=8.4 Hz, 2H), 8.11 (s, 2H), 7.57 (d, J=8.4 Hz, 2H), 7.12 (d, J=9.6 Hz, 2H), 4.70 (d, J=13.2 Hz, 2H), 4.35 (s, 3H), 3.98 (d, J=6.8 Hz, 2H), 2.86 (td, J=13.2, 2.0 Hz, 2H), 2.39 (q, J=7.6 Hz, 2H), 2.05 (m, 1H), 1.91 (d, J=13.2 Hz, 2H), 1.30 (m, 2H), 1.12 (t, J=7.6 Hz, 3H); $^{19}$F-NMR (376.5 MHz, $CDCl_3$) δ=−127.46; MS calcd. for $[M+H]^+$ $C_{26}H_{28}F_2N_7O$: 492.2. found: 492.3.

C2: $^1$H-NMR (400 MHz, $CDCl_3$) δ=8.11 (s, 2H), 7.77 (d, J=8.4 Hz, 2H), 7.64 (d, J=8.4 Hz, 2H), 7.12 (d, J=9.2 Hz, 2H), 4.71 (d, J=13.2 Hz, 2H), 4.16 (s, 3H), 3.99 (d, J=6.8 Hz, 2H), 2.86 (td, J=13.2, 2.0 Hz, 2H), 2.39 (q, J=7.6 Hz, 2H), 2.05 (m, 1H), 1.91 (d, J=13.2 Hz, 2H), 1.30 (m, 2H), 1.12 (t, J=7.6 Hz, 3H); $^{19}$F-NMR (376.5 MHz, $CDCl_3$) δ=−126.93; MS calcd. for $[M+H]+C_{26}H_{28}F_2N_7O$: 492.2. found: 492.2.

By repeating the procedures described in the above Examples $C_1$-$C_2$, using appropriate starting materials, the following compounds of Formula I, as identified in Table 3, are obtained:

TABLE 3
| Example # | Structure | NMR and/or ESMS |
|---|---|---|
| C3 | 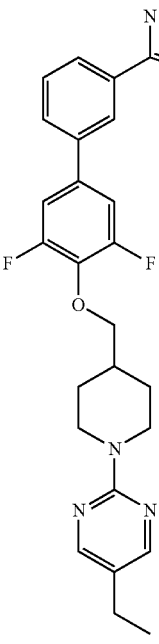 | $^1$H-NMR (400 MHz, CDCl$_3$) δ = 8.30 (t, J = 1.6 Hz, 1H), 8.17 (s, 2H), 8.13 (dt, J = 7.6, 1.6 Hz, 1H), 7.61 (dt, J = 7.6, 1.6 Hz, 1H), 7.56 (t, J = 7.6 Hz, 1H), 7.22 (d, J = 9.2 Hz, 2H), 4.78 (d, J = 13.2 Hz, 2H), 4.43 (s, 3H), 4.05 (d, J = 6.4 Hz, 2H), 2.93 (t, J = 12.8 Hz, 2H), 2.46 (q, J = 7.6 Hz, 2H), 2.12 (m, 1H), 1.98 (d, J = 12.8 Hz, 2H), 1.37 (qd, J = 12.4, 3.4 Hz, 2H), 1.19 (t, J = 7.6 Hz, 3H); MS calcd. for [M + H]$^+$ C$_{26}$H$_{28}$F$_2$N$_7$O: 492.2, found: 492.2. |
| C4 | 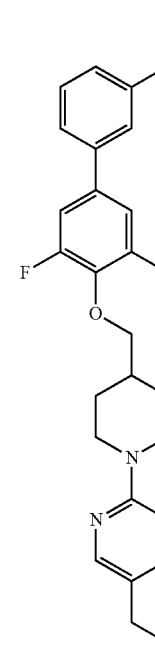 | $^1$H-NMR (400 MHz, CDCl$_3$) δ = 8.17 (s, 2H), 7.90 (s, 1H), 7.71 (m, 2H), 7.65 (t, J = 7.6 Hz, 1H), 7.17 (d, J = 9.2 Hz, 2H), 4.77 (d, J = 13.2 Hz, 2H), 4.22 (s, 3H), 4.06 (d, J = 6.4 Hz, 2H), 2.92 (td, J = 12.8, 2.4 Hz, 2H), 2.46 (t, J = 7.6 Hz, 2H), 2.11 (m, 1H), 1.97 (d, J = 12.8 Hz, 2H), 1.36 (qd, J = 12.8, 4.0 Hz, 2H), 1.18 (t, J = 7.6 Hz, 3H); MS calcd. for [M + H]$^+$ C$_{26}$H$_{28}$F$_2$N$_7$O: 492.2, found: 492.2. |

TABLE 3-continued

| Example # | Structure | NMR and/or ESMS |
|---|---|---|
| C5 | 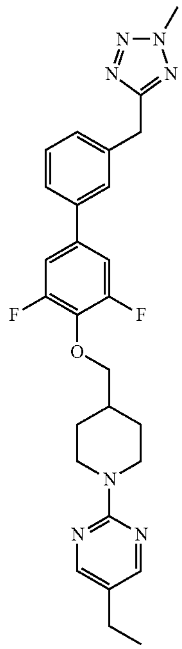 | $^1$H-NMR (400 MHz, CDCl$_3$) δ = 8.17 (s, 2H), 7.46 (s, 1H), 7.38 (m, 2H), 7.32 (m, 1H), 7.10 (d, J = 9.6 Hz, 2H), 4.76 (d, J = 13.2 Hz, 2H), 4.31 (s, 3H), 4.28 (s, 2H), 4.02 (d, J = 6.4 Hz, 2H), 2.92 (td, J = 12.8, 2.8 Hz, 2H), 2.46 (q, J = 7.6 Hz, 2H), 2.10 (m, 1H), 1.97 (d, J = 13.2 Hz, 2H), 1.35 (qd, J = 12.4, 4.0 Hz, 2H), 1.18 (t, J = 7.6 Hz, 3H); MS calcd. for [M + H]$^+$ C$_{27}$H$_{30}$F$_2$N$_7$O: 506.2, found: 506.3. |
| C6 | 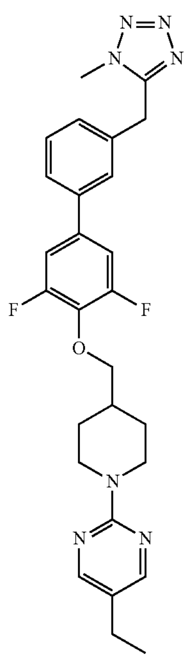 | $^1$H-NMR (400 MHz, CDCl$_3$) δ = 8.17 (s, 2H), 7.42 (m, 2H), 7.34 (s, 1H), 7.18 (d, J = 6.8 Hz, 1H), 7.07 (d, J = 9.2 Hz, 2H), 4.76 (d, J = 13.2 Hz, 2H), 4.35 (s, 2H), 4.02 (d, J = 6.4 Hz, 2H), 3.89 (s, 3H), 2.92 (td, J = 12.8, 2.4 Hz, 2H), 2.45 (q, J = 7.6 Hz, 2H), 2.10 (m, 1H), 1.96 (d, J = 13.2 Hz, 2H), 1.35 (qd, J = 12.4, 4.0 Hz, 2H), 1.18 (t, J = 7.6 Hz, 3H); MS calcd. for [M + H]$^+$ C$_{27}$H$_{30}$F$_2$N$_7$O: 506.2, found: 506.3. |

TABLE 3-continued

| Example # | Structure | NMR and/or ESMS |
|---|---|---|
| C7 | 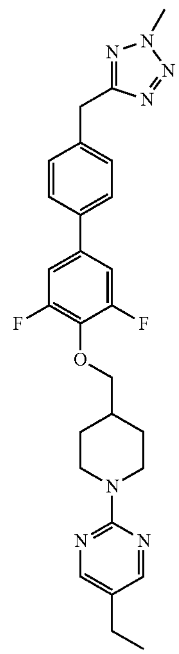 | ¹H-NMR (400 MHz, CDCl₃) δ = 8.17 (s, 2H), 7.45 (d, J = 8.4 Hz, 2H), 7.39 (d, J = 8.4 Hz, 2H), 7.09 (d, J = 9.2 Hz, 2H), 4.76 (d, J = 13.2 Hz, 2H), 4.31 (s, 3H), 4.27 (s, 2H), 4.01 (d, J = 6.4 Hz, 2H), 2.92 (td, J = 12.8, 2.8 Hz, 2H), 2.46 (q, J = 7.6 Hz, 2H), 2.10 (m, 1H), 1.96 (d, J = 13.2 Hz, 2H), 1.35 (qd, J = 12.4, 4.0 Hz, 2H), 1.18 (t, J = 7.6 Hz, 3H); MS calcd. for [M + H]⁺ C₂₇H₃₀F₂N₇O: 506.2, found: 506.3. |
| C8 | 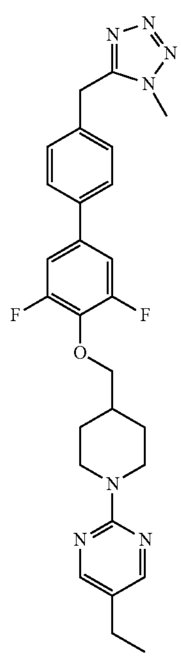 | ¹H-NMR (400 MHz, CDCl₃) δ = 8.17 (s, 2H), 7.48 (d, J = 8.4 Hz, 2H), 7.26 (d, J = 8.4 Hz, 2H), 7.09 (d, J = 9.2 Hz, 2H), 4.76 (d, J = 13.2 Hz, 2H), 4.33 (s, 2H), 4.02 (d, J = 6.4 Hz, 2H), 3.89 (s, 3H), 2.92 (td, J = 12.8, 2.0 Hz, 2H), 2.46 (q, J = 7.6 Hz, 2H), 2.10 (m, 1H), 1.96 (d, J = 12.8 Hz, 2H), 1.35 (qd, J = 12.4, 4.0 Hz, 2H), 1.18 (t, J = 7.6 Hz, 3H); MS calcd. for [M + H]⁺ C₂₇H₃₀F₂N₇O: 506.2, found: 506.3. |

TABLE 3-continued
| Example # | Structure | NMR and/or ESMS |
|---|---|---|
| C9 | 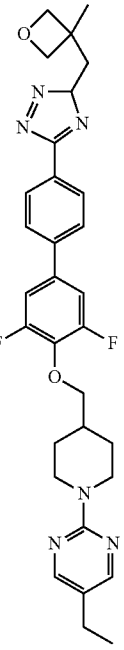 | $^1$H-NMR (400 MHz, CDCl$_3$) δ = 8.21 (d, J = 8.4 Hz, 2H), 8.17 (s, 2H), 7.64 (d, J = 8.4 Hz, 2H), 7.19 (d, J = 9.2 Hz, 2H), 4.91 (s, 2H), 4.80 (d, J = 6.4 Hz, 2H), 4.77 (d, J = 13.2 Hz, 2H), 4.50 (d, J = 6.4 Hz, 2H), 4.05 (d, J = 6.4 Hz, 2H), 2.93 (td, J = 12.8, 2.4 Hz, 2H), 2.46 (q, J = 7.6 Hz, 2H), 2.11 (m, 1H), 1.97 (d, J = 13.2 Hz, 2H), 1.36 (qd, J = 12.4, 4.0 Hz, 2H), 1.33 (s, 3H), 1.18 (t, J = 7.6 Hz, 3H); MS calcd. for [M + H]$^+$ C$_{30}$H$_{34}$F$_2$N$_7$O$_2$: 562.3, found: 562.3. |
| C10 | 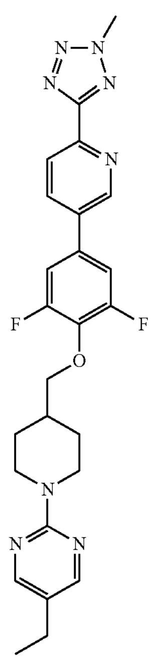 | $^1$H-NMR (400 MHz, DMSO-d6) δ = 9.12 (dd, J = 2.4, 0.8 Hz, 1H), 8.35 (dd, J = 8.4, 2.4 Hz, 1H), 8.24 (s, 2H), 8.18 (dd, J = 8.4, 0.8 Hz, 1H), 7.75 (m, 2H), 4.67 (m, 2H), 4.47 (s, 3H), 4.06 (d, J = 6.4 Hz, 2H), 2.88 (m, 2H), 2.42 (q, J = 7.6 Hz, 2H), 2.04 (m, 1H), 1.84 (m, 2H), 1.24 (m, 2H), 1.13 (t, J = 7.6 Hz, 3H); MS calcd. for [M + H]$^+$ C$_{25}$H$_{27}$F$_2$N$_8$O: 493.2, found: 493.2. |

TABLE 3-continued

| Example # | Structure | NMR and/or ESMS |
|---|---|---|
| C11 | 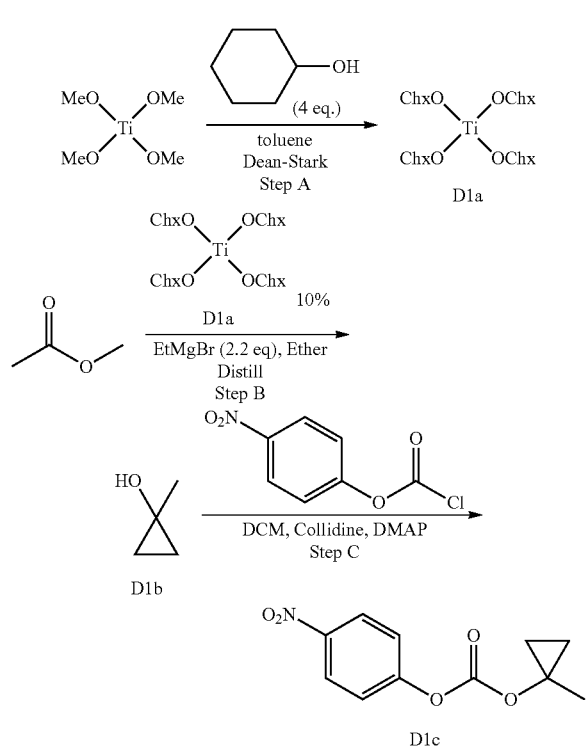 | $^1$H-NMR (400 MHz, DMSO-d6) δ = 9.20 (dd, J = 2.4, 0.8 Hz, 1H), 8.44 (dd, J = 8.4, 2.4 Hz, 1H), 8.30 (dd, J = 8.4, 0.8 Hz, 1H), 8.24 (s, 2H), 7.78 (m, 2H), 4.67 (m, 2H), 4.45 (s, 3H), 4.07 (d, J = 6.4 Hz, 2H), 2.88 (m, 2H), 2.42 (q, J = 7.6 Hz, 2H), 2.05 (m, 1H), 1.84 (m, 2H), 1.24 (m, 2H), 1.13 (t, J = 7.6 Hz, 3H); MS calcd. for [M + H]$^+$ $C_{25}H_{27}F_2N_8O$: 493.2, found: 493.2. |

Example D1

1-methylcyclopropyl 4-((3,5-difluoro-4'-(methylsulfonyl)biphenyl-4-yloxy)methyl)piperidine-1-carboxylate

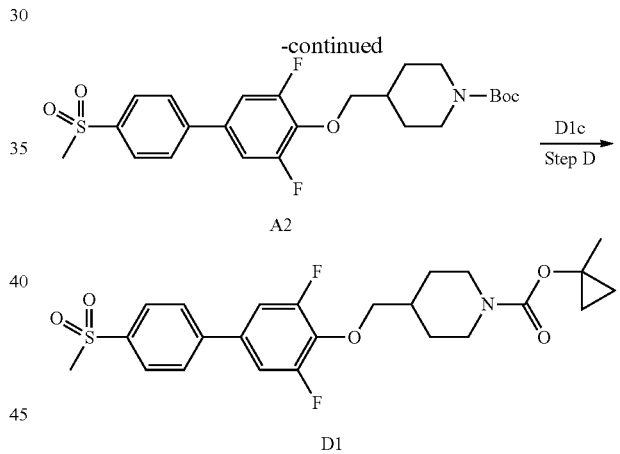

Step A: A 25 mL flask is charged with Ti(OMe)$_4$ (3.25 g, 18.9 mmol) and cyclohexanol (7.57 g, 75.6 mL) and toluene (15 mL). The system is heated to 140° C. with a Dean-Stark trap until no more MeOH is generated, then the toluene is removed to afford the titanium cyclohexyloxy catalyst D1a. This cycle is repeated twice and the remainder is used without further purification.

Step B: A 2 L flask is treated with ether (500 mL), all of the above catalyst D1a and methyl acetate (14 g, 0.189 mol). To this solution is added a 3 M solution of ethyl magnesium bromide in diethyl ether (139 mL, 0.416 mol) over the course of 1.5 h. The temperature is kept constant by suspending the flask in a water bath. After the addition is complete, the reaction mixture is stirred for an additional 15 min and then quenched into an ice cold solution of 10% H$_2$SO$_4$ in water (1.6 L). The organic phase is separated and the aqueous phase is extracted with ether (2×250 mL). The combined organics are extracted with saturated aqueous sodium hydrogencarbonate (50 mL), dried over MgSO$_4$ and filtered. The ether is removed without vacuum at 65° C. and the residue is distilled through a short path distillation apparatus. The desired 1-methylcyclopropanol D1b boils at roughly 100° C. Once the product fraction (5.0 g) is collected, it is examined by NMR and the rough purity is 50% with the rest of the material being toluene, ether and methyl ethyl ketone. This material is used in the next step without further purification.

Step C: An ice cold solution of 4-nitrophenyl chloroformate (6.99 g, 34 mmol) in $CH_2Cl_2$ (50 mL) is treated with the entire solution of D1b from the previous step along with DMAP (424 mg, 3.47 mmol) in 2,4,6-collidine (25 mL) and stirred in an ice/water bath for 30 min. The ice bath is removed and the reaction mixture is allowed to stir overnight. The reaction mixture is then treated with 1 M HCl (150 mL). The organics are isolated and extracted once with 1 M HCl (100 mL) and once with saturated aqueous NaCl (20 mL). The organics are dried over $MgSO_4$, filtered, concentrated and purified by flash chromatography (EtOAc/hexanes gradient) to afford 1-methylcyclopropyl 4-nitrophenyl carbonate D1c as an oil which solidifies after prolonged standing: $^1$H NMR ($CDCl_3$) δ=8.28 (m, 2H), 7.38 (m, 2H), 1.66 (s, 3H), 1.07 (m, 2H), 0.76 (m, 2H); MS calcd. for $[M+H]^+$ $C_{11}H_{12}NO_5$: 238.1. found: 237.8.

flash chromatography ($SiO_2$, EtOAc/hexanes gradient) affords the title compound (Example D1) as a white solid: $^1$H-NMR (400 MHz, $CD_3CN$) δ=8.01 (d, J=8.8 Hz, 2H), 7.86 (d, J=8.8 Hz, 2H), 7.45-7.38 (m, 2H), 4.11-3.94 (m, 2H), 4.07 (d, J=6.0 Hz, 2H), 3.12 (s, 3H), 2.86-2.68 (m, 2H), 2.02-2.00 (m, 1H), 1.85-1.81 (m, 2H), 1.51 (s, 3H), 1.29-1.19 (m, 2H), 0.84-0.81 (m, 2H), 0.63-0.60 (m, 2H); $^{19}$F-NMR (376.5 MHz, $CD_3CN$) δ=−128.76; MS calcd. for $[M+H]^+$ $C_{24}H_{28}F_2NO_5S$: 480.1. found: 480.1.

Examples E1-E3

4-(4-((1-(tert-butoxycarbonyl)piperidin-4-yl)methoxy)-3,5-difluorophenyl)pyridine 1-oxide tert-butyl 4-((2,6-difluoro-4-(2-oxo-1,2-dihydropyridin-4-yl)phenoxy)methyl)piperidine-1-carboxylate tert-butyl 4-((2,6-difluoro-4-(1-methyl-2-oxo-1,2-dihydropyridin-4-yl)phenoxy)methyl)piperidine-1-carboxylate

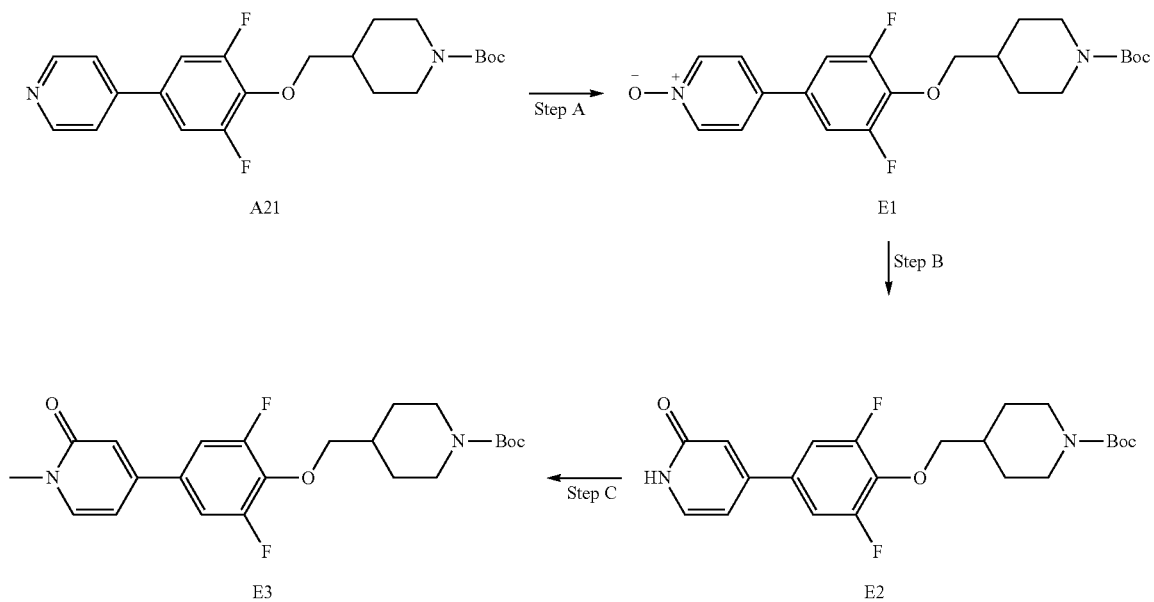

Step D: Example A2 (61 mg, 0.13 mmol) is dissolved in $CH_2Cl_2$ (3 mL), cooled to 0° C. and treated with trifluoroacetic acid (0.3 mL). The mixture is then stirred at rt for 2 h. The solvent is removed and the residue coevaporated with toluene once. The residue is dissolved in $CH_2Cl_2$ (3 mL), treated with $NEt_3$ (0.3 mL) and Intermediate D1c (30 mg, 0.13 mmol) and stirred at rt overnight. The mixture is diluted with $CH_2Cl_2$, washed with 1N NaOH (3×), 1M HCl (1×) and brine (1×), dried ($Na_2SO_4$) and concentrated in vacuo. Purification by Step A: A solution of mCPBA (77%, 350 mg, 1.56 mmol) in EtOAc (1 mL) is added to a solution of Example A21 (162 mg, 0.4 mmol) in EtOAc (2 mL) and stirred at rt overnight. EtOAc (20 mL) is added and washed with aq. $NaHCO_3$ (2×20 mL). The organic phase is dried ($Na_2SO_4$) and concentrated in vacuo. Purification by flash chromatography ($CH_2Cl_2$/MeOH gradient) affords Example E1 as an off-white solid: $^1$H-NMR (400 MHz, DMSO-d6) δ=8.27 (m, 2H), 7.69 (m, 2H), 7.82 (m, 2H), 7.70 (m, 2H), 4.03 (d, J=6.4 Hz, 2H), 3.97

(m, 2H), 2.73 (m, 2H), 1.90 (m, 1H), 1.75 (m, 2H), 1.39 (s, 9H), 1.16 (m, 2H); MS calcd. for $[M+H]^+$ $C_{22}H_{27}F_2N_2O_4$: 421.2. found: 421.2.

Step B: A solution of Example E1 (66 mg, 0.16 mmol) in $Ac_2O$ (2 mL) is heated at 130° C. for 20 h. Then, the reaction mixture is concentrated, dissolved in MeOH (4 mL) and 2M $Na_2CO_3$ (2 mL) and stirred at rt overnight. The solvent is removed in vacuo and $H_2O$ (20 mL) is added. The reaction mixture is extracted with EtOAc (3×10 mL), washed with $H_2O$ (10 mL), dried ($Na_2SO_4$) and concentrated in vacuo. Purification by flash chromatography ($CH_2Cl_2$/MeOH gradient) affords Example E2 as a white solid: $^1$H-NMR (400 MHz, DMSO-d6) δ=7.59 (m, 2H), 7.44 (d, J=6.8, 1H), 6.67 (d, J=1.6 Hz, 1H), 6.53 (dd, J=6.8, 1.6 Hz, 1H), 4.03 (d, J=6.4 Hz, 2H), 3.97 (m, 2H), 2.73 (s, 2H), 1.90 (m, 1H), 1.75 (m, 2H), 1.39 (s, 9H), 1.16 (m, 2H); MS calcd. for $[M+H]^+$ $C_{22}H_{27}F_2N_2O_4$: 421.2. found: 421.2.

Step C: To a solution of Example E2 (21 mg, 0.05 mmol) in anhydrous DMF (0.2 mL) are added $Cs_2CO_3$ (49 mg, 0.15 mmol) and MeI (20 μL, 0.15 mmol). The mixture is heated in a sealed vial at 65° C. overnight, then purified on a reversed phase HPLC($H_2O$/MeCN gradient) to provide the title compound Example E3 as a white solid: $^1$H-NMR (400 MHz, DMSO-d6) δ=7.78 (d, J=7.2, 1H), 7.61 (m, 2H), 6.76 (d, J=2.1 Hz, 1H), 6.61 (dd, J=7.2, 2.4 Hz, 1H), 4.03 (d, J=6.4 Hz, 2H), 3.97 (m, 2H), 3.43 (s, 3H), 2.73 (s, 2H), 1.89 (m, 1H), 1.75 (m, 2H), 1.39 (s, 9H), 1.15 (m, 2H); MS calcd. for $[M+H]^+$ $C_{23}H_{29}F_2N_2O_4$: 435.2. found: 434.9.

Example F1

2-(4-((2,6-difluoro-4-(2-methyl-6-(1H-1,2,4-triazol-1-yl)pyridin-3-yl)phenoxy)methyl)piperidin-1-yl)-5-ethylpyrimidine Step A: In a 4 mL vial, Example A23 (108 mg, 0.23 mmol) and sodium iodide (110 mg, 0.73 mmol) are suspended in dry $CH_3CN$ (2 mL). Acetyl chloride (35 uL, 0.49 mmol) is added, the vial is sealed, and the mixture is heated to 80° C. for 24 h, then allowed to cool to rt. The suspension is diluted with an aqueous solution of 10% $K_2CO_3$ and 5% $NaHSO_3$ and extracted twice with $CH_2Cl_2$. The organics are dried ($MgSO_4$) and concentrated in vacuo to afford the crude 2-(4-((2,6-difluoro-4-(6-iodo-2-methylpyridin-3-yl)phenoxy)methyl)piperidin-1-yl)-5-ethylpyrimidine F1a, which is used without further purification: MS calcd. for $[M+H]^+$ $C_{24}H_{26}F_{21}N_4O$: 551.1. found: 551.2.

Step B: The crude Intermediate F1a (40 mg, ca. 0.05 mmol), $[Cu(I)OTf]_2Ph$ (2.6 mg, 0.005 mmol), 1H-1,2,4-triazole (8 mg, 0.11 mmol), and cesium carbonate (45 mg, 0.14 mmol) are dissolved in dry DMSO (1 mL). Dimethyl ethylenediamine (1 μL, 0.013 mmol) is added and the solution is heated to 120° C. for 5 h. After cooling to rt, the mixture is diluted with $H_2O$ (30 mL) and extracted twice with EtOAc. The organics are dried ($MgSO_4$), concentrated in vacuo, and purified by flash chromatography (EtOAc/hexanes gradient) to afford the title compound (Example F1) as a white solid: $^1$H-NMR (400 MHz, CDCl$_3$) δ=9.21 (s, 1H), 8.18 (s, 2H), 8.10 (s, 1H), 7.77 (d, J=8.4 Hz, 1H), 7.67 (d, J=8.4 Hz, 1H), 6.89 (d, J=8.8 Hz, 2H), 4.78 (d, J=13.1 Hz, 1H), 4.06 (d, J=6.4 Hz, 2H), 2.93 (td, J=12.8, 2.4 Hz, 2H), 2.54 (s, 3H), 2.46 (q, J=7.5 Hz, 2H), 2.13 (m, 1H), 1.98 (d, J=13.2 Hz, 2H), 1.37 (qd, J=12.8, 4.0 Hz, 2H), 1.19 (t, J=7.6 Hz, 3H); $^{19}$F-NMR (376.5 MHz, CDCl$_3$) δ=−127.22; MS calcd. for $[M+H]^+$ $C_{26}H_{28}F_2N_7O$: 492.2. found: 492.2.

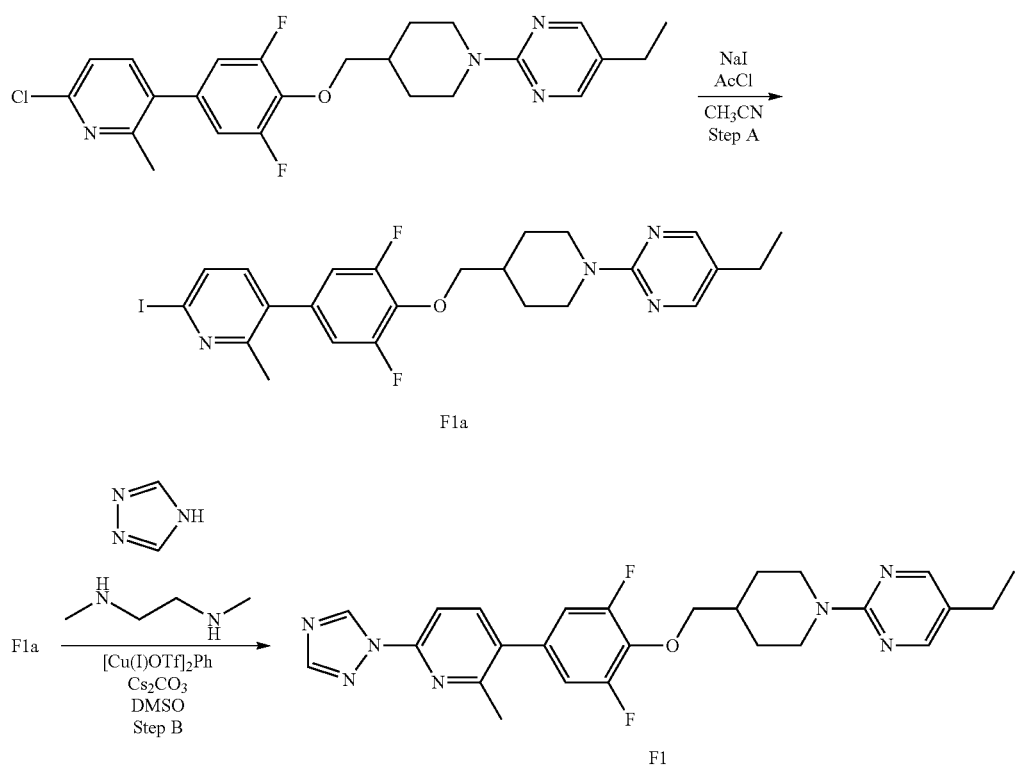

Example F2

2-(4-((2,6-difluoro-4-(2-methyl-6-(methylsulfonyl)pyridin-3-yl)phenoxy)methyl)piperidin-1-yl)-5-ethylpyrimidine

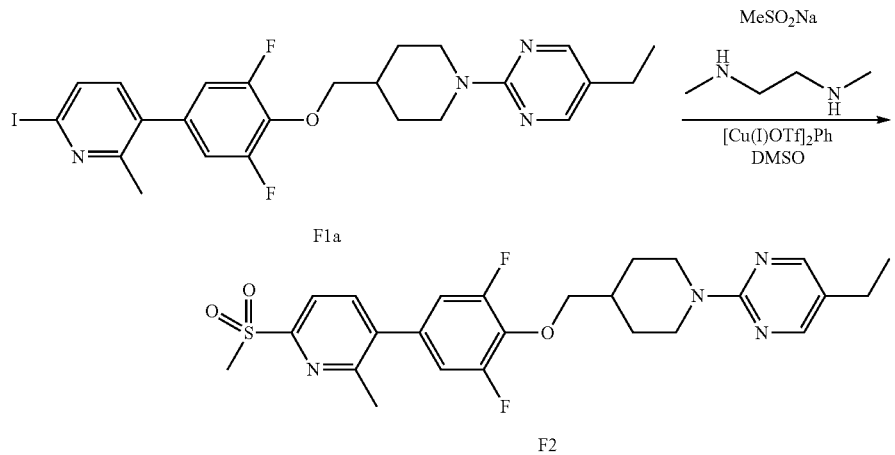

The crude Intermediate F1a (40 mg, ca. 0.05 mmol) is treated as described for Example F1, using sodium methanesulfinate instead of 1H-1,2,4-triazole and omitting the addition of cesium carbonate, to afford the title compound (Example F2) as a white solid: $^1$H-NMR (400 MHz, CDCl$_3$) δ=8.17 (s, 2H), 7.97 (d, J=7.6 Hz, 1H), 7.73 (d, J=7.6 Hz, 1H), 6.88 (d, J=8.8 Hz, 2H), 4.78 (d, J=13.2 Hz, 2H), 4.07 (d, J=6.4 Hz, 2H), 3.27 (s, 3H), 2.93 (td, J=12.8, 2.8 Hz, 2H), 2.59 (s, 3H), 2.46 (q, J=7.6 Hz, 2H), 2.13 (m, 1H), 1.97 (d, J=13.2 Hz, 2H), 1.37 (qd, J=12.8, 4.4 Hz, 2H), 1.18 (t, J=7.6 Hz, 3H); $^{19}$F-NMR (376.5 MHz, CDCl$_3$) δ=−126.57; MS calcd. for [M+H]$^+$ C$_{25}$H$_{29}$F$_2$N$_4$O$_3$S: 503.2. found: 503.3.

Example F3

1-methylcyclopropyl 4-((2,6-difluoro-4-(2-methyl-6-(methylsulfonyl)pyridin-3-yl)phenoxy)methyl)piperidine-1-carboxylate

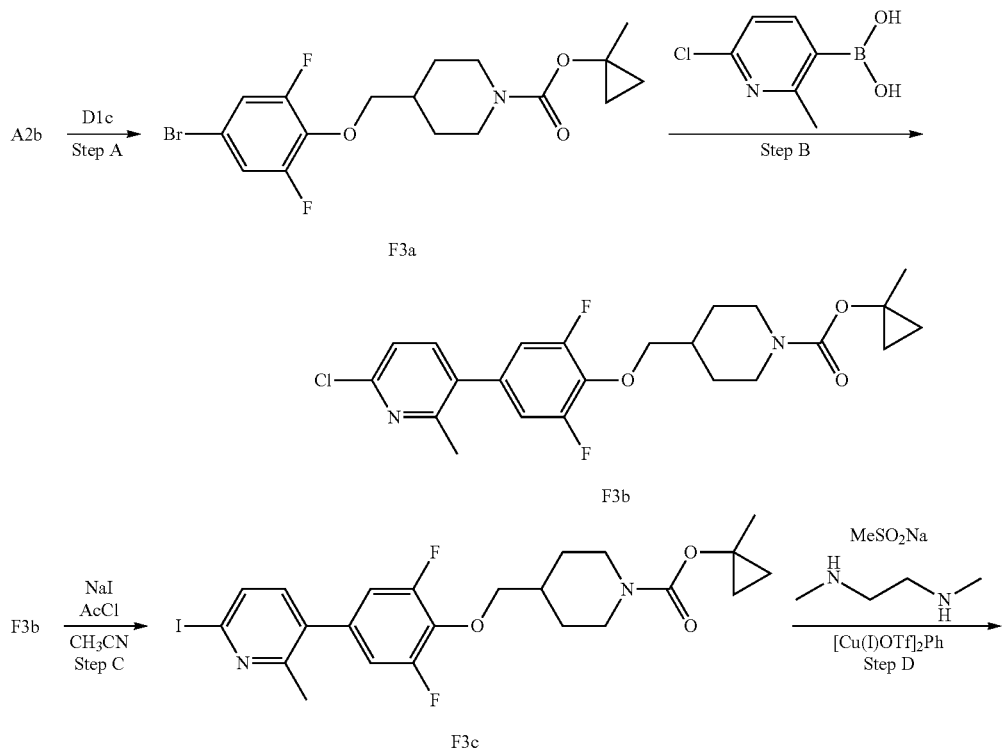

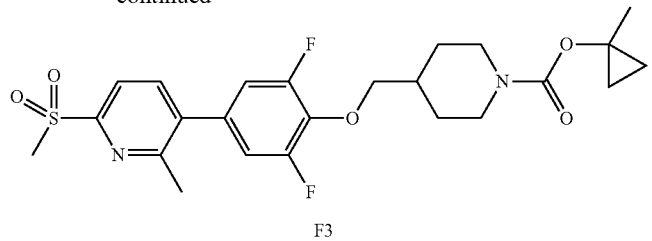

F3

Step A: A solution of Intermediate A2b in CH$_2$Cl$_2$ (100 ml) is cooled to 0° C., treated with TFA (10 ml) and stirred at rt for 2 h. The solvent is evaporated and coevaporated with toluene once. The crude is dissolved in CH$_2$Cl$_2$ (100 ml), treated with NEt$_3$ (10 ml, 72 mmol) and carbonate D1c (5.88 g, 24.8 mmol). The mixture is stirred at rt overnight, and then washed with 1M NaOH (3×), 1M HCl (1×) and brine (1×). The organic phase is dried (Na$_2$SO$_4$) and concentrated in vacuo to afford 1-methylcyclopropyl 4-((4-bromo-2,6-difluorophenoxy)methyl)piperidine-1-carboxylate F3a as a light orange oil. MS calcd. for [M+H]$^+$ C$_{17}$H$_{21}$BrF$_2$NO$_3$: 404.1. found: 404.0. The product is used without purification.

Step B: In a microwave vial a mixture of Intermediate F3a (815 mg, 2.0 mmol), 6-chloro-2-methylpyridin-3-ylboronic acid (375 mg, 2.2 mmol) and Pd(dppf)Cl$_2$ (105 mg, 0.14 mmol) in dry dioxane (16 ml) is treated with 1M Cs$_2$CO$_3$ (2.4 ml, 2.4 mmol). The vial is sealed and is subjected to microwave irradiation (120° C., 20 min) under nitrogen atmosphere. After cooling, the mixture is diluted with EtOAc, washed with brine, dried (Na$_2$SO$_4$) and concentrated in vacuo. Purification by flash chromatography (EtOAc/hexanes gradient) affords 1-methylcyclopropyl 4-((4-(6-chloro-2-methylpyridin-3-yl)-2,6-difluorophenoxy)methyl)piperidine-1-carboxylate F3b as a white solid: $^1$H-NMR (400 MHz, CDCl$_3$) δ=7.46 (d, J=8.0 Hz, 1H), 7.24 (d, J=8.0 Hz, 1H), 6.87 (d, J=8.8 Hz, 2H), 4.30-4.05 (br. d, 2H), 4.04 (d, J=6.8 Hz, 2H), 2.79 (t, J=12.0 Hz, 2H), 2.51 (s, 3H), 2.00 (m, 1H), 1.89 (dd, J=12.8, 1.2 Hz, 2H), 1.57 (s, 3H), 1.38-1.25 (m, 2H), 0.91-0.87 (m, 2H), 0.66-0.63 (m, 2H); $^{19}$F-NMR (376.5 MHz, CDCl$_3$) δ=−127.27; MS calcd. for [M+H]$^+$ C$_{23}$H$_{26}$ClF$_2$N$_2$O$_3$: 451.1. found: 451.2.

Step C: In a 20 mL vial, Intermediate F3b (451 mg, 1.0 mmol) and sodium iodide (902 mg, 6.0 mmol) are suspended in dry MeCN (5 mL). Acetyl chloride (213 uL, 3.0 mmol) is added, the vial is sealed, and the mixture is heated to 80° C. for 16 h, then allowed to cool to rt. The suspension is diluted with an aqueous solution of 10% K$_2$CO$_3$ and 5% NaHSO$_3$ and extracted twice with CH$_2$Cl$_2$. The organics are dried (MgSO$_4$) and concentrated in vacuo to afford 1-methylcyclopropyl 4-((2,6-difluoro-4-(6-iodo-2-methylpyridin-3-yl)phenoxy)methyl)piperidine-1-carboxylate F3c, which is used without further purification: $^1$H-NMR (400 MHz, CDCl$_3$) δ=7.63 (d, J=8.0 Hz, 1H), 7.12 (d, J=8.0 Hz, 1H), 6.86 (d, J=8.8 Hz, 2H), 4.30-4.05 (br. d, 2H), 4.04 (d, J=6.8 Hz, 2H), 2.79 (t, J=12.0 Hz, 2H), 2.50 (s, 3H), 2.00 (m, 1H), 1.89 (d, J=12.8 Hz, 2H), 1.57 (s, 3H), 1.35-1.25 (m, 2H), 0.91-0.87 (m, 2H), 0.66-0.63 (m, 2H); $^{19}$F-NMR (376.5 MHz, CDCl$_3$) δ=−127.23; MS calcd. for [M+H]$^+$ C$_{23}$H$_{26}$F$_2$IN$_2$O$_3$: 543.1. found: 543.2.

Step D: The crude Intermediate F3c (198 mg, ca. 0.36 mmol), [Cu(I) OTf]$_2$Ph (13.1 mg, 0.026 mmol), and sodium methanesulfinate (62 mg, 0.61 mmol) are dissolved in dry DMSO (5 mL). Dimethyl ethylenediamine (7 μL, 0.064 mmol) is added and the solution is heated to 120° C. for 5 h. After cooling to rt, the mixture is diluted with H$_2$O (30 mL) and extracted twice with EtOAc. The organics are dried (MgSO$_4$), concentrated in vacuo, and purified by flash chromatography (EtOAc/hexanes gradient) to afford the title compound (Example F3) as a white solid: $^1$H-NMR (400 MHz, CDCl$_3$) δ=8.00 (d, J=8.0 Hz, 1H), 7.75 (d, J=8.0 Hz, 1H), 6.90 (d, J=8.8 Hz, 2H), 4.30-4.05 (br. d, 2H), 4.07 (d, J=6.8 Hz, 2H), 3.29 (s, 3H), 2.80 (t, J=12.0 Hz, 2H), 2.61 (s, 3H), 2.02 (m, 1H), 1.87 (d, J=12.8 Hz, 2H), 1.58 (s, 3H), 1.38-1.25 (m, 2H), 0.91-0.87 (m, 2H), 0.67-0.63 (m, 2H); $^{19}$F-NMR (376.5 MHz, CDCl$_3$) δ=−126.64; MS calcd. for [M+H]$^+$ C$_{24}$H$_{29}$F$_2$N$_2$O$_5$S: 495.2. found: 495.1.

Example F4

1-methylcyclopropyl 4-((2,6-difluoro-4-(2-methyl-6-(propylsulfonyl)pyridin-3-yl)phenoxy)methyl)piperidine-1-carboxylate

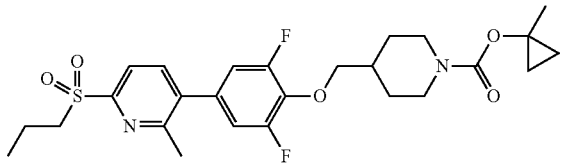

The Intermediate F3c (100 mg, ca. 0.18 mmol) is treated as described for Example F3, Step D, using sodium propane-1-sulfinate instead of sodium methanesulfinate to afford the title compound (Example F4) as a clear oil: $^1$H-NMR (400 MHz, CDCl$_3$) δ=7.97 (d, J=8.0 Hz, 1H), 7.71 (d, J=8.0 Hz, 1H), 6.92-6.85 (m, 2H), 4.30-4.15 (br. d, 2H), 4.04 (d, J=7.2 Hz, 2H), 3.42-3.39 (m, 2H), 2.81-2.75 (m, 2H), 2.59 (s, 3H), 2.02-1.97 (m, 1H), 1.89-1.79 (m, 4H), 1.55 (s, 3H), 1.37-1.25 (m, 2H), 1.07 (t, J=7.6 Hz, 3H), 0.88-0.85 (m, 2H), 0.64-0.61 (m, 2H); $^{19}$F-NMR (376.5 MHz, CDCl$_3$) δ=−126.69; MS calcd. for [M+H]$^+$ C$_{26}$H$_{33}$F$_2$N$_2$O$_5$S: 523.2. found: 523.2.

Example F5 sec-butyl 4-((2,6-difluoro-4-(2-methyl-6-(methylsulfonyl)pyridin-3-yl)phenoxy)methyl)piperidine-1-carboxylate

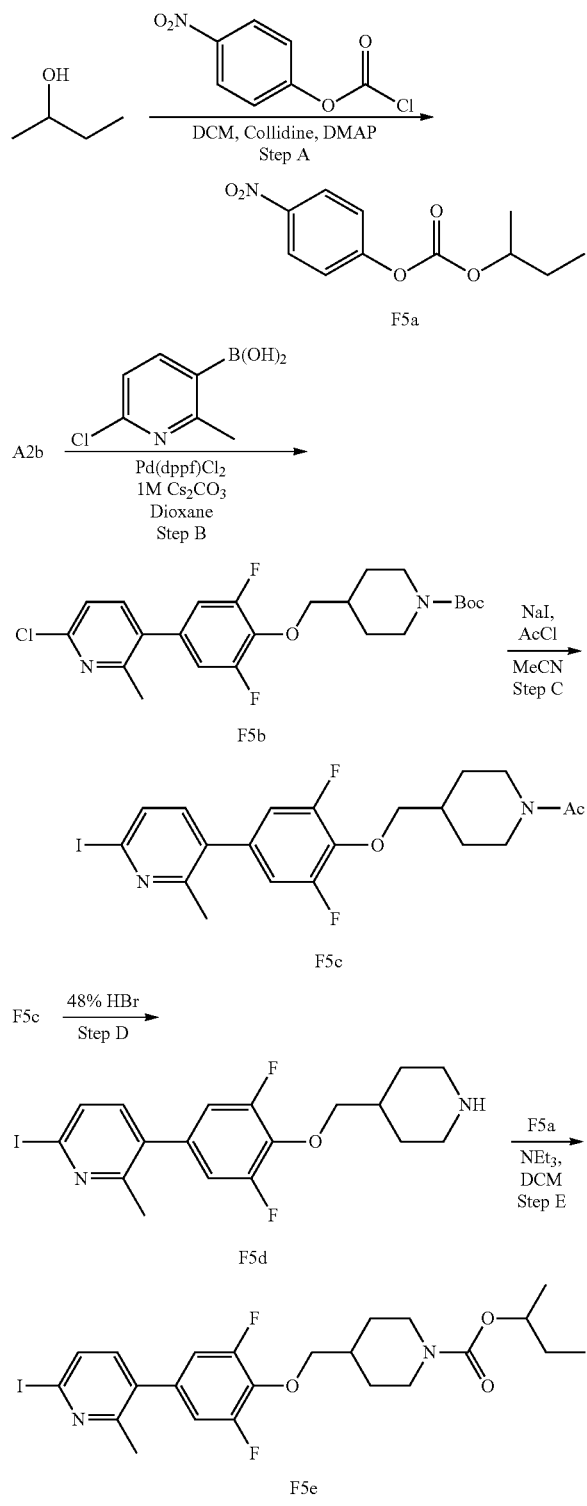

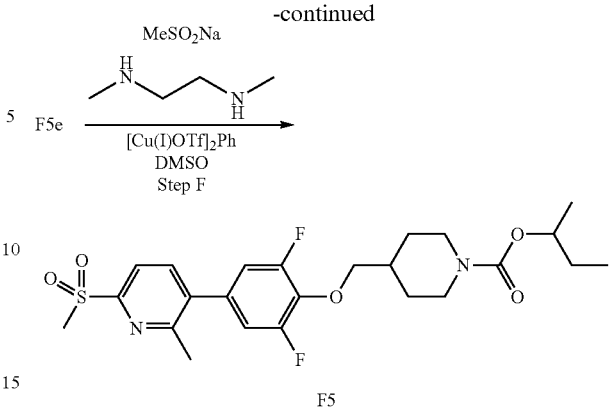

Step A: To a solution of isoamyl alcohol (1.0 g, 13.5 mmol) in CH$_2$Cl$_2$ (30 ml) is added 4-nitrophenyl carbonochloridate (3.2 g, 16.2 mmol), 2,4,6-collidine (2.14 ml, 16.2 mmol) and a catalytic amount of DMAP. After stirring for 2 h, 1N HCl is added and the aqueous layer is extracted with CH$_2$Cl$_2$, and the combined organic layers washed with 1N HCl, brine, and dried over Na$_2$SO$_4$. Evaporation of solvent and purification by flash chromatography (120 g SiO$_2$, EtOAc/hexanes gradient) yields sec-butyl 4-nitrophenyl carbonate F5a as a yellow oil. $^1$H-NMR (400 MHz, CDCl$_3$) δ=8.27 (d, J=9.2 Hz, 2H), 7.38 (d, J=9.2 Hz, 2H), 4.85 (sextet, J=6.4 Hz, 1H), 1.82-1.62 (m, 2H), 1.37 (d, J=6.4 Hz, 3H), 1.00 (t, J=7.2 Hz, 3H); MS calcd. for [M+Na]$^+$ C$_{11}$H$_{13}$NaNO$_5$: 262.1. found: 262.2.

Step B: In a microwave vial a mixture of Intermediate A2b (3.59 g, 8.85 mmol), 6-chloro-2-methylpyridin-3-ylboronic acid (1.67 g, 974 mmol), Pd(dppf)Cl$_2$ (505 mg, 0.619 mmol) in dry dioxane (30 mL) is treated with 1M Cs$_2$CO$_3$ (10.6 ml, 10.62 mmol). The vial is sealed and is subjected to microwave irradiation (120° C., 20 min) under nitrogen atmosphere. After cooling, the mixture is diluted with EtOAc, washed with brine, dried (Na$_2$SO$_4$) and concentrated in vacuo. Purification by flash chromatography (EtOAc/hexanes gradient) affords tert-butyl 4-((4-(6-chloro-2-methylpyridin-3-yl)-2,6-difluorophenoxy)methyl)piperidine-1-carboxylate F5b as a white solid: $^1$H-NMR (400 MHz, CDCl$_3$) δ=7.43 (d, J=8.0 Hz, 1H), 7.22 (d, J=8.0 Hz, 1H), 6.88-6.81 (m, 2H), 4.16 (br s, 2H), 4.02 (d, J=6.4 Hz, 2H), 2.78-2.73 (m, 2H), 2.48 (s, 3H), 2.01-1.95 (m, 1H), 1.87 (d, J=13.2 Hz, 2H), 1.47 (s, 9H), 1.34-1.24 (m, 2H); MS calcd. for [M+H]$^+$ C$_{23}$H$_{28}$ClF$_2$N$_2$O$_3$: 453.2. found: 453.2.

Step C: To a solution of Intermediate F5b (804 mg, 1.79 mmol) in MeCN (30 ml) are added NaI (1.6 g, 10.72 mmol) and acetyl chloride (381 µL, 5.37 mmol). After stirring at 80° C. for 16 h, the reaction is quenched with 10% aqueous K$_2$CO$_3$ and 10% aqueous NaHSO$_3$. The aqueous layer is extracted with CH$_2$Cl$_2$ and the organic layer washed with brine and dried over Na$_2$SO$_4$. Evaporation of solvent and purification by flash chromatography (EtOAc/hexanes gradient) yields 1-(4-((2,6-difluoro-4-(6-iodo-2-methylpyridin-3-yl)phenoxy)methyl)piperidin-1-yl)ethanone F5c as a yellow solid; MS calcd. for [M+H]$^+$ C$_{20}$H$_{22}$F$_2$IN$_2$O$_2$: 487.1. found: 487.2.

Step D: A solution of Intermediate F5c (450 mg, 0.926 mmol) in 48% aqueous HBr (20 ml) is refluxed for 5 h. The solution is cooled and the aqueous layer is extracted with EtOAc to remove any organic impurities. 6M NaOH is then added to basic pH, and the product is extracted with EtOAc. The combined organic layers are washed with brine and dried over Na$_2$SO$_4$. Evaporation of solvent yields 3-(3,5-difluoro- 4-(piperidin-4-ylmethoxy)phenyl)-6-iodo-2-methylpyridine F5d as a pale yellow oil that solidifies with time; $^1$H-NMR (400 MHz, CDCl$_3$) δ=7.61 (d, J=8.0 Hz, 1H), 7.09 (d, J=8.0 Hz, 1H), 6.86-6.80 (m, 2H), 4.02 (d, J=6.8 Hz, 2H), 3.17 (d, J=12.0 Hz, 2H), 2.72-2.65 (m, 2H), 2.48 (s, 3H), 2.00-1.88 (m, 5H), 1.38-128 (m, 2H); MS calcd. for [M+H]$^+$ C$_{18}$H$_{20}$F$_2$I N$_2$O: 445.1. found: 445.2.

Step E: To a solution of Intermediate F5d (50 mg, 0.113 mmol) in CH$_2$Cl$_2$ (2 ml) are added carbamate F5a (40 mg, 0.169) and NEt$_3$ (31 µL, 0.226). After stirring for 48 h the solvent is evaporated and the remaining residue is purified by flash chromatography (12 g SiO$_2$, EtOAc/hexanes gradient) to yield sec-butyl 4-((2,6-difluoro-4-(6-iodo-2-methylpyridin-3-yl)phenoxy)methyl)piperidine-1-carboxylate F5e as a clear oil: $^1$H-NMR (400 MHz, CDCl$_3$) δ=7.61 (d, J=8.0 Hz, 1H), 7.09 (d, J=8.0 Hz, 1H), 6.87-6.80 (m, 2H), 4.79-4.71 (m, 1H), 4.22 (br s, 2H), 4.02 (d, J=6.4 Hz, 2H), 2.83-2.77 (m, 2H), 2.48 (s, 3H), 2.04-1.94 (m, 1H), 1.87 (d, J=12.8 Hz, 2H), 1.64-1.50 (m, 2H), 1.30-1.23 (m, 2H), 1.21 (d, J=6.4 Hz, 3H), 0.911 (t, J=7.2 Hz, 3H); MS calcd. for [M+H]$^+$ C$_{23}$H$_{28}$F$_2$IN$_2$O$_3$: 545.1. found: 545.2.

Step F: Intermediate F5e (24 mg, ca. 0.044 mmol), [Cu(I) OTf]$_2$Ph (2.0 mg, 0.0031 mmol) and sodium methanesulfinate (9 mg, 0.88 mmol) are dissolved in dry DMSO (2 mL). Dimethyl ethylenediamine (1 µL, 0.017 mmol) is added and the solution is heated to 120° C. for 2 h. After cooling to 23° C., the mixture is diluted with water and extracted twice with EtOAc. The organics are washed with brine and dried over Na$_2$SO$_4$, concentrated in vacuo, and purified by flash chromatography (EtOAc/hexanes gradient) to afford the title compound (Example F5) as a clear oil: $^1$H-NMR (400 MHz, CDCl$_3$) δ=7.97 (d, J=8.0 Hz, 1H), 7.72 (d, J=8.0 Hz, 1H), 6.92-6.87 (m, 2H), 4.79-4.71 (m, 1H), 4.22 (br s, 2H), 4.05 (d, J=6.4 Hz, 2H), 3.27 (s, 3H), 2.83-2.77 (m, 2H), 2.59 (s, 3H), 2.04-1.98 (m, 1H), 1.87 (d, J=12.8 Hz, 2H), 1.65-1.50 (m, 2H), 1.38-1.23 (m, 2H), 1.22 (d, J=6.4 Hz, 3H), 0.911 (t, J=7.2 Hz, 3H); $^{19}$F-NMR (376.5 MHz, CDCl$_3$) δ=−126.63; MS calcd. for [M+H]$^+$ C$_{24}$H$_{31}$F$_2$N$_2$O$_5$S: 497.2. found: 497.2.

Example F6 sec-butyl 4-((2,6-difluoro-4-(2-methyl-6-(propylsulfonyl)pyridin-3-yl)phenoxy)methyl)piperidine-1-carboxylate

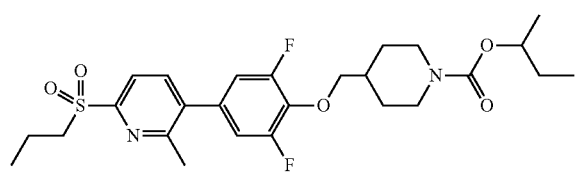

The Intermediate F5e (40 mg, ca. 0.05 mmol) is treated as described for Example F5, Step F, using sodium propane-1-sulfinate instead of sodium methanesulfinate to afford the title compound (Example F6) as a clear oil: $^1$H-NMR (400 MHz, CDCl$_3$) δ=7.96 (d, J=8.0 Hz, 1H), 7.71 (d, J=8.0 Hz, 1H), 6.92-6.87 (m, 2H), 4.79-4.71 (m, 1H), 4.22 (br s, 2H), 4.04 (d, J=6.4 Hz, 2H), 3.42-3.38 (m, 2H), 2.83-2.77 (m, 2H), 2.58 (s, 3H), 2.04-1.98 (m, 1H), 1.90-1.80 (m, 4H), 1.64-1.52 (m, 2H), 1.35-1.25 (m, 2H), 1.22 (d, J=6.4 Hz, 3H), 1.06 (t, J=7.6 Hz, 3H), 0.911 (t, J=7.2 Hz, 3H); $^{19}$F-NMR (376.5 MHz, CDCl$_3$) δ=−126.68; MS calcd. for [M+H]$^+$ C$_{26}$H$_{35}$F$_2$N$_2$O$_5$S: 525.2. found: 525.2.

Example F7

1-methylcyclopropyl 4-((2,6-difluoro-4-(2-methyl-6-(1H-1,2,4-triazol-1-yl)pyridin-3-yl)phenoxy)methyl)piperidine-1-carboxylate

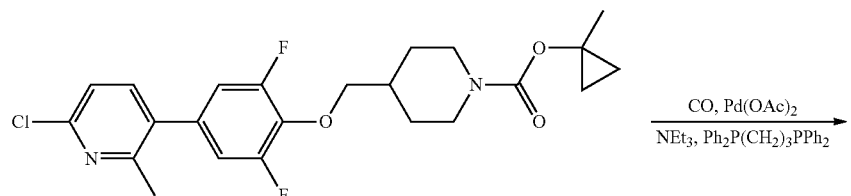

The Intermediate F3c (198 mg, ca. 0.36 mmol) is treated as described for Example F1, Step B to afford the title compound (Example F7): $^1$H-NMR (400 MHz, CDCl$_3$) δ=9.20 (s, 1H), 8.10 (s, 1H), 7.77 (d, J=8.4 Hz, 1H), 7.66 (d, J=8.4 Hz, 1H), 6.89 (d, J=8.8 Hz, 2H), 4.30-4.00 (br. d, 2H), 4.03 (d, J=6.0 Hz, 2H), 2.77 (t, J=12.4 Hz, 2H), 2.53 (s, 3H), 2.04-1.94 (m, 1H), 1.90-1.84 (m, 2H), 1.55 (s, 3H), 1.35-1.24 (m, 2H), 0.88-0.85 (m, 2H), 0.64-0.60 (m, 2H); $^{19}$F-NMR (376.5 MHz, CDCl$_3$) δ=−127.30; MS calcd. for [M+H]$^+$ C$_{25}$H$_{28}$F$_2$N$_5$O$_3$: 484.2. found: 484.2.

Example F8 methyl 5-(3,5-difluoro-4-((1-((1-methylcyclopropoxy)carbonyl)piperidin-4-yl)methoxy)phenyl)-6-methylpicolinate -continued

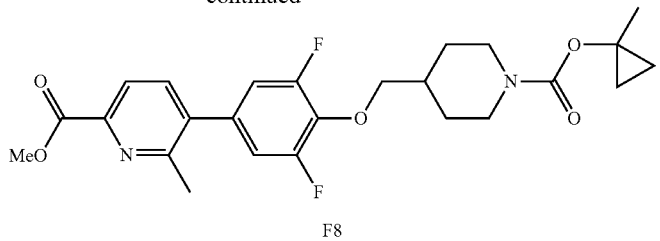

F8

A solution of Intermediate F3b (274 mg, 0.61 mmol), Pd(OAc)$_2$ (30 mg, 0.13 mmol) and Ph$_2$P(CH$_2$)$_3$PPh$_2$ (55 mg, 0.13 mmol) in DMA/MeOH (1:1, 10 mL) is degassed with argon. CO is then bubbled through the solution for 15 min, the flask sealed and heated to 80° C. overnight. The mixture is then filtered through Celite, washed with MeOH and concentrated in vacuo. The crude is purified by flash chromatography (EtOAc/hexanes gradient) to afford the title compound (Example F8) as a white solid: $^1$H-NMR (400 MHz, CDCl$_3$) δ=8.05 (d, J=8.0 Hz, 1H), 7.65 (d, J=8.0 Hz, 1H), 6.92 (d, J=8.8 Hz, 2H), 4.36-4.05 (m, 4H), 4.05 (s, 3H), 2.80 (t, J=12.8 Hz, 2H), 2.63 (s, 3H), 2.10-1.95 (m, 1H), 1.92-1.85 (m, 2H), 1.58 (s, 3H), 1.40-1.27 (m, 2H), 0.91-0.88 (m, 2H), 0.67-0.63 (m, 2H); $^{19}$F-NMR (376.5 MHz, CDCl$_3$) δ=−127.14; MS calcd. for [M+H]$^+$ C$_{25}$H$_{29}$F$_2$N$_2$O$_5$: 475.2. found: 475.2.

Example G1

5-(4'-((1-(5-ethylpyrimidin-2-yl)piperidin-4-yl)methoxy)-3',5'-difluorobiphenyl-4-yl)oxazole

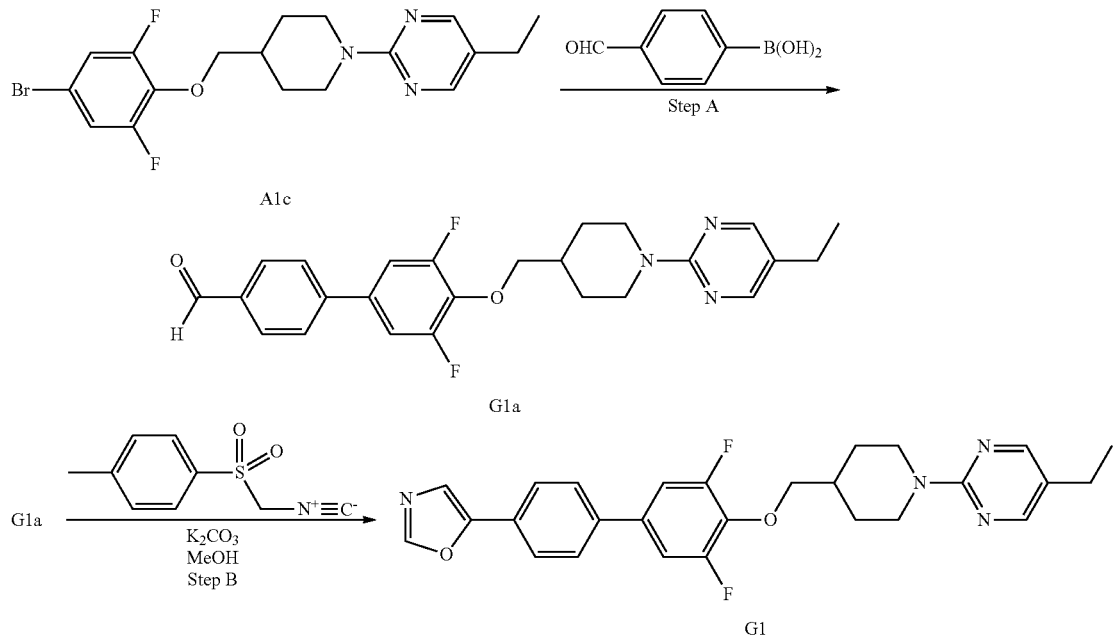

Step A: Intermediate A1c (412 mg, 1.0 mmol) is reacted with 4-formylphenylboronic acid (165 mg, 1.1 mmol) according to the same procedure described for the preparation of Example A3 to afford 4'-((1-(5-ethylpyrimidin-2-yl)piperidin-4-yl)methoxy)-3',5'-difluorobiphenyl-4-carbaldehyde G1a as an off-white powder: $^1$H-NMR (400 MHz, CDCl$_3$) δ=10.06 (s, 1H), 8.17 (s, 2H), 7.95 (d, J=8.4 Hz, 2H), 7.67 (d, J=8.4 Hz, 2H), 7.19 (d, J=9.2 Hz, 2H), 4.77 (d, J=13.2 Hz, 2H), 4.06 (d, J=6.4 Hz, 2H), 2.92 (td, J=12.8, 2.8 Hz, 2H), 2.45 (q, J=7.6 Hz, 2H), 2.12 (m, 1H), 1.97 (d, J=13.2 Hz, 2H), 1.36 (qd, J=12.8, 4.4 Hz, 2H), 1.19 (t, J=7.6 Hz, 3H); $^{19}$F-NMR (376.5 MHz, CDCl$_3$) δ=−127.00; MS calcd. for [M+H]$^+$ C$_{25}$H$_{26}$F$_2$N$_3$O$_2$: 438.2. found: 438.2.

Step B: In a pressure vial, Intermediate G1a (55 mg, 0.13 mmol), p-toluenesulfonylmethyl isocyanide (25 mg, 0.13 mmol), and potassium carbonate (50 mg, 0.36 mmol) are suspended in dry methanol (1.5 mL). The vial is sealed and the suspension heated to 80° C. for 16 h, then cooled to rt, and concentrated in vacuo. The residue is taken up in H$_2$O (50 mL) and extracted three times with CH$_2$Cl$_2$. The combined organics are dried (MgSO$_4$), concentrated, and purified by flash chromatography (EtOAc/hexanes gradient) to afford the title compound (Example G1) as an off-white solid: $^1$H-NMR (400 MHz, CDCl$_3$) δ=8.17 (s, 2H), 7.95 (s, 1H), 7.73 (d, J=8.4 Hz, 2H), 7.58 (d, J=8.4 Hz, 2H), 7.41 (s, 1H), 7.16 (d, J=9.6 Hz, 2H), 4.77 (d, J=13.2 Hz, 2H), 4.04 (d, J=6.4 Hz, 2H), 2.93 (td, J=12.8, 2.8 Hz, 2H), 2.46 (q, J=7.6 Hz, 2H), 2.11 (m, 1H), 1.97 (d, J=13.2 Hz, 2H), 1.36 (qd, J=12.8, 4.4 Hz, 2H), 1.19 (t, J=7.6 Hz, 3H); $^{19}$F-NMR (376.5 MHz, CDCl$_3$) δ=−127.46; MS calcd. for [M+H]$^+$C$_{27}$H$_{27}$F$_2$N$_4$O$_2$: 477.2. found: 477.2.

Example G2

2-(4-(((3,5-difluoro-4'-(1H-pyrazol-3-yl)biphenyl-4-yloxy)methyl)piperidin-1-yl)-5-ethylpyrimidine

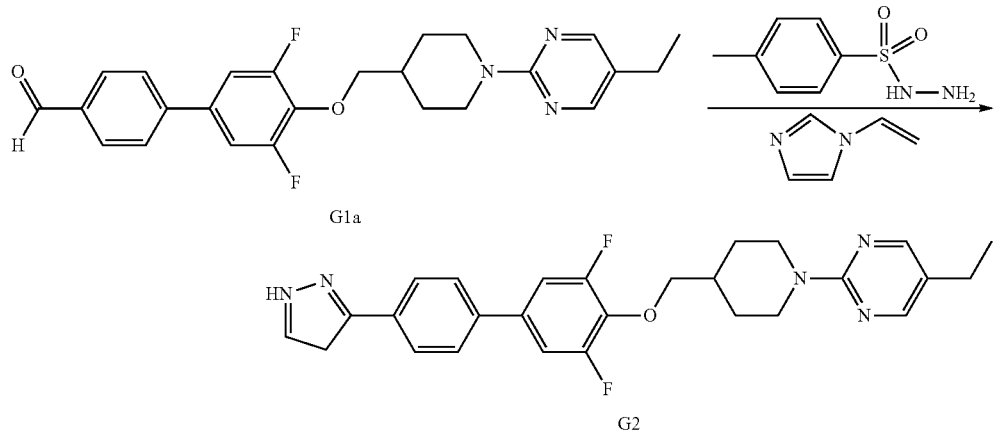

Intermediate G1a (55 mg, 0.13 mmol) and tosylhydrazine (25 mg, 0.13 mmol) are dissolved in dry acetonitrile (1 mL) and stirred at rt for 3 h. 5 N NaOH (30 μL, 0.15 mmol) is added and the mixture stirred for an additional 30 min at rt. Vinylimidazole (60 μL, 0.66 mmol) is added and the mixture us heated to 50° C. for 16 h, then cooled to rt and concentrated in vacuo. The residue us taken up in $CH_2Cl_2$ and purified by flash chromatography ($CH_2Cl_2$/MeOH gradient) to afford the title compound (Example G2) as a white solid: $^1$H-NMR (400 MHz, $CDCl_3$) δ=10.3 (br s, 1H), 8.18 (s, 2H), 7.84 (d, J=8.4 Hz, 2H), 7.65 (d, J=2.4 Hz, 1H), 7.57 (d, J=8.4 Hz, 2H), 7.17 (d, J=9.2 Hz, 2H), 6.67 (d, J=2.4 Hz, 1H), 4.77 (d, J=13.2 Hz, 2H), 4.03 (d, J=6.4 Hz, 2H), 2.93 (td, J=12.8, 2.4 Hz, 2H), 2.46 (q, J=7.6 Hz, 2H), 2.11 (m, 1H), 1.97 (d, J=13.2 Hz, 2H), 1.36 (qd, J=12.8, 4.0 Hz, 2H), 1.19 (t, J=7.6 Hz, 3H); $^{19}$F-NMR (376.5 MHz, $CDCl_3$) δ=−127.74; MS calcd. for $[M+H]^+$ $C_{27}H_{28}F_2N_5O$: 476.2. found: 476.2.

Example H1

1-(4'-((1-(5-ethylpyrimidin-2-yl)piperidin-4-yl)methoxy)-3',5'-difluorobiphenyl-4-yl)-N-methylmethanamine

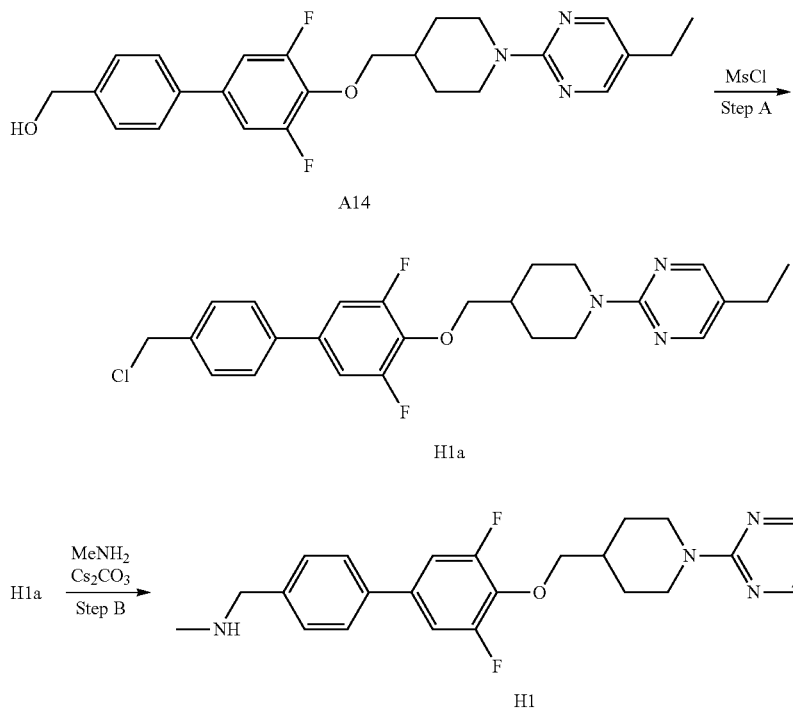

Step A: Example A14 (153 mg, 0.35 mmol) is dissolved in dry CH$_2$Cl$_2$ (15 mL) and treated with NEt$_3$ (0.5 mL) and methanesulfonyl chloride (0.2 mL, 2.5 mmol). The mixture is stirred at rt overnight. The mixture is washed with H$_2$O (40 mL) and brine (10 mL), dried (MgSO$_4$), and concentrated in vacuo to afford crude 2-(4-((4'-(chloromethyl)-3,5-difluoro-biphenyl-4-yloxy)methyl)piperidin-1-yl)-5-ethylpyrimidine H1a as an off-white solid, which is used in the next step without further purification: $^1$H-NMR (400 MHz, CDCl$_3$) δ=8.17 (s, 2H), 7.50 (d, J=8.4 Hz, 2H), 7.46 (d, J=8.4 Hz, 2H), 7.12 (d, J=9.6 Hz, 2H), 4.77 (d, J=13.2 Hz, 2H), 4.62 (s, 2H), 4.03 (d, J=6.4 Hz, 2H), 2.93 (td, J=12.8, 2.4 Hz, 2H), 2.46 (q, J=7.6 Hz, 2H), 2.11 (m, 1H), 1.97 (d, J=13.2 Hz, 2H), 1.35 (qd, J=12.8, 4.0 Hz, 2H), 1.19 (t, J=7.6 Hz, 3H); $^{19}$F-NMR (376.5 MHz, CDCl$_3$) δ=−127.60; MS calcd. for [M+H]$^+$ C$_{25}$H$_{27}$ClF$_2$N$_3$O: 458.2. found: 458.2.

Step B: In a pressure vial, Intermediate H1a (20 mg, 0.04 mmol), methylamine hydrochloride (6 mg, 0.08 mmol) and cesium carbonate (100 mg, 0.3 mmol) are suspended in dry CH$_3$CN (3 mL). The vial is sealed and the mixture heated to 80° C. for 5 h, cooled to rt, and filtered. The residue is taken up in CH$_2$Cl$_2$, filtered through a 0.2 μm syringe filter, and purified by flash chromatography (CH$_2$Cl$_2$/MeOH gradient) to afford the title compound (Example H1) as a white solid: $^1$H-NMR (400 MHz, CDCl$_3$) δ=8.17 (s, 2H), 7.47 (d, J=8.4 Hz, 2H), 7.40 (d, J=8.4 Hz, 2H), 7.11 (d, J=9.6 Hz, 2H), 4.77 (d, J=13.2 Hz, 2H), 4.02 (d, J=6.4 Hz, 2H), 3.81 (s, 2H), 2.92 (td, J=12.8, 2.4 Hz, 2H), 2.48 (s, 3H), 2.45 (q, J=7.6 Hz, 2H), 2.10 (m, 1H), 1.97 (d, J=13.2 Hz, 2H), 1.35 (qd, J=12.8, 4.0 Hz, 2H), 1.18 (t, J=7.6 Hz, 3H); $^{19}$F-NMR (376.5 MHz, CDCl$_3$) δ=−127.86; MS calcd. for [M+H]$^+$ C$_{26}$H$_{31}$F$_2$N$_4$O: 453.2. found: 453.3.

By repeating the procedure described in the above Example H1, using appropriate starting materials, the following compounds of Formula I, as identified in Table 4, are obtained:

| Example # | Structure | NMR and/or ESMS |
|---|---|---|
| H2 | | $^1$H-NMR (400 MHz, CDCl$_3$) δ = 8.17 (s, 2H), 7.45 (d, J = 8.4 Hz, 2H), 7.41 (d, J = 8.4 Hz, 2H), 7.10 (d, J = 9.6 Hz, 2H), 4.76 (d, J = 13.2 Hz, 2H), 4.02 (d, J = 6.4 Hz, 2H), 3.76 (s, 2H), 2.92 (td, J = 12.8, 2.4 Hz, 2H), 2.46 (q, J = 7.6 Hz, 2H), 2.10 (m, 1H), 1.97 (d, J = 13.2 Hz, 2H), 1.35 (qd, J = 12.8, 4.0 Hz, 2H), 1.19 (s, 9H), 1.18 (t, J = 7.6 Hz, 3H); $^{19}$F-NMR (376.5 MHz, CDCl$_3$) δ = −127.95; MS calcd. for [M + H]$^+$ C$_{29}$H$_{37}$F$_2$N$_4$O: 495.3, found: 495.4. |
| H3 | 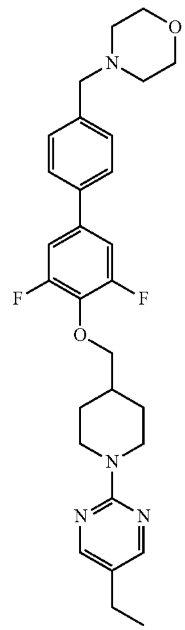 | $^1$H-NMR (400 MHz, CDCl$_3$) δ = 8.17 (s, 2H), 7.46 (d, J = 8.0 Hz, 2H), 7.39 (d, J = 8.0 Hz, 2H), 7.11 (d, J = 9.6 Hz, 2H), 4.77 (d, J = 13.2 Hz, 2H), 4.02 (d, J = 6.4 Hz, 2H), 3.72 (dd, J = 5.6, 4.4 Hz, 4H), 5.53 (s, 2H), 2.92 (td, J = 12.8, 2.4 Hz, 2H), 2.46 (m, 6H), 2.11 (m, 1H), 1.97 (d, J = 13.2 Hz, 2H), 1.35 (qd, J = 12.8, 4.0 Hz, 2H), 1.18 (t, J = 7.6 Hz, 3H); $^{19}$F-NMR (376.5 MHz, CDCl$_3$) δ = −127.87; MS calcd. for [M + H]$^+$ C$_{29}$H$_{35}$F$_2$N$_4$O$_2$: 509.3, found: 509.3. |
| H4 | 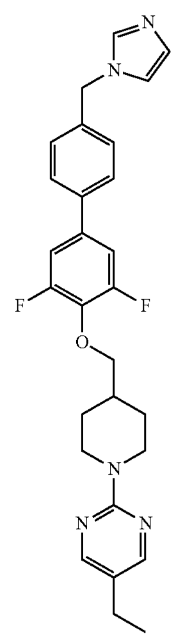 | $^1$H-NMR (400 MHz, CDCl$_3$) δ = 8.17 (s, 2H), 7.57 (s, 1H), 7.48 (d, J = 8.4 Hz, 2H), 7.21 (d, J = 8.4 Hz, 2H), 7.11 (s, 1H), 7.09 (d, J = 9.6 Hz, 2H), 6.92 (s, 1H), 5.16 (s, 2H), 4.76 (d, J = 13.2 Hz, 2H), 4.02 (d, J = 6.4 Hz, 2H), 2.92 (td, J = 12.8, 2.8 Hz, 2H), 2.45 (q, J = 7.6 Hz, 2H), 2.10 (m, 1H), 1.96 (d, J = 13.2 Hz, 2H), 1.35 (qd, J = 12.8, 4.0 Hz, 2H), 1.18 (t, J = 7.6 Hz, 3H); $^{19}$F-NMR (376.5 MHz, CDCl$_3$) δ = −127.50; MS calcd. for [M + H]$^+$ C$_{28}$H$_{30}$F$_2$N$_5$O: 490.2, found: 490.3. |

-continued

| Example # | Structure | NMR and/or ESMS |
|---|---|---|
| H5 | 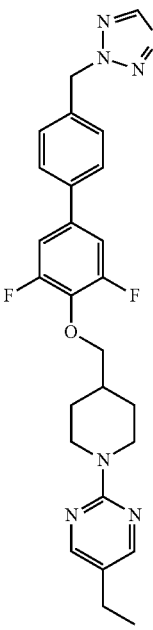 | ¹H-NMR (400 MHz, CDCl₃) δ = 8.53 (s, 1H), 8.17 (s, 2H), 7.51 (d, J = 8.4 Hz, 2H), 7.44 (d, J = 8.4 Hz, 2H), 7.09 (d, J = 9.2 Hz, 2H), 5.84 (s, 2H), 4.76 (d, J = 13.2 Hz, 2H), 4.02 (d, J = 6.4 Hz, 2H), 2.92 (td, J = 12.8, 2.4 Hz, 2H), 2.45 (q, J = 7.6 Hz, 2H), 2.10 (m, 1H), 1.96 (d, J = 13.2 Hz, 2H), 1.35 (qd, J = 12.8, 4.4 Hz, 2H), 1.18 (t, J = 7.6 Hz, 3H); ¹⁹F-NMR (376.5 MHz, CDCl₃) δ = −127.43; MS calcd. for [M + H]⁺ $C_{26}H_{28}F_2N_7O$: 492.2, found: 492.3. |
| H6 | 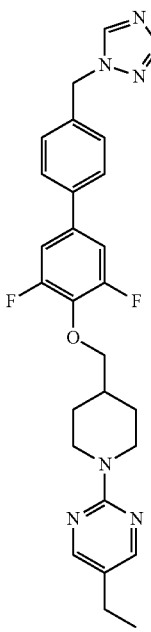 | ¹H-NMR (400 MHz, CDCl₃) δ = 8.55 (s, 1H), 8.17 (s, 2H), 7.54 (d, J = 8.4 Hz, 2H), 7.37 (d, J = 8.4 Hz, 2H), 7.10 (d, J = 9.2 Hz, 2H), 5.63 (s, 2H), 4.77 (d, J = 13.2 Hz, 2H), 4.03 (d, J = 6.4 Hz, 2H), 2.92 (td, J = 12.8, 2.4 Hz, 2H), 2.46 (q, J = 7.6 Hz, 2H), 2.10 (m, 1H), 1.96 (d, J = 13.2 Hz, 2H), 1.35 (qd, J = 12.8, 4.0 Hz, 2H), 1.18 (t, J = 7.6 Hz, 3H); ¹⁹F-NMR (376.5 MHz, CDCl₃) δ = −127.24; MS calcd. for [M + H]⁺ $C_{26}H_{28}F_2N_7O$: 492.2, found: 492.3. |

Example I1

5-(4-((1-(5-ethylpyrimidin-2-yl)piperidin-4-yl)methoxy)-3,5-difluorophenyl)picolinamide

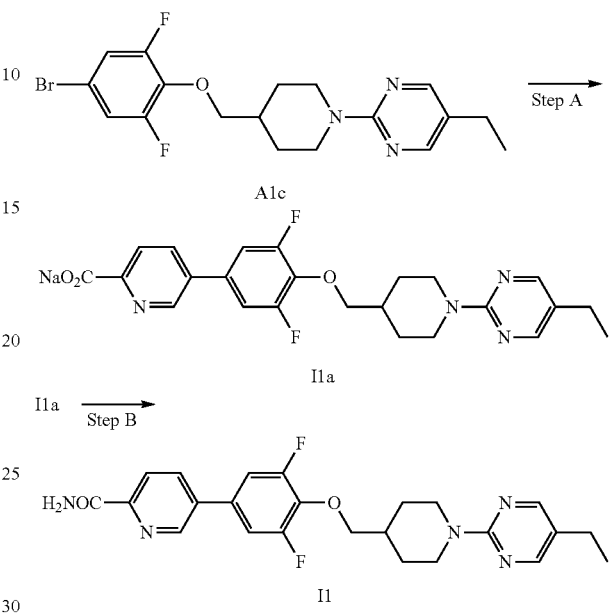

Step A: A Smith-Process vial is charged with Intermediate A1c (206 mg, 0.5 mmol), methyl 5-(4,4,5,5-tetramethyl-1,3,2-dioxaborolan-2-yl)picolinate (158 mg, 0.6 mmol), dichloro[1,1′-bis(diphenylphosphino)ferrocene]palladium(II) (18 mg, 5 mol %), and dry dioxane (2.5 mL). To the solution is added 1M aqueous $Cs_2CO_3$ (1.7 mL, 1.7 mmol), and the biphasic mixture is subjected to microwave irradiation (130° C., 30 min). Brine (30 mL) is added, the precipitate is filtered, washed with $H_2O$ (2×1 mL), $Et_2O$ (3×10 mL) and dried in vacuo to afford 5-(4-((1-(5-ethylpyrimidin-2-yl)piperidin-4-yl)methoxy)-3,5-difluorophenyl)picolinic acid sodium salt I1a as a brown solid. The crude compound is used in the next step without further purification: MS calcd. for [M+F1]⁺ $C_{24}H_{25}F_2N_4O_3$: 455.2. found: 455.2.

Step B: A solution of Intermediate I1a (71 mg, 0.12 mmol) in THF (10 mL) is cooled to 0° C. Oxalyl chloride (0.30 mL, 3.4 mmol) is added followed by 1 drop of DMF (25 μL). The resulting solution is stirred at rt for 1.5 h, then co-evaporated with THF (2×10 mL). The residue is dissolved in THF (3 mL) and treated with aqueous ammonium hydroxide solution (28%, 1.5 mL). The reaction mixture is stirred at rt 1 h. $H_2O$ (20 mL) is added and the product is extracted with EtOAc (3×10 mL). The organic layer is washed with $H_2O$ (10 mL), dried ($Na_2SO_4$) and concentrated in vacuo. Purification by flash chromatography (EtOAc/hexanes gradient) affords Example I1 as an off-white solid: ¹H-NMR (400 MHz, DMSO-d6) δ=8.97 (dd, J=2.4, 0.8 Hz, 1H), 8.31 (dd, J=8.4, 2.4 Hz, 1H), 8.23 (s, 2H), 8.16 (bs, 1H), 8.08 (dd, J=8.4, 0.8 Hz, 1H), 7.72 (m, 3H), 4.66 (m, 2H), 4.06 (d, J=6.4 Hz, 2H), 2.88 (m, 2H), 2.42 (q, J=7.6 Hz, 2H), 2.04 (m, 1H), 1.84 (m, 2H), 1.23 (m, 2H), 1.12 (t, J=7.6 Hz, 3H); MS calcd. for [M+H]⁺ $C_{24}H_{26}F_2N_5O_2$: 454.2. found: 454.2.

By repeating the procedure described in the above Example I1, using appropriate starting materials, the following compounds of Formula I, as identified in Table 5, are obtained:

TABLE 5

| Example # | Structure | NMR and/or ESMS |
|---|---|---|
| I2 | 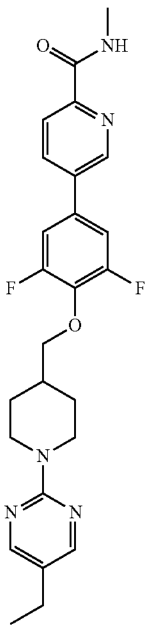 | ¹H-NMR (400 MHz, DMSO-d6) δ = 8.97 (dd, J = 2.4, 0.8 Hz, 1H), 8.82 (q, J = 4.8 Hz, 1H), 8.31 (dd, J = 8.4, 2.4 Hz, 1H), 8.23 (s, 2H), 8.07 (dd, J = 8.4, 0.8 Hz, 1H), 7.73 (m, 2H), 4.66 (m, 2H), 4.05 (d, J = 6.4 Hz, 2H), 2.88 (m, 2H), 2.83 (d, J = 4.8 Hz, 3H), 2.42 (q, J = 7.6 Hz, 2H), 2.04 (m, 1H), 1.83 (m, 2H), 1.24 (m, 2H), 1.12 (t, J = 7.6 Hz, 3H); MS calcd. for [M + H]⁺ $C_{25}H_{28}F_2N_5O_2$: 468.2, found: 468.2. |
| I3 | | ¹H-NMR (400 MHz, DMSO-d6) δ = 8.94 (dd, J = 2.4, 0.8 Hz, 1H), 8.24 (m, 3H), 7.69 (m, 2H), 7.63 (dd, J = 8.4, 0.8 Hz, 1H), 4.66 (m, 2H), 4.05 (d, J = 6.4 Hz, 2H), 3.02 (s, 3H), 2.98 (s, 3H), 2.88 (m, 2H), 2.42 (q, J = 7.6 Hz, 2H), 2.04 (m, 1H), 1.84 (m, 2H), 1.24 (m, 2H), 1.12 (t, J = 7.6 Hz, 3H); MS calcd. for [M + H]⁺ $C_{26}H_{30}F_2N_5O_2$: 482.2, found: 482.2. |

Example J1

1-methylcyclopropyl 4-((2,6-difluoro-4-(2-(piperazine-1-carbonyl)pyrimidin-5-yl)phenoxy)methyl)piperidine-1-carboxylate

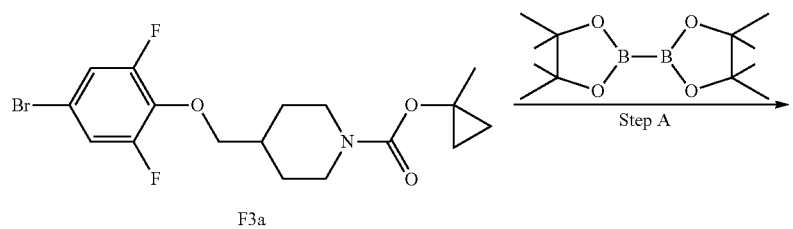

F3a → Step A

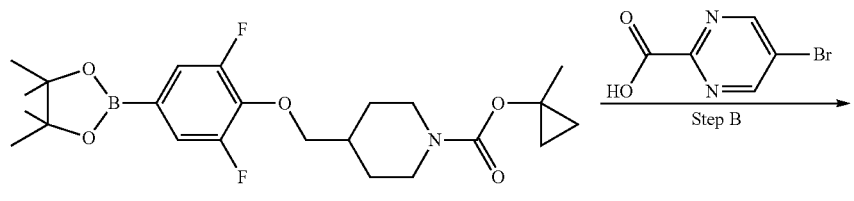

J1a → Step B

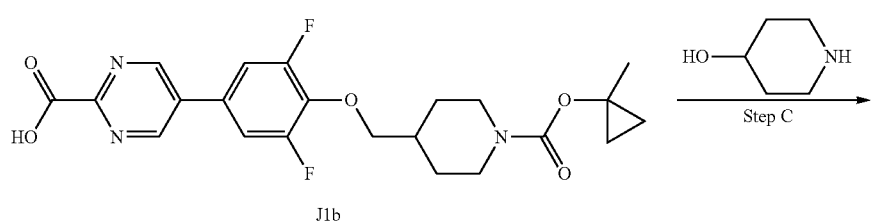

J1b → Step C

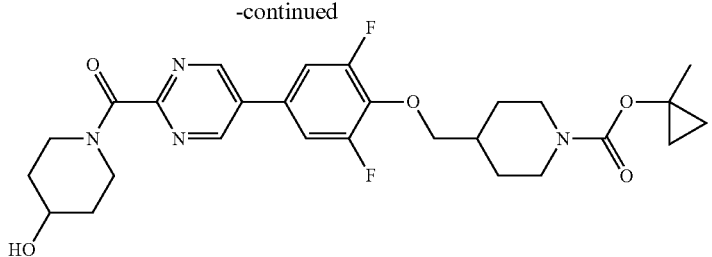

J1

Step A: Boronic ester J1a is obtained from Intermediate F3a using procedure described in Step D, Example A1 as a white solid: $^1$H-NMR (400 MHz, CDCl$_3$) δ=7.27 (m, 2H), 4.01 (d, J=6.4 Hz, 2H), 3.91 (m, 2H), 2.73 (m, 2H), 1.88 (m, 1H), 1.46 (s, 3H), 1.28 (s, 12H), 1.14 (m, 2H), 0.75 (m, 2H), 0.59 (m, 2H); MS calcd. for [M+H]$^+$ C$_{23}$H$_{33}$BF$_2$NO$_5$: 452.2. found: 452.3.

Step B: A vial is charged with Intermediate J1a (677 mg, 1.5 mmol), 5-bromopyrimidine-2-carboxylic acid (335 mg, 1.1 mmol), dichloro[1,1'-bis(diphenylphosphino)ferrocene]palladium(II) (110 mg, 0.15 mmol), dioxane (3.4 mL) and DMF (3.4 mL). To the solution is added 1M aqueous Cs$_2$CO$_3$ (4.95 mL, 4.95 mmol), and the biphasic mixture is subjected to microwave irradiation (120° C., 30 min). The mixture is diluted with H$_2$O (100 mL) and extracted with EtOAc (2×50 mL). The aqueous phase is acidified with 1 N HCl (11 mL), and extracted with EtOAc (3×50 mL). The combined organic phase is washed with brine (40 mL), and dried over Na$_2$SO$_4$ to obtain crude 5-(3,5-difluoro-4-((1-((1-methylcyclopropoxy)carbonyl)piperidin-4-yl)methoxy)phenyl)pyrimidine-2-carboxylic acid J1b: MS calcd. for [M+H]$^+$ C$_{22}$H$_{24}$F$_2$N$_3$O$_5$: 448.2. found: 448.2.

Step E: A solution of Intermediate J1b (313 mg, 0.7 mmol) in THF (5 ml) is treated with a solution of HATU (380 mg, 1 mmol) in DMF (4 mL) and stirred for 20 min at rt. Piperidin-4-ol (150 mg, 1.5 mmol) is added followed by DIEA (261 μL, 1.5 mmol), and stirred overnight at rt. H$_2$O (100 mL) is added and the product is extracted with EtOAc (3×50 mL). The organic layer is washed with H$_2$O (30 mL), dried (Na$_2$SO$_4$) and concentrated in vacuo. Purification by flash chromatography (MeOH/CH$_2$Cl$_2$ gradient) and recrystallization from EtOAc-hexanes affords Example J1 as a white solid: $^1$H-NMR (400 MHz, CDCl$_3$) δ=8.93 (s, 2H), 7.15 (m, 2H), 4.00-4.30 (m, 6H), 3.59 (m, 2H), 3.21 (ddd, J=13.6, 8.4, 3.6 Hz, 1H), 2.77 (t, J=12.4 Hz, 2H), 1.82-2.08 (m, 5H), 1.57-1.75 (m, 2H), 1.50 (d, J=4.0 Hz, 1H), 1.55 (s, 3H), 1.26 (m, 2H), 0.87 (m, 2H), 0.63 (m, 2H); MS calcd. for [M+H]$^+$ C$_{27}$H$_{33}$F$_2$N$_4$O$_5$: 531.2. found: 531.2.

By repeating the procedure described in the above Example J1, using appropriate starting materials, the following compounds of Formula I, as identified in Table 6, are obtained:

TABLE 6

| Example # | Structure | NMR and/or ESMS |
|---|---|---|
| J2 | 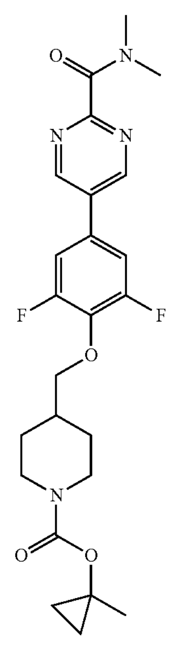 | $^1$H-NMR (400 MHz, DMSO-d6) δ = 9.25 (s, 2H), 7.80 (m, 2H), 4.05 (d, J = 6.4 Hz, 2H), 3.93 (m, 2H), 3.03 (s, 3H), 2.82 (s, 3H), 2.75 (m, 2H), 1.92 (m, 1H), 1.76 (m, 2H), 1.46 (s, 3H), 1.16 (m, 2H), 0.76 (m, 2H), 0.60 (m, 2H); MS calcd. for [M + H]$^+$ C$_{24}$H$_{29}$F$_2$N$_4$O$_4$: 475.2, found: 475.2. |

TABLE 6-continued

| Example # | Structure | NMR and/or ESMS |
|---|---|---|
| J3 | 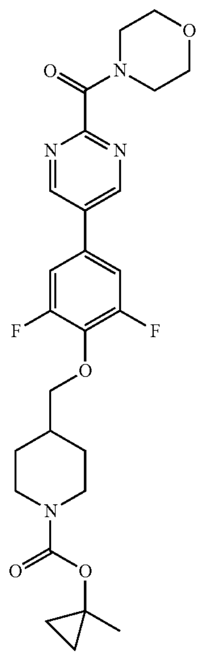 | $^1$H-NMR (400 MHz, DMSO-d6) δ = 9.26 (s, 2H), 7.80 (m, 2H), 4.05 (d, J = 6.4 Hz, 2H), 3.93 (m, 2H), 3.68 (s, 4H), 3.54 (m, 2H), 3.23 (m, 2H), 2.75 (m, 2H), 1.92 (m, 1H), 1.76 (m, 2H), 1.46 (s, 3H), 1.16 (m, 2H), 0.76 (m, 2H), 0.60 (m, 2H); MS calcd. for [M + H]$^+$ C$_{26}$H$_{31}$F$_2$N$_4$O$_5$: 517.2, found: 517.2. |
| J4 | 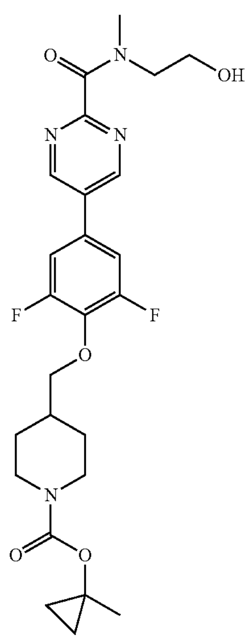 | $^1$H-NMR (400 MHz, DMSO-d6) δ = 9.252 and 9.247 (s, 2H), 7.81 (m, 2H), 4.86 (t, J = 5.2 Hz, 0.43 H), 4.70 (t, J = 5.4 Hz, 0.57 H), 4.05 (d, J = 6.4 Hz, 2H), 3.94 (m, 2H), 3.64 (m, 0.86 H), 3.54 (t, J = 5.6 Hz, 0.86H), 3.47 (m, 1.14 H), 3.21 (t, J = 6.0 Hz, 1.14 H), 3.06 (s, 1.71H), 2.86 (s, 1.29H), 2.76 (m, 2H), 1.92 (m, 1H), 1.76 (m, 2H), 1.46 (s, 3H), 1.16 (m, 2H), 0.76 (m, 2H), 0.60 (m, 2H); MS calcd. for [M + H]$^+$ C$_{25}$H$_{31}$F$_2$N$_4$O$_5$: 505.2, found: 505.2. |

TABLE 6-continued
| Example # | Structure | NMR and/or ESMS |
|---|---|---|
| J5 | 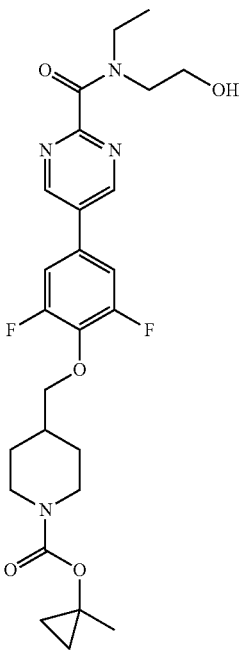 | $^1$H-NMR (400 MHz, CDCl$_3$, rotamers, largest peak is reported first) δ = 8.95 and 8.94 (s, 2H), 7.16 (m, 2H), 4.00-4.32 (m, 4H), 3.83 and 3.97 (m, 2H), 3.48 and 3.75 (t, J = 5.2 Hz, 2H), 3.35 and 3.67 (q, J = 7.2 Hz, 2H), 2.76 (m, 2H), 1.98 (m, 1H), 1.85 (m, 2H), 1.55 (s, 3H), 1.28 (m, 6H), 0.86 (m, 2H), 0.62 (m, 2H); MS calcd. for [M + H]$^+$ C$_{26}$H$_{33}$F$_2$N$_4$O$_5$: 519.2, found: 519.2. |
| J6 | 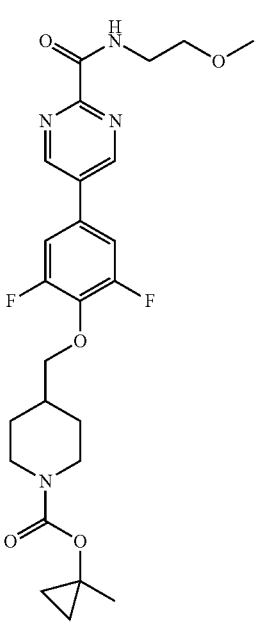 | $^1$H-NMR (400 MHz, DMSO-d6) δ = 9.31 (s, 2H), 8.87 (m, 1H), 7.85 (m, 2H), 4.06 (d, J = 6.4 Hz, 2H), 3.94 (m, 2H), 3.49 (m, 4H), 3.28 (s, 3H), 2.76 (m, 2H), 1.92 (m, 1H), 1.76 (m, 2H), 1.46 (s, 3H), 1.16 (m, 2H), 0.76 (m, 2H), 0.60 (m, 2H); MS calcd. for [M + H]$^+$ C$_{25}$H$_{31}$F$_2$N$_4$O$_5$: 505.2, found: 505.2. |

TABLE 6-continued
| Example # | Structure | NMR and/or ESMS |
|---|---|---|
| J7 | 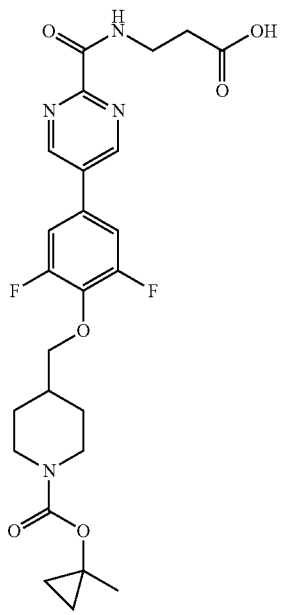 | $^{1}$H-NMR (400 MHz, DMSO-d6) δ = 12.31 (s, 1H), 9.31 (s, 2H), 8.96 (t, J = 5.8 Hz, 1H), 7.84 (m, 2H), 4.05 (d, J = 6.4 Hz, 2H), 3.94 (m, 2H), 3.52 (m, 2H), 2.75 (m, 2H), 2.55 (t, J = 7.2 Hz, 2H), 1.91 (m, 1H), 1.75 (m, 2H), 1.46 (s, 3H), 1.16 (m, 2H), 0.76 (m, 2H), 0.60 (m, 2H); MS calcd. for [M + H]$^+$ C$_{25}$H$_{29}$F$_2$N$_4$O$_6$: 519.2, found: 519.2. |
| J8 | 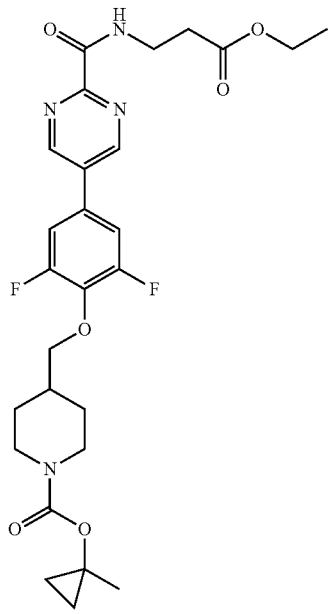 | $^{1}$H-NMR (400 MHz, DMSO-d6) δ = 9.31 (s, 2H), 9.02 (t, J = 6.0 Hz, 1H), 7.85 (m, 2H), 3.80-4.11 (m, 6H), 3.56 (m, 2H), 2.77 (m, 2H), 2.62 (t, J = 7.2 Hz, 2H), 1.92 (m, 1H), 1.76 (m, 2H), 1.47 (s, 3H), 1.18 (m, 5H), 0.76 (m, 2H), 0.60 (m, 2H); MS calcd. for [M + H]$^+$ C$_{27}$H$_{33}$F$_2$N$_4$O$_6$: 547.2, found: 547.2. |

TABLE 6-continued
| Example # | Structure | NMR and/or ESMS |
|---|---|---|
| J9 | 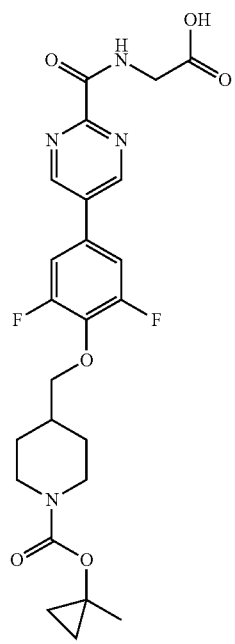 | $^1$H-NMR (400 MHz, DMSO-d6) δ = 12.71 (s, 1H), 9.34 (s, 2H), 9.17 (t, J = 6.0 Hz, 1H), 7.87 (m, 2H), 3.72-4.10 (m, 6H), 2.76 (m, 2H), 1.91 (m, 1H), 1.76 (m, 2H), 1.46 (s, 3H), 1.17 (m, 2H), 0.76 (m, 2H), 0.60 (m, 2H); MS calcd. for [M + H]$^+$ C$_{24}$H$_{27}$F$_2$N$_4$O$_6$: 505.2, found: 505.2. |
| J10 | 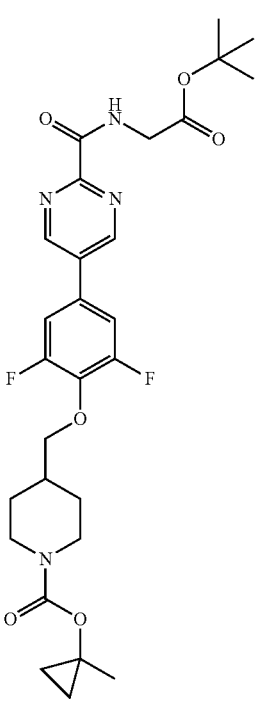 | $^1$H-NMR (400 MHz, DMSO-d6) δ = 9.34 (s, 2H), 9.21 (t, J = 6.0 Hz, 1H), 7.88 (m, 2H), 3.82-4.09 (m, 6H), 2.76 (m, 2H), 1.92 (m, 1H), 1.76 (m, 2H), 1.46 (s, 3H), 1.44 (s, 9H), 1.17 (m, 2H), 0.77 (m, 2H), 0.60 (m, 2H); MS calcd. for [M + H]$^+$ C$_{28}$H$_{35}$F$_2$N$_4$O$_6$: 561.2, found: 561.3. |

TABLE 6-continued

| Example # | Structure | NMR and/or ESMS |
|---|---|---|
| J11 | 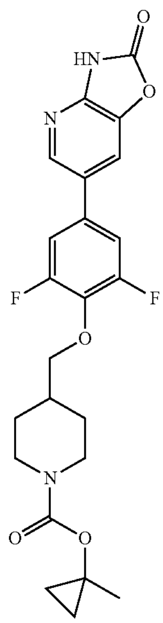 | $^1$H-NMR (400 MHz, DMSO-d6) δ = 8.16 (d, J = 2.0 Hz, 1H), 7.55 (s, 1H), 7.46 (m, 2H), 3.92 (m, 4H), 2.75 (m, 2H), 1.90 (m, 1H), 1.75 (m, 2H), 1.46 (s, 3H), 1.15 (m, 2H), 0.76 (m, 2H), 0.59 (m, 2H); MS calcd. for [M + H]$^+$ C$_{23}$H$_{24}$F$_2$N$_3$O$_5$: 460.2, found: 460.2. |
| J12 | 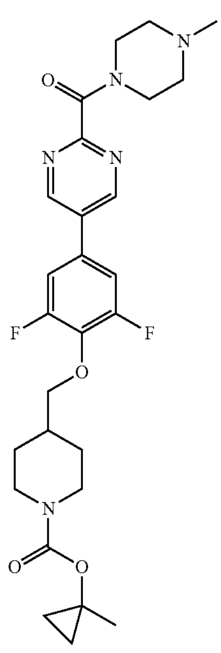 | $^1$H-NMR (400 MHz, CDCl$_3$) δ = 8.93 (s, 2H), 7.15 (m, 2H), 4.14 (m, 2H), 4.05 (d, J = 6.4 Hz, 2H), 3.87 (m, 2H), 3.43 (m, 2H), 2.76 (t, J =2.4 Hz, 2H), 2.54 (m, 2H), 2.43 (m, 2H), 2.33 (s, 3H), 1.98 (m, 1H), 1.85 (m, 2H), 1.55 (s, 3H), 1.28 (m, 2H), 0.86 (m, 2H), 0.62 (m, 2H); MS calcd. for [M + H]$^+$ C$_{27}$H$_{34}$F$_2$N$_5$O$_4$: 530.3, found: 530.2. |

TABLE 6-continued
| Example # | Structure | NMR and/or ESMS |
|---|---|---|
| J13 | 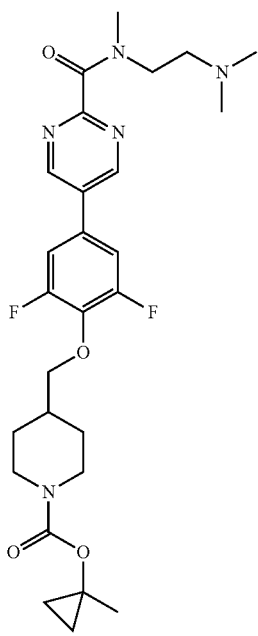 | $^1$H-NMR (400 MHz, DMSO-d6, rotamers, HCl salt) δ = 9.94 and 10.08 (bs, 1H), 9.287 and 9.282 (s, 2H), 7.82 (m, 2H), 4.05 (d, J = 6.4 Hz, 2H), 3.70-4.02 (m, 3.2H), 3.52 (m, 0.8H), 3.37 (m, 2H), 3.06 (s, 1.1H), 2.88 (m, 5.8H), 2.76 (m, 4.1H), 3.09 (m, 2H), 1.91 (m, 1H), 1.76 (m, 2H), 1.46 (s, 3H), 1.17 (m, 2H), 0.76 (m, 2H), 0.60 (m, 2H); MS calcd. for [M + H]$^+$ C$_{27}$H$_{36}$F$_2$N$_5$O$_4$: 532.3, found: 532.2. |
| J14 | 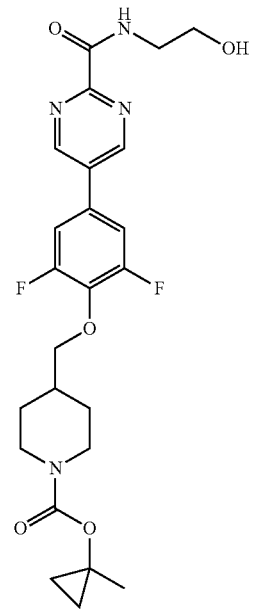 | $^1$H-NMR (400 MHz, DMSO-d6) δ = 9.31 (s, 2H), 8.84 (t, J = 5.6 Hz, 1H), 7.85 (m, 2H), 4.82 (t, J = 5.6 Hz, 1H), 4.06 (d, J = 6.4 Hz, 2H), 3.94 (m, 2H), 3.54 (m, 2H), 3.41 (m, 2H), 2.75 (m, 2H), 1.92 (m, 1H), 1.76 (m, 2H), 1.46 (s, 3H), 1.16 (m, 2H), 0.76 (m, 2H), 0.60 (m, 2H); MS calcd. for [M + H]$^+$ C$_{24}$H$_{29}$F$_2$N$_4$O$_5$: 491.2, found: 491.1. |

TABLE 6-continued
| Example # | Structure | NMR and/or ESMS |
|---|---|---|
| J15 | 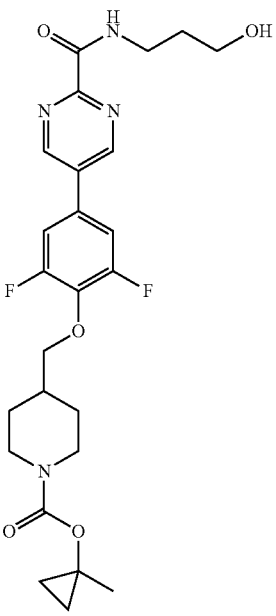 | $^1$H-NMR (400 MHz, DMSO-d6) δ = 9.30 (s, 2H), 8.98 (t, J = 6.0 Hz, 1H), 7.84 (m, 2H), 4.56 (t, J = 5.2 Hz, 1H), 4.05 (d, J = 6.4 Hz, 2H), 3.94 (m, 2H), 3.48 (m, 2H), 3.38 (m, 2H), 2.76 (m, 2H), 1.92 (m, 1H), 1.76 (m, 2H), 1.70 (p, J = 6.4 Hz, 2H), 1.46 (s, 3H), 1.17 (m, 2H), 0.76 (m, 2H), 0.60 (m, 2H); MS calcd. for [M + H]$^+$ $C_{25}H_{31}F_2N_4O_5$: 505.2, found: 505.1. |
| J16 | 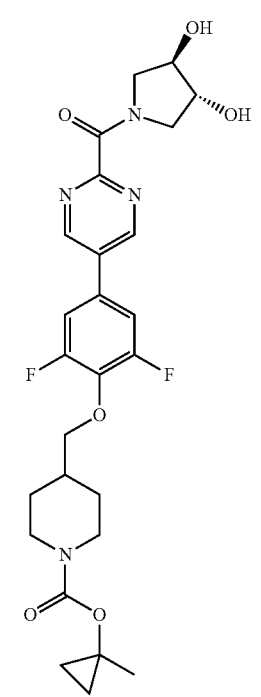 | $^1$H-NMR (400 MHz, CDCl$_3$) δ = 8.93 (s, 2H), 7.15 (m, 2H), 4.00-4.35 (m, 8H), 3.76 (m, 2H), 2.91 (m, 2H), 2.76 (t, J =12.4 Hz, 2H), 1.97 (m, 1H), 1.84 (m, 2H), 1.55 (s, 3H), 1.27 (m, 2H), 0.85 (m, 2H), 0.62 (m, 2H); MS calcd. for [M + H]$^+$ $C_{26}H_{32}F_2N_4O_5$: 533.2, found: 533.2. |

TABLE 6-continued
| Example # | Structure | NMR and/or ESMS |
|---|---|---|
| J17 | 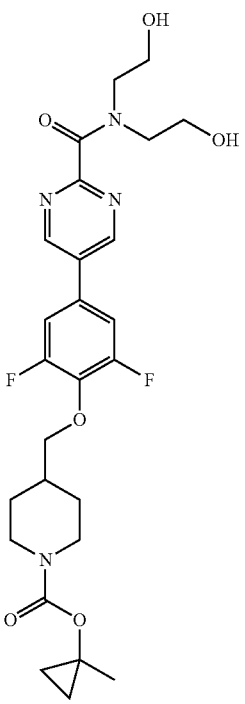 | $^1$H-NMR (400 MHz, CDCl$_3$) δ = 8.97 (s, 2H), 7.17 (m, 2H), 4.69 (bs, 1H), 4.00-4.30 (m, 6H), 3.86 (t, J = 5.2 Hz, 2H), 3.80 (t, J = 4.8 Hz, 2H), 3.56 (t, J = 5.2 Hz, 2H), 3.29 (bs, 1H), 2.77 (t, J =12.4 Hz, 2H), 1.99 (m, 1H), 1.86 (m, 2H), 1.55 (s, 3H), 1.26 (m, 2H), 0.87 (m, 2H), 0.63 (m, 2H); MS calcd. for [M + H]$^+$ C$_{26}$H$_{33}$F$_2$N$_4$O$_6$: 535.2, found: 535.0. |
| J18 | 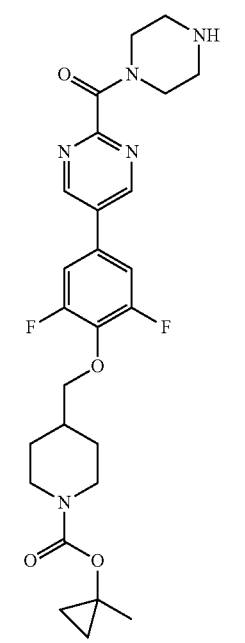 | $^1$H-NMR (400 MHz, DMSO-d6) δ = 9.24 (s, 2H), 7.79 (m, 2H), 4.05 (d, J = 6.4 Hz, 2H), 3.93 (m, 2H), 3.58 (m, 2H), 3.09 (m, 2H), 2.75 (m, 4H), 2.62 (m, 2H), 1.91 (m, 1H), 1.75 (m, 2H), 1.46 (s, 3H), 1.16 (m, 2H), 0.76 (m, 2H), 0.60 (m, 2H); MS calcd. for [M + H]$^+$ C$_{26}$H$_{32}$F$_2$N$_5$O$_4$: 516.2, found: 516.2. |

TABLE 6-continued
| Example # | Structure | NMR and/or ESMS |
|---|---|---|
| J19 | 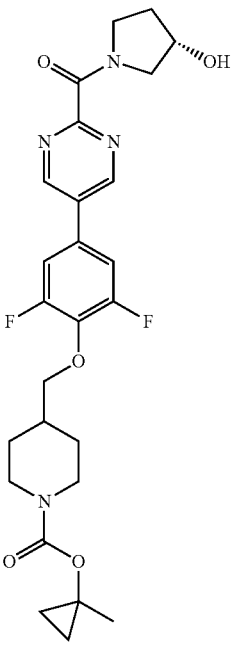 | ¹H-NMR (400 MHz, DMSO-d6) δ = 9.270 and 9.265 (s, 2H), 7.81 (m, 2H), 5.06 (d, J = 3.2 Hz, 0.5H), 5.01 (d, J = 3.6 Hz, 0.5H), 4.36 and 4.27 (m, 1H), 4.05 (d, J = 6.4 Hz, 2H), 3.93 (m, 2H), 3.33-3.65 (m, 3.5H), 3.17 (m, 0.5H), 2.76 (m, 2H), 1.71-2.02 (m, 5H), 1.46 (s, 3H), 1.17 (m, 2H), 0.76 (m, 2H), 0.60 (m, 2H); MS calcd. for [M + H]⁺ $C_{26}H_{31}F_2N_4O_5$: 517.2, found: 517.2. |
| J20 | 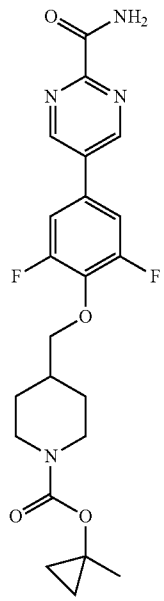 | ¹H-NMR (400 MHz, DMSO-d6) δ = 9.30 (s, 2H), 8.26 (s, 1H), 7.84 (m, 3H), 4.05 (d, J = 6.4 Hz, 2H), 3.94 (m, 2H), 2.75 (m, 2H), 1.92 (m, 1H), 1.76 (m, 2H), 1.46 (s, 3H), 1.17 (m, 2H), 0.76 (m, 2H), 0.60 (m, 2H); MS calcd. for [M + H]⁺ $C_{22}H_{25}F_2N_4O_4$: 447.2, found: 475.1. |

Example K1

2-(4-(4-((1-(5-ethylpyrimidin-2-yl)piperidin-4-yl)methoxy)-3,5-difluorophenyl)-1H-pyrazol-1-yl)-N,N-dimethylethanamine

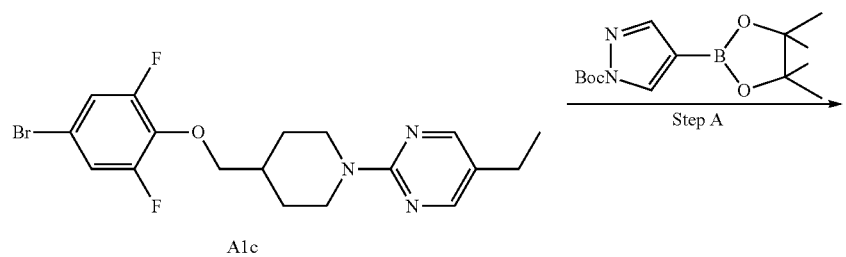

A1c

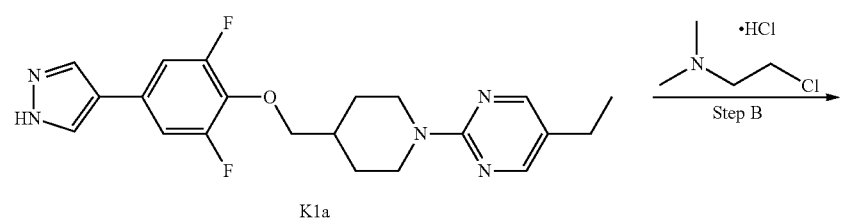

K1a

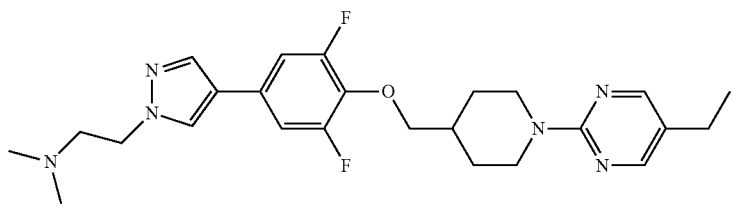

K1

Step A: In a microwave vial a mixture of Intermediate A1c (310 mg, 0.75 mmol), 6-chloro-2-methylpyridin-3-ylboronic acid (243 mg, 0.83 mmol), Pd(dppf)Cl$_2$ (33 mg, 0.045 mmol) in dry dioxane (4 mL) is treated with 1M Cs$_2$CO$_3$ (0.9 ml, 0.9 mmol). The vial is sealed and is subjected to microwave irradiation (120° C., 15 min) under nitrogen atmosphere. After cooling, the mixture is diluted with EtOAc, washed with brine, dried (Na$_2$SO$_4$) and concentrated in vacuo. Purification by flash chromatography (EtOAc/hexanes gradient) affords 2-(4-((2,6-difluoro-4-(1H-pyrazol-4-yl)phenoxy)methyl)piperidin-1-yl)-5-ethylpyrimidine K1a as a white solid: $^1$H-NMR (400 MHz, CDCl$_3$) δ=10.24 (br s, 1H), 8.19 (s, 2H), 7.80 (s, 2H), 7.06 (d, J=9.2 Hz, 2H), 4.78 (d, J=13.2 Hz, 2H), 4.02 (d, J=6.8 Hz, 2H), 2.96 (td, J=12.8, 2.8 Hz, 2H), 2.48 (q, J=7.6 Hz, 2H), 2.10 (m, 1H), 1.96 (d, J=13.2 Hz, 2H), 1.35 (qd, J=12.0, 4.0 Hz, 2H), 1.18 (t, J=7.6 Hz, 3H); $^{19}$F-NMR (376.5 MHz, CDCl$_3$) δ=−127.90; MS calcd. for [M+H]$^+$ C$_{21}$H$_{24}$F$_2$N$_5$O: 400.2. found: 400.2.

Step B: A mixture of Intermediate K1a (22 mg, 0.05 mmol), 2-chloro-N,N-dimethylethanamine hydrochloride (17 mg, 0.12 mmol) and Cs$_2$CO$_3$ (80 mg, 0.245 mmol) in MeCN (3 mL) is heated to 80° C. for 1 h. The mixture is then cooled to rt, filtered through Celite and washed with MeCN and CH$_2$Cl$_2$. The solvent is evaporated and the residue is purified by flash chromatography (EtOAc/hexanes gradient to afford the title compound (Example K1): $^1$H-NMR (400 MHz, CDCl$_3$) δ=8.17 (s, 2H), 7.66 (d, J=8.0 Hz, 2H), 6.98 (d, J=9.6 Hz, 2H), 4.76 (br. d, J=13.2 Hz, 2H), 4.23 (t, J=6.8 Hz, 2H), 3.97 (d, J=6.8 Hz, 2H), 2.91 (td, J=12.8, 2.4 Hz, 2H), 2.77 (t, J=6.8 Hz, 2H), 2.45 (q, J=7.6 Hz, 2H), 2.28 (s, 6H), 2.14-2.03 (m, 1H), 1.99-1.92 (m, 2H), 1.34 (qd, J=12.4, 4.4 Hz, 2H), 1.18 (t, J=7.6 Hz, 3H); $^{19}$F-NMR (376.5 MHz, CDCl$_3$) δ=−128.15; MS calcd. for [M+H]$^+$C$_{25}$H$_{33}$F$_2$N$_6$O: 471.3. found: 471.2.

By repeating the procedure described in the above Example K1, using appropriate starting materials, the following compounds of Formula I, as identified in Table 7, are obtained:

TABLE 7

| Example # | Structure | NMR and/or ESMS |
|---|---|---|
| K2 | (BocHN-ethyl-pyrazole-difluorophenyl-O-CH2-piperidine-pyrimidine-ethyl structure) | ¹H-NMR (400 MHz, CDCl₃) δ = 8.16 (s, 2H), 7.70 (d, J = 0.8 Hz, 1H), 7.56 (s, 1H), 6.97 (d, J = 9.6 Hz, 2H), 4.88 (br. t, 1H), 4.76 (br. d, J = 13.2 Hz, 2H), 4.24 (t, J = 5.6 Hz, 2H), 3.98 (d, J = 6.4 Hz, 2H), 3.63-3.55 (m, 2H), 2.91 (td, J = 12.8, 2.4 Hz, 2H), 2.45 (q, J = 7.6 Hz, 2H), 2.14-2.03 (m, 1H), 1.98-1.92 (m, 2H), 1.43 (s, 9H), 1.35 (qd, J = 12.4, 4.0 Hz, 2H), 1.18 (t, J = 7.2 Hz, 3H); ¹⁹F-NMR (376.5 MHz, CDCl₃) δ = −127.91; MS calcd. for [M + H]⁺ C₂₈H₃₇F₂N₆O₃: 543.3, found: 543.2. |
| K3 | (NHBoc-propyl-pyrazole-difluorophenyl-O-CH2-piperidine-pyrimidine-ethyl structure) | ¹H-NMR (400 MHz, CDCl₃) δ = 8.16 (s, 2H), 7.67 (d, J = 0.8 Hz, 1H), 7.60 (s, 1H), 6.97 (d, J = 9.2 Hz, 2H), 4.76 (br. d, J = 13.2 Hz, 2H), 4.64 (br. s, 1H), 4.20 (t, J = 6.4 Hz, 2H), 3.97 (d, J = 6.4 Hz, 2H), 3.44 (t, J = 6.4 Hz, 1H), 3.27 (q, J = 6.4 Hz, 1H), 3.13 (q, J = 6.0 Hz, 2H), 2.91 (td, J = 12.8, 2.4 Hz, 2H), 2.45 (q, J = 7.6 Hz, 2H), 2.14-2.00 (m, 1H), 2.05 (t, J = 6.4 Hz, 2H), 1.98-1.92 (m, 2H), 1.43 (s, 9H), 1.34 (qd, J = 12.4, 4.0 Hz, 2H), 1.18 (t, J = 7.6 Hz, 3H); ¹⁹F-NMR (376.5 MHz, CDCl₃) δ = −128.04; MS calcd. for [M + H]⁺ C₂₉H₃₉F₂N₆O₃: 557.3, found: 557.2. |
| K4 | (MsHN-ethyl-pyrazole-difluorophenyl-O-CH2-piperidine-pyrimidine-ethyl structure) | ¹H-NMR (400 MHz, CDCl₃) δ = 8.17 (s, 2H), 7.71 (s, 1H), 7.63 (s, 1H), 6.97 (d, J = 9.2 Hz, 2H), 5.08 (t, J = 6.4 Hz, 1H), 4.75 (br. d, J = 13.2 Hz, 2H), 4.34-4.31 (m, 2H), 3.98 (d, J = 6.8 Hz, 2H), 3.66-3.62 (m, 2H), 2.95 (s, 3H), 2.91 (td, J = 12.8, 2.8 Hz, 2H), 2.45 (q, J = 7.6 Hz, 2H), 2.14-2.02 (m, 1H), 1.98-1.92 (m, 2H), 1.33 (qd, J = 12.4, 4.4 Hz, 2H), 1.17 (t, J = 7.6 Hz, 3H); ¹⁹F-NMR (376.5 MHz, CDCl₃) δ = −127.69; MS calcd. for [M + H]⁺ C₂₄H₃₁F₂N₆O₃S: 521.2, found: 521.1. |
| K5 | (NHMs-propyl-pyrazole-difluorophenyl-O-CH2-piperidine-pyrimidine-ethyl structure) | ¹H-NMR (400 MHz, CDCl₃) δ = 8.17 (s, 2H), 7.68 (s, 1H), 7.63 (s, 1H), 6.98 (d, J = 9.2 Hz, 2H), 4.96 (t, J = 6.8 Hz, 1H), 4.76 (br. d, J = 13.2 Hz, 2H), 4.30 (t, J = 6.4 Hz, 2H), 3.97 (d, J = 6.4 Hz, 2H), 3.13 (q, J = 6.4 Hz, 2H), 2.96 (s, 3H), 2.90 (td, J = 13.2, 2.4 Hz, 2H), 2.45 (q, J = 7.6 Hz, 2H), 2.15-2.03 (m, 3H), 1.98-1.92 (m, 2H), 1.34 (qd, J = 12.8, 4.4 Hz, 2H), 1.18 (t, J = 7.6 Hz, 3H); ¹⁹F-NMR (376.5 MHz, CDCl₃) δ = −125.12; MS calcd. for [M + H]⁺ C₂₅H₃₃F₂N₆O₃S: 535.2, found: 535.2. |

TABLE 7-continued

| Example # | Structure | NMR and/or ESMS |
|---|---|---|
| K6 | 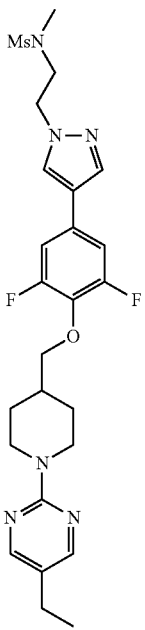 | ¹H-NMR (400 MHz, CDCl₃) δ = 8.16 (s, 2H), 7.72 (s, 1H), 7.67 (s, 1H), 6.98 (d, J = 9.2 Hz, 2H), 4.75 (br. d, J = 13.2 Hz, 2H), 4.34 (t, J = 6.0 Hz, 2H), 3.97 (d, J = 6.4 Hz, 2H), 3.61 (t, J = 5.6 Hz, 2H), 2.91 (td, J = 13.2, 2.4 Hz, 2H), 2.76 (s, 3H), 2.66 (s, 3H), 2.45 (q, J = 7.6 Hz, 2H), 2.14-2.02 (m, 1H), 1.98-1.92 (m, 2H), 1.33 (qd, J = 12.4, 4.4 Hz, 2H), 1.18 (t, J = 7.6 Hz, 3H); ¹⁹F-NMR (376.5 MHz, CDCl₃) δ = −127.82; MS calcd. for [M + H]⁺ C₂₅H₃₃F₂N₆O₃S: 535.2, found: 535.2. |
| K7 | (structure) | ¹H-NMR (400 MHz, CDCl₃) δ = 8.17 (s, 2H), 7.71 (s, 1H), 7.69 (s, 1H), 6.99 (d, J = 9.2 Hz, 2H), 4.75 (br. d, J = 13.2 Hz, 2H), 4.24 (t, J = 6.0 Hz, 2H), 3.97 (d, J = 6.4 Hz, 2H), 3.14 (t, J = 6.4 Hz, 2H), 2.91 (td, J = 13.2, 2.8 Hz, 2H), 2.85 (s, 3H), 2.79 (s, 3H), 2.45 (q, J = 7.6 Hz, 2H), 2.18 (quintet, J = 6.4 Hz, 2H), 2.10-2.01 (m, 1H), 1.99-1.92 (m, 2H), 1.33 (qd, J = 12.4, 4.0 Hz, 2H), 1.18 (t, J = 7.6 Hz, 3H); ¹⁹F-NMR (376.5 MHz, CDCl₃) δ = −128.04; MS calcd. for [M + H]⁺ C₂₆H₃₅F₂N₆O₃S: 549.2, found: 549.2. |

Example L1

N-((4'-((1-(5-ethylpyrimidin-2-yl)piperidin-4-yl)methoxy)-3',5'-difluorobiphenyl-4-yl)methyl)-N-methylacetamide

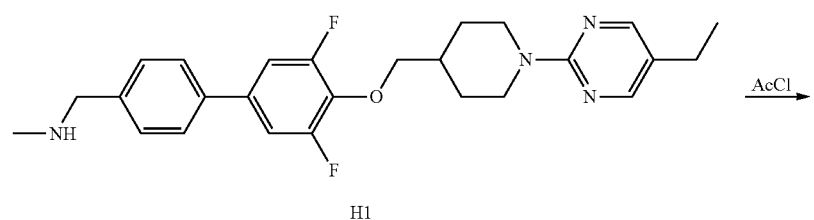

H1

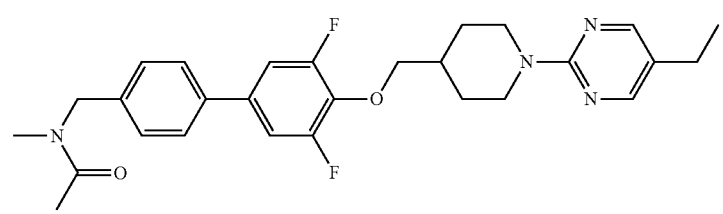

L1

A solution of Example H1 (10 mg, 0.022 mmol) in $CH_2Cl_2$ (1 mL) is treated with $NEt_3$ (9 μL, 0.066 mmol) and acetyl chloride (2.4 μL, 0.033 mmol). The mixture is then stirred at rt for 2 h, diluted with $CH_2Cl_2$, washed with sat. $NaHCO_3$ and brine, dried ($MgSO_4$) and concentrated in vacuo. Purification by flash chromatography ($SiO_2$, EtOAc/hexanes gradient) affords the title compound (Example L1): $^1$H-NMR (400 MHz, $CDCl_3$, mixture of rotamers) δ=8.17 (s, 2H), 7.51 (d, J=8.0 Hz, 1H), 7.46 (d, J=8.0 Hz, 1H), 7.30 (d, J=8.4 Hz, 1H), 7.24 (d, J=8.0 Hz, 1H), 7.11 (dd, J=9.6, 4.4 Hz, 2H), 4.75 (d, J=13.2 Hz, 2H), 4.62 (s, 1.2H), 4.57 (s, 0.8H), 4.03 (dd, J=6.8, 3.2 Hz, 2H), 3.97 (s, 3H), 2.93 (td, J=12.0, 2.0 Hz, 2H), 2.46 (q, J=7.6 Hz, 2H), 2.88 (s, 3H), 2.15-2.05 (m, 1H), 1.99-1.93 (m, 2H), 1.35 (qd, J=12.4, 4.0 Hz, 2H), 1.19 (t, J=7.6 Hz, 3H); $^{19}$F-NMR (376.5 MHz, $CDCl_3$) δ=−127.75; MS calcd. for $[M+H]^+$ $C_{28}H_{33}F_2N_4O_2$: 495.2. found: 495.3.

Example L2

N-tert-butyl-N-((4'-((1-(5-ethylpyrimidin-2-yl)piperidin-4-yl)methoxy)-3',5'-difluorobiphenyl-4-yl)methyl)acetamide

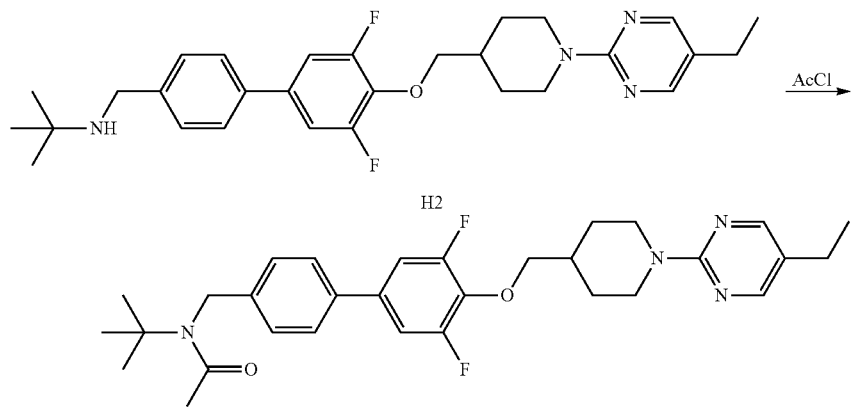

Example H2 (10 mg, ca. 0.02 mmol) is treated as described for Example L2 to afford the title compound (Example L2): $^1$H-NMR (400 MHz, $CDCl_3$) δ=8.17 (s, 2H), 7.50 (d, J=8.4 Hz, 2H), 7.29 (d, J=8.0 Hz, 2H), 7.12 (d, J=9.6 Hz, 2H), 4.77 (d, J=13.2 Hz, 2H), 4.63 (s, 2H), 4.03 (d, J=6.8 Hz, 2H), 2.92 (td, J=13.2, 2.4 Hz, 2H), 2.46 (q, J=7.6 Hz, 2H), 2.16-2.05 (m, 1H), 2.11 (s, 3H), 2.00-1.94 (m, 2H), 1.45 (s, 9H), 1.35 (qd, J=13.6, 4.8 Hz, 2H), 1.18 (t, J=7.6 Hz, 3H); $^{19}$F-NMR (376.5 MHz, $CDCl_3$) δ=−127.68; MS calcd. for $[M+H]+$ $C_{31}H_{39}F_2N_4O_2$: 537.3. found: 537.2.

Biological Assays

Generation of Stable Cell Line

Flp-In-CHO cells (Invitrogen, Cat. #R758-07) are maintained in Ham's F12 medium supplemented with 10% fetal bovine serum, 1% antibiotic mixture and 2 mM L-glutamine. The cells are transfected with a DNA mixture containing human GPR119 in pcDNA5/FRT vector and the pOG44 vector (1:9) using Fugene6 (Roche), according to the manufacturer's instruction. After 48 h, the medium is changed to medium supplemented with 400 μg/ml hygromycin B to initiate the selection of stably transfected cells.

Cyclic AMP Assay in Stable Cell Line

To test the activity of compounds of the invention, Flp-In-CHO-hGPR119 cells are harvested and resuspended in DMEM plus 3% lipid-depleted fetal bovine serum. Forth μl of cells are plated in 384 well plates at a density of 15,000 cells/well. IBMX (3-isobutyl-1-methyl-xanthine) is added to the cells to a final concentration of 1 mM, followed by the addition of 500 nl of the compound to be tested. The cells are incubated at 37° C. for 30 minutes. Equal volume (20 μl) of the HTRF reagents, anti-cAMP-Cryptate and cAMP-XL665, are added to the cells. The plates are incubated at rt for 1 h and read on a HTRF reader according to the manufacturer's instruction.

Compounds of Formula I, in free form or in pharmaceutically acceptable salt form, produced a concentration-dependent increase in intracellular cAMP level. Compound of the invention show an $EC_{50}$ of between $1\times10^{-5}$ and $1\times10^{-10}$M, preferably less than 500 nM, more preferably less than 100 nM. A representative number of compounds and their EC50 values are shown in the table, infra.

| Example # | Structure | CHO-hGPR119 cells (EC50 – nM) |
|---|---|---|
| A1 | [structure] | 1 |

-continued

| Example # | Structure | CHO-hGPR119 cells (EC50 – nM) |
|---|---|---|
| A3 | 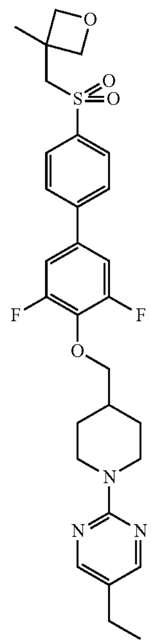 | 0.7 |
| A6 | 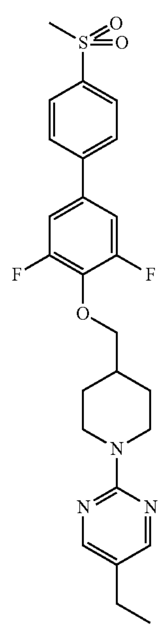 | 0.7 |
| A14 | | 5 |
| A16 | | 171 |

-continued
| Example # | Structure | CHO-hGPR119 cells (EC50 – nM) |
|---|---|---|
| A20 | 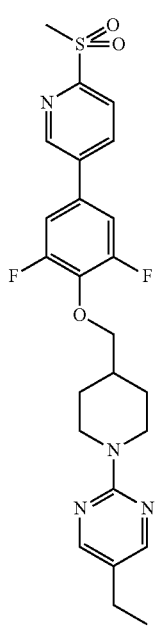 | 46 |
| A22 | 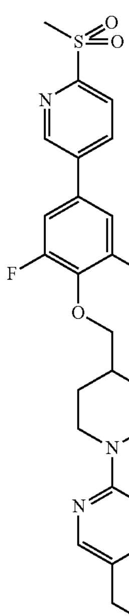 | 2 |
-continued
| Example # | Structure | CHO-hGPR119 cells (EC50 – nM) |
|---|---|---|
| A24 | 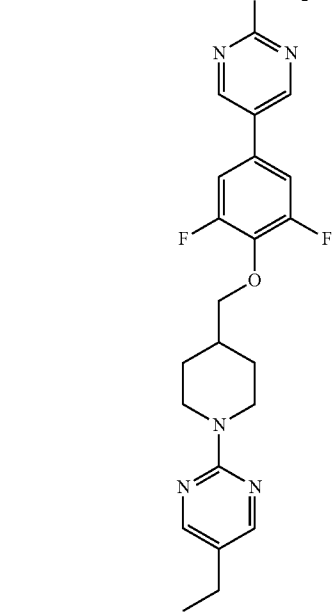 | 258 |
| A35 | | 9 |

-continued

| Example # | Structure | CHO-hGPR119 cells (EC50 – nM) |
|---|---|---|
| A38 | 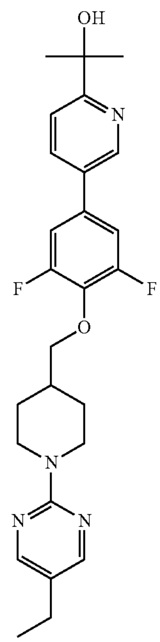 | 29 |
| A39 | 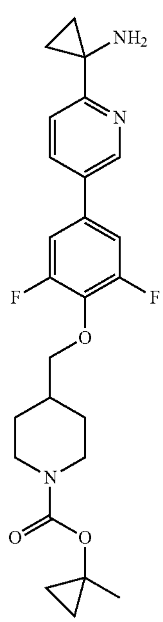 | 37 |
| B5 | | 79 |
| C1 | | 5 |

-continued

| Example # | Structure | CHO-hGPR119 cells (EC50 – nM) |
|---|---|---|
| C5 | 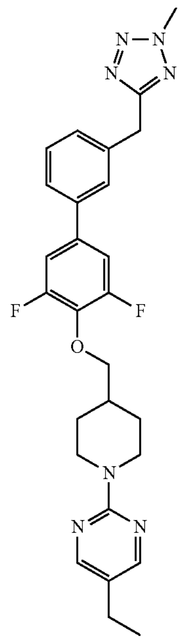 | 22 |
| D1 | 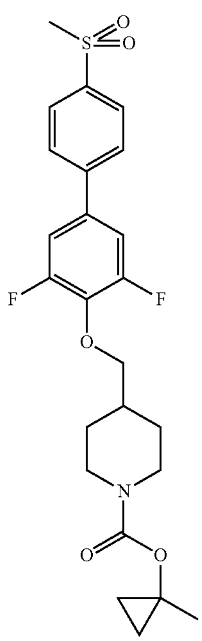 | 1 |
| E1 | | 38 |
| F1 | | 0.5 |

| Example # | Structure | CHO-hGPR119 cells (EC50 – nM) |
|---|---|---|
| F4 | 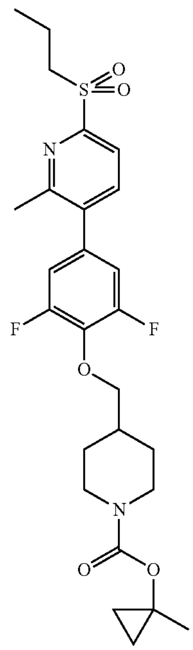 | 0.3 |
| F6 | 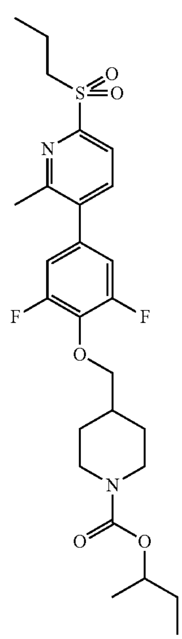 | 1 |
| G1 | | 3 |
| H4 | | 92 |

-continued

| Example # | Structure | CHO-hGPR119 cells (EC50 – nM) |
|---|---|---|
| H5 | 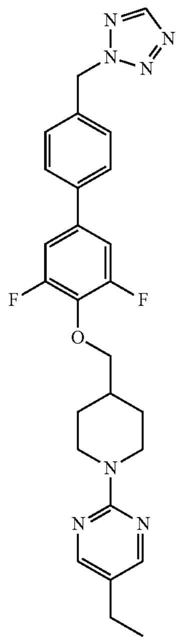 | 28 |
| I3 | 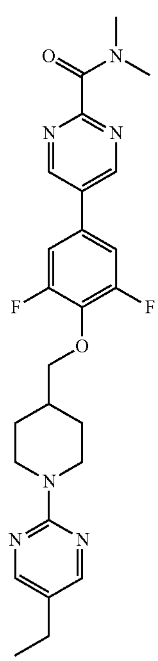 | 4 |
| J1 | | 13 |
| J5 | | 19 |

| Example # | Structure | CHO-hGPR119 cells (EC50 – nM) |
|---|---|---|
| J8 | 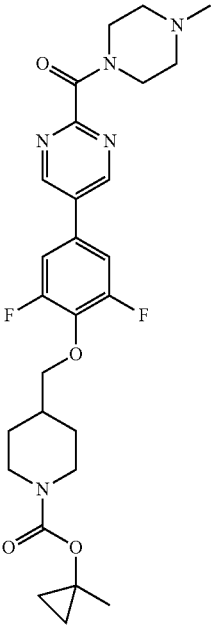 | 10 |
| J11 | 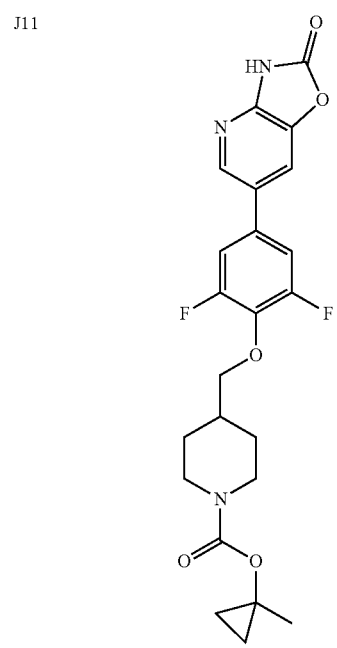 | 263 |
| J12 | | 14 |
| J15 | 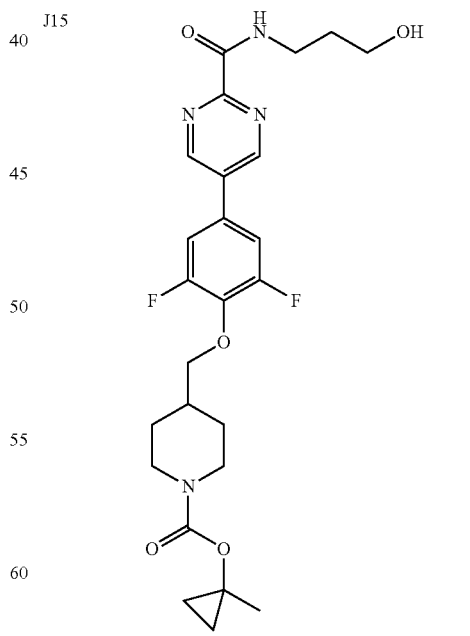 | 45 |

| Example # | Structure | CHO-hGPR119 cells (EC50 – nM) |
|---|---|---|
| J19 | 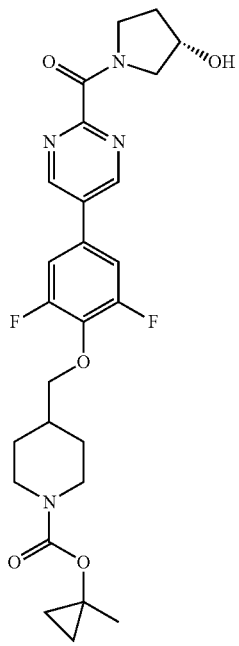 | 47 |
| K1 | 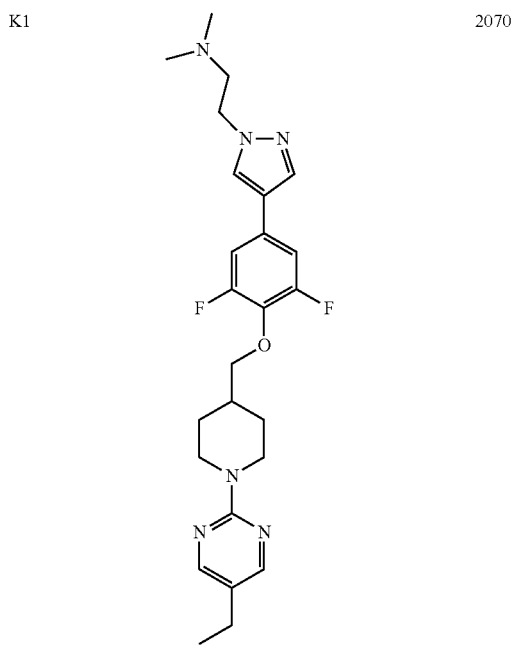 | 2070 |
| L1 | 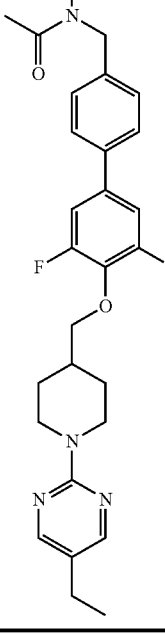 | 62 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

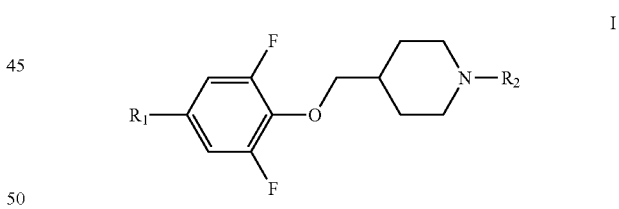

in which:
$R_1$ is selected from phenyl, pyridin-2-yl, pyridin-3-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl and 2-oxo-2,3-dihydrooxazolo[4,5-b]pyridin-6-yl;
wherein said phenyl, pyridin-2-yl, pyridin-3-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl or 2-oxo-2,3-dihydrooxazolo[4,5-b]pyridin-6-yl of $R_1$ is optionally substituted with 1 to 3 radicals independently selected from halo, —$X_1R_4$, —$X_1OR_4$, —$X_1C(O)R_4$, —$X_1C(O)OR_4$, —$X_2NR_4C(O)R_4$, —$X_1S(O)_2R_4$, —$X_1NR_4S(O)_2R_4$, —$X_1C(O)NR_4R_5$, —$X_1C(O)NR_4X_2OR_5$, —$X_1C(O)NR_4X_2NR_4R_5$, —$X_1C(O)NR_4X_2C(O)OR_5$, —$X_1S$ $(O)_{0-2}X_2R_4$, —$X_1S(O)_{0-2}X_2OR_4$, —$X_2CN$, —$X_1OX_2R_4$, —$X_1NR_5X_2R_4$, —$X_2NR_4R_5$, —$X_1S(O)_{0-2}X_2C(O)R_4$, —$X_1S(O)_{0-2}X_2C(O)OR_4$ and —$X_1S(O)_{0-2}NR_4R_5$; wherein $X_1$ is selected from a bond, O, and $C_{1-4}$alkylene; $R_5$ is selected from hydrogen and $C_{1-6}$alkyl; each $X_2$ is independently selected from a bond and $C_{1-4}$alkylene; each $R_4$ is independently selected from hydrogen, $C_{1-6}$alkyl, $C_{6-10}$aryl, $C_{1-10}$heteroaryl, $C_{3-8}$heterocycloalkyl, $C_{3-8}$cycloalkyl and —$X_3C(O)OR_7$, —$X_3R_7$, —$X_3OR_7$, —$X_3NR_7R_8$; wherein said alkyl, aryl, heteroaryl, cycloalkyl and heterocycloalkyl of $R_4$ is optionally substituted with 1 to 3 radicals independently selected from hydroxy, halo, amino, cyano, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, $C_{6-10}$aryl-$C_{1-4}$alkoxy and —$NR_7C(O)R_8$; $X_3$ is $C_{1-3}$alkylene; and $R_7$ is selected from hydrogen, $C_{1-6}$alkyl and $C_{3-8}$heterocycloalkyl optionally substituted with $C_{1-6}$alkyl; $R_8$ are independently selected from hydrogen and $C_{1-6}$alkyl; and $R_2$ is selected from $R_9$ and —$C(O)OR_9$; wherein $R_9$ is selected from $C_{1-6}$alkyl, $C_{6-10}$aryl, $C_{1-10}$heteroaryl, $C_{3-8}$cycloalkyl and $C_{3-8}$heterocycloalkyl; wherein said alkyl, aryl, heteroaryl, cycloalkyl or heterocycloalkyl of $R_9$ is optionally substituted with 1 to 3 radicals independently selected from halo, $C_{1-6}$alkyl, $C_{3-12}$cycloalkyl, $C_{3-8}$heterocycloalkyl, halo-substituted-$C_{1-6}$alkyl, hydroxy-substituted-$C_{1-6}$alkyl, $C_{1-6}$alkoxy and halo-substituted-$C_{1-6}$alkoxy; or the pharmaceutically acceptable salts thereof.

2. The compound of claim 1 in which $R_2$ is selected from 5-ethylpyrimidin-2-yl, tert-butoxycarbonyl and (1-methylcyclopropoxy)carbonyl.

3. The compound of claim 2 in which $R_1$ is selected from phenyl, pyridin-2-yl, pyridin-3-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl and 2-oxo-2,3-dihydrooxazolo[4,5-b]pyridin-6-yl;

wherein said phenyl, pyridin-2-yl, pyridin-3-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl or 2-oxo-2,3-dihydrooxazolo[4,5-b]pyridin-6-yl of $R_1$ is optionally substituted with 1 to 2 radicals independently selected from methyl-sulfonyl, 3-methyloxetan-3-yl)methylsulfonyl, isobutyl-sulfonyl, propyl-sulfonyl, isopropyl-sulfonyl, cyano, cyano-methyl, hydroxy-methyl, pyrrolidin-1-yl, methoxy, chloro, methyl, acetyl-amino, methyl-sulfonyl-amino, benzyl-oxy, amino-carbonyl, carboxyl, 2-hydroxypropan-2-yl, 1-aminocyclopropyl, 2H-tetrazol-5-yl, 2H-tetrazol-5-yl-methyl, 1H-tetrazol-5-yl, 1-methyl-1H-tetrazol-5-yl, 2-methyl-2H-tetrazol-5-yl-methyl, 1H-1,2,4-triazol-1-yl, oxazol-5-yl, 1H-pyrazol-3-yl, methyl-amino-methyl, t-butoxy-amino-methyl, morpholino-methyl, 1H-imidazol-1-yl-methyl, 2H-tetrazol-2-yl-methyl, 1H-tetrazol-1-yl-methyl, methyl-amino-carbonyl, dimethyl-amino-carbonyl, methyl-piperazinyl, piperazinyl-carbonyl, morpholino-carbonyl, 2-methoxyethylcarbamoyl, 2-hydroxyethylcarbamoyl and 2-hydroxypropylcarbamoyl.

4. The compound of claim 3 selected from:
2-(4-((2,6-difluoro-4-(5-(methylsulfonyl)pyridin-2-yl)phenoxy)methyl)piperidin-1-yl)-5-ethylpyrimidine;
tert-butyl 4-((3,5-difluoro-4'-(methylsulfonyl)biphenyl-4-yloxy)methyl)piperidine-1-carboxylate;
2-(4-((3,5-difluoro-4'-((3-methyloxetan-3-yl)methylsulfonyl)biphenyl-4-yloxy)methyl)piperidin-1-yl)-5-ethylpyrimidine;
2-(4-((3,5-difluoro-4'-(isobutylsulfonyl)biphenyl-4-yloxy)methyl)piperidin-1-yl)-5-ethylpyrimidine;
2-(4-((3,5-difluoro-4'-(propylsulfonyl)biphenyl-4-yloxy)methyl)piperidin-1-yl)-5-ethylpyrimidine;
2-(4-((3,5-difluoro-4'-(methylsulfonyl)biphenyl-4-yloxy)methyl)piperidin-1-yl)-5-ethylpyrimidine;
2-(4-((3,5-difluoro-4'-(isopropylsulfonyl)biphenyl-4-yloxy)methyl)piperidin-1-yl)-5-ethylpyrimidine;
4'-((1-(5-ethylpyrimidin-2-yl)piperidin-4-yl)methoxy)-3',5'-difluorobiphenyl-4-carbonitrile;
4'-((1-(5-ethylpyrimidin-2-yl)piperidin-4-yl)methoxy)-3',5'-difluorobiphenyl-3-carbonitrile;
2-(4'-((1-(5-ethylpyrimidin-2-yl)piperidin-4-yl)methoxy)-3',5'-difluorobiphenyl-3-yl)acetonitrile;
(4'-((1-(5-ethylpyrimidin-2-yl)piperidin-4-yl)methoxy)-3',5'-difluorobiphenyl-3-yl)methanol; 2-(4-((3,5-difluoro-3'-(methylsulfonyl)biphenyl-4-yloxy)methyl)piperidin-1-yl)-5-ethylpyrimidine;
2-(4'-((1-(5-ethylpyrimidin-2-yl)piperidin-4-yl)methoxy)-3',5'-difluorobiphenyl-4-yl)acetonitrile;
(4'-((1-(5-ethylpyrimidin-2-yl)piperidin-4-yl)methoxy)-3',5'-difluorobiphenyl-4-yl)methanol;
2-(4-((2,6-difluoro-4-(2-(pyrrolidin-1-yl)pyrimidin-5-yl)phenoxy)methyl)piperidin-1-yl)-5-ethylpyrimidine;
2-(4-((2,6-difluoro-4-(pyrimidin-5-yl)phenoxy)methyl)piperidin-1-yl)-5-ethylpyrimidine;
2-(4-((3,5-difluorobiphenyl-4-yloxy)methyl)piperidin-1-yl)-5-ethylpyrimidine;
2-(4-((2,6-difluoro-4-(6-(methylsulfonyl)pyridin-3-yl)phenoxy)methyl)piperidin-1-yl)-5-ethylpyrimidine;
2-(4-((4-(6-chloro-2-methylpyridin-3-yl)-2,6-difluorophenoxy)methyl)piperidin-1-yl)-5-ethylpyrimidine;
2-(4-((2,6-difluoro-4-(1-methyl-1H-pyrazol-4-yl)phenoxy)methyl)piperidin-1-yl)-5-ethylpyrimidine;
2-(4-((2,6-difluoro-4-(1H-pyrazol-4-yl)phenoxy)methyl)piperidin-1-yl)-5-ethylpyrimidine;
5-(4-((1-(5-ethylpyrimidin-2-yl)piperidin-4-yl)methoxy)-3,5-difluorophenyl)picolinonitrile;
N-(4'-((1-(5-ethylpyrimidin-2-yl)piperidin-4-yl)methoxy)-3',5'-difluorobiphenyl-4-yl)acetamide;
N-(4'-((1-(5-ethylpyrimidin-2-yl)piperidin-4-yl)methoxy)-3',5'-difluorobiphenyl-4-yl)methanesulfonamide;
2-(4-((4-(6-(benzyloxy)pyridin-3-yl)-2,6-difluorophenoxy)methyl)piperidin-1-yl)-5-ethylpyrimidine;
5-(4-((1-(5-ethylpyrimidin-2-yl)piperidin-4-yl)methoxy)-3,5-difluorophenyl)pyridin-2(1H)-one;
2-(4-((2,6-difluoro-4-(2-methoxypyrimidin-5-yl)phenoxy)methyl)piperidin-1-yl)-5-ethylpyrimidine;
5-(4-((1-(5-ethylpyrimidin-2-yl)piperidin-4-yl)methoxy)-3,5-difluorophenyl)pyrimidin-2(1H)-one;
5-(4-((1-(5-ethylpyrimidin-2-yl)piperidin-4-yl)methoxy)-3,5-difluorophenyl)pyrimidine-2-carboxamide;
tert-butyl 4-((2,6-difluoro-4-(pyridin-3-yl)phenoxy)methyl)piperidine-1-carboxylate;
5-(4-((1-(5-ethylpyrimidin-2-yl)piperidin-4-yl)methoxy)-3,5-difluorophenyl)pyrimidine-2-carboxylic acid;
2-(5-(4-((1-(5-ethylpyrimidin-2-yl)piperidin-4-yl)methoxy)-3,5-difluorophenyl)pyridin-2-yl)propan-2-ol;
2-(4-((3,5-difluoro-4'-(1H-tetrazol-5-yl)biphenyl-4-yloxy)methyl)piperidin-1-yl)-5-ethylpyrimidine;
2-(4-((3,5-difluoro-3'-(2H-tetrazol-5-yl)biphenyl-4-yloxy)methyl)piperidin-1-yl)-5-ethylpyrimidine;
2-(4-((3'-((2H-tetrazol-5-yl)methyl)-3,5-difluorobiphenyl-4-yloxy)methyl)piperidin-1-yl)-5-ethylpyrimidine;

2-(4-((4'-((2H-tetrazol-5-yl)methyl)-3,5-difluorobiphenyl-4-yloxy)methyl)piperidin-1-yl)-5-ethylpyrimidine;
2-(4-((4-(6-(2H-tetrazol-5-yl)pyridin-3-yl)-2,6-difluorophenoxy)methyl)piperidin-1-yl)-5-ethylpyrimidine;
2-(4-((3,5-difluoro-4'-(2-methyl-2H-tetrazol-5-yl)biphenyl-4-yloxy)methyl)piperidin-1-yl)-5-ethylpyrimidine;
2-(4-((3,5-difluoro-4'-(1-methyl-1H-tetrazol-5-yl)biphenyl-4-yloxy)methyl)piperidin-1-yl)-5-ethylpyrimidine;
2-(4-((3,5-difluoro-3'-(2-methyl-2H-tetrazol-5-yl)biphenyl-4-yloxy)methyl)piperidin-1-yl)-5-ethylpyrimidine;
2-(4-((3,5-difluoro-3'-(1-methyl-1H-tetrazol-5-yl)biphenyl-4-yloxy)methyl)piperidin-1-yl)-5-ethylpyrimidine;
2-(4-((3,5-difluoro-3'-((2-methyl-2H-tetrazol-5-yl)methyl)biphenyl-4-yloxy)methyl)piperidin-1-yl)-5-ethylpyrimidine;
2-(4-((3,5-difluoro-3'-((1-methyl-1H-tetrazol-5-yl)methyl)biphenyl-4-yloxy)methyl)piperidin-1-yl)-5-ethylpyrimidine;
2-(4-((3,5-difluoro-4'-((2-methyl-2H-tetrazol-5-yl)methyl)biphenyl-4-yloxy)methyl)piperidin-1-yl)-5-ethylpyrimidine;
2-(4-((3,5-difluoro-4'-((1-methyl-1H-tetrazol-5-yl)methyl)biphenyl-4-yloxy)methyl)piperidin-1-yl)-5-ethylpyrimidine;
2-(4-((2,6-difluoro-4-(6-(2-methyl-2H-tetrazol-5-yl)pyridin-3-yl)phenoxy)methyl)piperidin-1-yl)-5-ethylpyrimidine;
2-(4-((2,6-difluoro-4-(6-(1-methyl-1H-tetrazol-5-yl)pyridin-3-yl)phenoxy)methyl)piperidin-1-yl)-5-ethylpyrimidine;
1-methylcyclopropyl 4-((3,5-difluoro-4'-(methylsulfonyl)biphenyl-4-yloxy)methyl)piperidine-1-carboxylate;
4-(4-(((1-(tert-butoxycarbonyl)piperidin-4-yl)methoxy)-3,5-difluorophenyl)pyridine 1-oxide;
tert-butyl 4-((2,6-difluoro-4-(2-oxo-1,2-dihydropyridin-4-yl)phenoxy)methyl)piperidine-1-carboxylate;
tert-butyl 4-((2,6-difluoro-4-(1-methyl-2-oxo-1,2-dihydropyridin-4-yl)phenoxy)methyl)piperidine-1-carboxylate;
2-(4-((2,6-difluoro-4-(2-methyl-6-(1H-1,2,4-triazol-1-yl)pyridin-3-yl)phenoxy)methyl)piperidin-1-yl)-5-ethylpyrimidine;
2-(4-((2,6-difluoro-4-(2-methyl-6-(methylsulfonyl)pyridin-3-yl)phenoxy)methyl)piperidin-1-yl)-5-ethylpyrimidine;
5-(4'-((1-(5-ethylpyrimidin-2-yl)piperidin-4-yl)methoxy)-3',5'-difluorobiphenyl-4-yl)oxazole;
2-(4-((3,5-difluoro-4'-(1H-pyrazol-3-yl)biphenyl-4-yloxy)methyl)piperidin-1-yl)-5-ethylpyrimidine;
1-(4'-((1-(5-ethylpyrimidin-2-yl)piperidin-4-yl)methoxy)-3',5'-difluorobiphenyl-4-yl)—N-methylmethanamine;
N-((4'-((1-(5-ethylpyrimidin-2-yl)piperidin-4-yl)methoxy)-3',5'-difluorobiphenyl-4-yl)methyl)-2-methylpropan-2-amine;
4-((4'-((1-(5-ethylpyrimidin-2-yl)piperidin-4-yl)methoxy)-3',5'-difluorobiphenyl-4-yl)methyl)morpholino;
2-(4-((4'-((1H-imidazol-1-yl)methyl)-3,5-difluorobiphenyl-4-yloxy)methyl)piperidin-1-yl)-5-ethylpyrimidine;
2-(4-((4'-((2H-tetrazol-2-yl)methyl)-3,5-difluorobiphenyl-4-yloxy)methyl)piperidin-1-yl)-5-ethylpyrimidine;
2-(4-((4'-((1H-tetrazol-1-yl)methyl)-3,5-difluorobiphenyl-4-yloxy)methyl)piperidin-1-yl)-5-ethylpyrimidine;
5-(4-((1-(5-ethylpyrimidin-2-yl)piperidin-4-yl)methoxy)-3,5-difluorophenyl)picolinamide;
5-(4-((1-(5-ethylpyrimidin-2-yl)piperidin-4-yl)methoxy)-3,5-difluorophenyl)-N-methylpicolinamide;
5-(4-((1-(5-ethylpyrimidin-2-yl)piperidin-4-yl)methoxy)-3,5-difluorophenyl)-N,N-dimethylpicolinamide;
1-methylcyclopropyl 4-((2,6-difluoro-4-(2-(piperazine-1-carbonyl)pyrimidin-5-yl)phenoxy)methyl)piperidine-1-carboxylate;
1-methylcyclopropyl 4-((4-(2-(dimethylcarbamoyl)pyrimidin-5-yl)-2,6-difluorophenoxy)methyl)piperidine-1-carboxylate;
1-methylcyclopropyl 4-((2,6-difluoro-4-(2-(morpholine-4-carbonyl)pyrimidin-5-yl)phenoxy)methyl)piperidine-1-carboxylate;
1-methylcyclopropyl 4-((2,6-difluoro-4-(2-(2-methoxyethylcarbamoyl)pyrimidin-5-yl)phenoxy)methyl)piperidine-1-carboxylate;
1-methylcyclopropyl 4-((2,6-difluoro-4-(2-oxo-2,3-dihydrooxazolo[4,5-b]pyridin-6-yl)phenoxy)methyl)piperidine-1-carboxylate;
1-methylcyclopropyl 4-((2,6-difluoro-4-(2-(2-hydroxyethylcarbamoyl)pyrimidin-5-yl)phenoxy)methyl)piperidine-1-carboxylate; and
1-methylcyclopropyl 4-((2,6-difluoro-4-(2-(3-hydroxypropylcarbamoyl)pyrimidin-5-yl)phenoxy)methyl)piperidine-1-carboxylate.

5. The compound of claim 2 in which $R_1$ is selected from phenyl, pyridin-2-yl, pyridin-3-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl and 2-oxo-2,3-dihydrooxazolo[4,5-b]pyridin-6-yl;
wherein said phenyl, pyridin-2-yl, pyridin-3-yl, pyrimidin-5-yl, pyrazol-4-yl, 1H-pyrazol-4-yl, 6-oxo-1,6-dihydropyridin-3-yl, 2-oxo-1,2-dihydropyrimidin-5-yl, 2-oxo-1,2-dihydropyridin-4-yl or 2-oxo-2,3-dihydrooxazolo[4,5-b]pyridin-6-yl of $R_1$ is optionally substituted with 1 to 2 radicals independently selected from (S)-3-hydroxypyrrolidine-1-carbonyl, 4-hydroxypiperidine-1-carbonyl, bis(2-hydroxyethyl)carbamoyl, morpholinoethyl-amino, 4-methylpiperazin-1-yl, 1-acetamidocyclopropyl, 2-((3-methyloxetan-3-yl)methyl)-2H-tetrazol-5-yl, (2-hydroxyethyl)(methyl)carbamoyl, (2-hydroxyethyl)(ethyl)carbamoyl, 2-carboxyethylcarbamoyl, 3-ethoxy-3-oxopropylcarbamoyl, carboxymethylcarbamoyl, 2-tert-butoxy-2-oxoethylcarbamoyl, 4-methylpiperazine-1-carbonyl, (2-(dimethylamino)ethyl)(methyl)carbamoyl and 3,4-dihydroxypyrrolidine-1-carbonyl.

6. The compound of claim 5 selected from:
5-(4-((1-(5-ethylpyrimidin-2-yl)piperidin-4-yl)methoxy)-3,5-difluorophenyl)-N-(2-morpholinoethyl)pyridin-2-amine;
2-(4-((2,6-difluoro-4-(6-(4-methylpiperazin-1-yl)pyridin-3-yl)phenoxy)methyl)piperidin-1-yl)-5-ethylpyrimidine;
1-methylcyclopropyl 4-((4-(6-(1-aminocyclopropyl)pyridin-3-yl)-2,6-difluorophenoxy)methyl)piperidine-1-carboxylate;
1-methylcyclopropyl 4-((4-(6-(1-acetamidocyclopropyl)pyridin-3-yl)-2,6-difluorophenoxy)methyl)piperidine-1-carboxylate;
2-(4-((3,5-difluoro-4'-(2-((3-methyloxetan-3-yl)methyl)-2H-tetrazol-5-yl)biphenyl-4-yloxy)methyl)piperidin-1-yl)-5-ethylpyrimidine;
1-methylcyclopropyl 4-((4-(2-((3R,4R)-3,4-dihydroxypyrrolidine-1-carbonyl)pyrimidin-5-yl)-2,6-difluorophenoxy)methyl)piperidine-1-carboxylate;
1-methylcyclopropyl 4-((4-(2-((2-(dimethylamino)ethyl)(methyl)carbamoyl)pyrimidin-5-yl)-2,6-difluorophenoxy)methyl)piperidine-1-carboxylate;

1-methylcyclopropyl 4-((2,6-difluoro-4-(2-(4-methylpiperazine-1-carbonyl)pyrimidin-5-yl)phenoxy)methyl)piperidine-1-carboxylate;

1-methylcyclopropyl 4-((2,6-difluoro-4-(2-((2-hydroxyethyl)(methyl)carbamoyl)pyrimidin-5-yl)phenoxy)methyl)piperidine-1-carboxylate;

1-methylcyclopropyl 4-((4-(2-(ethyl(2-hydroxyethyl)carbamoyl)pyrimidin-5-yl)-2,6-difluorophenoxy)methyl)piperidine-1-carboxylate;

3-(5-(3,5-difluoro-4-((1-((1-methylcyclopropoxy)carbonyl)piperidin-4-yl)methoxy)phenyl)pyrimidine-2-carboxamido)propanoic acid;

1-methylcyclopropyl 4-((4-(2-(3-ethoxy-3-oxopropylcarbamoyl)pyrimidin-5-yl)-2,6-difluorophenoxy)methyl)piperidine-1-carboxylate;

2-(5-(3,5-difluoro-4-((1-((1-methylcyclopropoxy)carbonyl)piperidin-4-yl)methoxy)phenyl)pyrimidine-2-carboxamido)acetic acid;

1-methylcyclopropyl 4-((4-(2-(2-tert-butoxy-2-oxoethylcarbamoyl)pyrimidin-5-yl)-2,6-difluorophenoxy)methyl)piperidine-1-carboxylate;

1-methylcyclopropyl 4-[4-(2-(bis(2-hydroxyethyl)carbamoyl)pyrimidin-5-yl)-2,6-difluorophenoxy)methyl]piperidine-1-carboxylate;

1-methylcyclopropyl 4-((2,6-difluoro-4-(2-(4-hydroxypiperidine-1-carbonyl)pyrimidin-5-yl)phenoxy)methyl)piperidine-1-carboxylate; and (S)-1-methylcyclopropyl 4-((2,6-difluoro-4-(2-(3-hydroxypyrrolidine-1-carbonyl)pyrimidin-5-yl)phenoxy)methyl)piperidine-1-carboxylate.

7. A pharmaceutical composition comprising a therapeutically effective amount of a compound of claim 4 or claim 6 in combination with a pharmaceutically acceptable excipient.

* * * * *